US012788502B2

(12) United States Patent
Cohen et al.

(10) Patent No.: US 12,788,502 B2
(45) Date of Patent: Nov. 10, 2026

(54) INPUT ARM FOR CONTROL OF A SURGICAL MECHANICAL ARM

(71) Applicant: MOMENTIS SURGICAL LTD., Or-Yehuda (IL)

(72) Inventors: Dvir Cohen, Or-Yehuda (IL); Yaron Levinson, Or-Yehuda (IL)

(73) Assignee: MOMENTIS SURGICAL LTD., Or-Yehuda (IL)

(*) Notice: Subject to any disclaimer, the term of this patent is extended or adjusted under 35 U.S.C. 154(b) by 619 days.

(21) Appl. No.: 17/378,832

(22) Filed: Jul. 19, 2021

(65) Prior Publication Data

US 2021/0338345 A1 Nov. 4, 2021

Related U.S. Application Data

(63) Continuation of application No. 15/924,546, filed on Mar. 19, 2018, now Pat. No. 11,083,528, which is a (Continued)

(51) Int. Cl.
*A61B 34/20* (2016.01)
*A61B 34/00* (2016.01)
(Continued)

(52) U.S. Cl.
CPC .............. *A61B 34/25* (2016.02); *A61B 34/37* (2016.02); *A61B 34/74* (2016.02); *A61B 90/361* (2016.02);
(Continued)

(58) Field of Classification Search
CPC ......... A61B 34/25; A61B 34/37; A61B 34/74; A61B 90/361; A61B 34/30; A61B 90/60;
(Continued)

(56) References Cited

U.S. PATENT DOCUMENTS

| | | | |
|---|---|---|---|
| 2,165,478 | A | 7/1939 | Gross |
| 3,913,573 | A | 10/1975 | Gutnick |

(Continued)

FOREIGN PATENT DOCUMENTS

| | | |
|---|---|---|
| CN | 101040773 | 9/2007 |
| CN | 102465957 | 5/2012 |

(Continued)

OTHER PUBLICATIONS

Restriction Official Action Dated Mar. 28, 2022 from US Patent and Trademark Office Re. U.S. Appl. No. 16/672,579. (6 pages).

(Continued)

*Primary Examiner* — Adam R Mott
(74) *Attorney, Agent, or Firm* — S. J. INTELLECTUAL PROPERTY

(57) ABSTRACT

A surgical system for control of a surgical mechanical arm, which system comprises: at least one input arm comprising: a first section rotatable about a first section axis; a second section rotatable about a second section axis; a first bendable joint coupling said first and said second sections, where said first section axis and said second section axis are not collinear, for all angles of bending of said first bendable joint; at least one sensor configured to measure movement of one or more of said sections; and circuitry configured to receive a measurement signal from said at least one sensor and to generate a control signal, based on said measurement signal for control of movement of said surgical mechanical arm.

20 Claims, 35 Drawing Sheets

Related U.S. Application Data continuation of application No. 15/916,304, filed on Mar. 9, 2018, now Pat. No. 10,973,592, which is a continuation-in-part of application No. 15/454,123, filed on Mar. 9, 2017, now Pat. No. 10,463,438.

(60) Provisional application No. 62/583,559, filed on Nov. 9, 2017, provisional application No. 62/583,582, filed on Nov. 9, 2017.

(51) Int. Cl.

| | |
|---|---|
| ***A61B 34/37*** | (2016.01) |
| ***A61B 90/00*** | (2016.01) |
| *A61B 17/00* | (2006.01) |
| *A61B 34/30* | (2016.01) |
| *A61B 90/60* | (2016.01) |

(52) U.S. Cl.

CPC ............... *A61B 2017/00022* (2013.01); *A61B 2017/00199* (2013.01); *A61B 2017/00216* (2013.01); *A61B 2017/00292* (2013.01); *A61B 2017/003* (2013.01); *A61B 2017/00353* (2013.01); *A61B 2017/00398* (2013.01); *A61B 2017/00424* (2013.01); *A61B 2017/00477* (2013.01); *A61B 2017/00973* (2013.01); *A61B 34/30* (2016.02); *A61B 2034/301* (2016.02); *A61B 2034/302* (2016.02); *A61B 2034/742* (2016.02); *A61B 2090/067* (2016.02); *A61B 2090/0808* (2016.02); *A61B 90/60* (2016.02)

(58) Field of Classification Search

CPC ........... A61B 2017/00022; A61B 2017/00199; A61B 2017/00216; A61B 2017/00292; A61B 2017/003; A61B 2017/00353; A61B 2017/00398; A61B 2017/00424; A61B 2017/00477; A61B 2017/00973; A61B 2034/301; A61B 2034/302; A61B 2034/742; A61B 2090/067; A61B 2090/0808; G05G 9/04737; B25J 13/02

USPC .......................................................... 700/245

See application file for complete search history.

(56) References Cited

U.S. PATENT DOCUMENTS

| | | | |
|---|---|---|---|
| 4,054,131 | A | 10/1977 | Kessel |
| 4,364,535 | A | 12/1982 | Itoh et al. |
| 4,954,952 | A | 9/1990 | Ubhayakar et al. |
| 5,184,601 | A | 2/1993 | Putman |
| 5,597,146 | A | 1/1997 | Putman |
| 5,624,398 | A | 4/1997 | Smith et al. |
| 5,749,828 | A | 5/1998 | Solomon et al. |
| 5,810,716 | A | 9/1998 | Mukherjee et al. |
| 5,876,325 | A | 3/1999 | Mizuno et al. |
| 6,168,611 | B1 | 1/2001 | Rizvi |
| 6,231,565 | B1 | 5/2001 | Tovey et al. |
| 6,331,181 | B1 | 12/2001 | Tierney et al. |
| 6,425,865 | B1 | 7/2002 | Salcudean et al. |
| 7,008,362 | B2 | 3/2006 | Fitzgibbon |
| 7,371,210 | B2 | 5/2008 | Brock et al. |
| 7,678,117 | B2 | 3/2010 | Hinman et al. |
| 7,766,821 | B2 | 8/2010 | Brunnen et al. |
| 7,833,156 | B2 | 11/2010 | Williams et al. |
| 7,918,845 | B2 | 4/2011 | Saadat et al. |
| 8,114,050 | B2 | 2/2012 | Kaal et al. |
| 8,224,485 | B2 | 7/2012 | Unsworth |
| 8,347,754 | B1 | 1/2013 | Veltri et al. |
| 8,518,024 | B2 | 8/2013 | Williams et al. |
| 8,543,240 | B2 | 9/2013 | Itkowitz et al. |
| 8,562,610 | B2 | 10/2013 | Chabansky |
| 9,010,214 | B2 | 4/2015 | Markvicka et al. |
| 9,033,998 | B1 | 5/2015 | Schaible et al. |
| 9,662,176 | B2 | 5/2017 | Cooper et al. |
| 9,895,200 | B2 | 2/2018 | Yeung et al. |
| 10,092,344 | B2 | 10/2018 | Mohr et al. |
| 10,278,683 | B2 | 5/2019 | Robert et al. |
| 10,299,866 | B2 | 5/2019 | Cohen et al. |
| 10,463,438 | B2 | 11/2019 | Cohen |
| 10,470,831 | B2 | 11/2019 | Cohen et al. |
| 10,646,291 | B2 | 5/2020 | Turner |
| 10,667,877 | B2 | 6/2020 | Kapadia |
| 11,406,464 | B2 | 8/2022 | Peine |
| 11,850,093 | B2 | 12/2023 | Williams et al. |
| 2001/0021854 | A1 | 9/2001 | Donnez et al. |
| 2002/0087048 | A1 | 7/2002 | Brock et al. |
| 2003/0004610 | A1 | 1/2003 | Niemeyer et al. |
| 2003/0013949 | A1 | 1/2003 | Moll et al. |
| 2003/0060927 | A1 | 3/2003 | Gerbi et al. |
| 2003/0109780 | A1 | 6/2003 | Coste-Maniere et al. |
| 2003/0109857 | A1* | 6/2003 | Sanchez ................. A61B 34/37 606/1 |
| 2003/0109957 | A1 | 6/2003 | Sanchez |
| 2004/0044350 | A1 | 3/2004 | Martin et al. |
| 2004/0128026 | A1 | 7/2004 | Harris et al. |
| 2004/0138525 | A1 | 7/2004 | Saadat et al. |
| 2004/0199052 | A1 | 10/2004 | Banik et al. |
| 2004/0236316 | A1 | 11/2004 | Danitz et al. |
| 2005/0059960 | A1 | 3/2005 | Simaan et al. |
| 2005/0096694 | A1 | 5/2005 | Lee |
| 2005/0272977 | A1 | 12/2005 | Saadat et al. |
| 2006/0095022 | A1 | 5/2006 | Moll et al. |
| 2006/0142657 | A1 | 6/2006 | Quaid et al. |
| 2006/0206101 | A1 | 9/2006 | Lee |
| 2006/0241414 | A1 | 10/2006 | Nowlin et al. |
| 2007/0156019 | A1 | 7/2007 | Larkin et al. |
| 2007/0216131 | A1 | 9/2007 | Potappel |
| 2007/0221700 | A1 | 9/2007 | Ortiz et al. |
| 2007/0287992 | A1 | 12/2007 | Diolaiti et al. |
| 2008/0033597 | A1* | 2/2008 | Kraft ........................ B25J 13/02 700/264 |
| 2008/0045857 | A1 | 2/2008 | Miller et al. |
| 2008/0064921 | A1 | 3/2008 | Larkin et al. |
| 2008/0065108 | A1 | 3/2008 | Diolaiti |
| 2008/0119868 | A1 | 5/2008 | Sharp et al. |
| 2008/0125869 | A1 | 5/2008 | Paz et al. |
| 2009/0000626 | A1 | 1/2009 | Quaid et al. |
| 2009/0012531 | A1 | 1/2009 | Quaid et al. |
| 2009/0054733 | A1 | 2/2009 | Marescaux et al. |
| 2009/0099554 | A1 | 4/2009 | Forster |
| 2009/0171373 | A1 | 7/2009 | Farritor et al. |
| 2010/0016659 | A1 | 1/2010 | Weitzner |
| 2010/0022837 | A1 | 1/2010 | Ishiguro et al. |
| 2010/0170361 | A1 | 7/2010 | Bennett et al. |
| 2010/0191278 | A1 | 7/2010 | Lee et al. |
| 2010/0225209 | A1 | 9/2010 | Goldberg et al. |
| 2010/0274087 | A1 | 10/2010 | Diolaiti et al. |
| 2010/0292558 | A1 | 11/2010 | Saadat et al. |
| 2010/0318100 | A1 | 12/2010 | Okamoto et al. |
| 2011/0015650 | A1 | 1/2011 | Choi et al. |
| 2011/0022052 | A1 | 1/2011 | Jorgensen |
| 2011/0046441 | A1 | 2/2011 | Wiltshire et al. |
| 2011/0066156 | A1 | 3/2011 | McGahan et al. |
| 2011/0082462 | A1 | 4/2011 | Suarez et al. |
| 2011/0082468 | A1 | 4/2011 | Hagag et al. |
| 2011/0105843 | A1 | 5/2011 | Mueller |
| 2011/0106141 | A1 | 5/2011 | Nakamura |
| 2011/0118748 | A1 | 5/2011 | Itkowitz |
| 2011/0130718 | A1 | 6/2011 | Kidd et al. |
| 2011/0144656 | A1 | 6/2011 | Lee et al. |
| 2011/0238079 | A1* | 9/2011 | Hannaford ............. A61B 34/76 606/130 |
| 2011/0264136 | A1 | 10/2011 | Choi et al. |
| 2011/0276038 | A1 | 11/2011 | Mcintyre et al. |
| 2011/0277775 | A1 | 11/2011 | Holop et al. |
| 2011/0282356 | A1 | 11/2011 | Solomon et al. |
| 2011/0296353 | A1 | 12/2011 | Ahmed et al. |
| 2012/0010629 | A1 | 1/2012 | Mire et al. |
| 2012/0059391 | A1* | 3/2012 | Diolaiti .................. B25J 9/1689 606/130 |

(56) References Cited

U.S. PATENT DOCUMENTS

2012/0059392 A1* 3/2012 Diolaiti .................. A61B 34/30 606/130
2012/0071891 A1 3/2012 Itkowitz et al.
2012/0123207 A1 5/2012 Vargas
2012/0143211 A1 6/2012 Kishi
2012/0253131 A1 10/2012 Malkowski et al.
2012/0265007 A1 10/2012 Moriyama et al.
2013/0006267 A1 1/2013 Odermatt et al.
2013/0018303 A1 1/2013 Webster et al.
2013/0030428 A1 1/2013 Worrell et al.
2013/0035697 A1 2/2013 Ogawa et al.
2013/0060239 A1 3/2013 Hinman et al.
2013/0172904 A1 7/2013 Ikits
2013/0178867 A1 7/2013 Farritor et al.
2013/0296882 A1 11/2013 Kim et al.
2013/0345717 A1 12/2013 Markvicka et al.
2014/0039517 A1 2/2014 Bowling et al.
2014/0046340 A1 2/2014 Wilson et al.
2014/0052061 A1 2/2014 Weisshaupt
2014/0062113 A1 3/2014 Kovarik et al.
2014/0114293 A1 4/2014 Jeong et al.
2014/0222198 A1 8/2014 Emami et al.
2014/0243849 A1* 8/2014 Saglam .................. A61B 34/75 606/130
2014/0276943 A1 9/2014 Bowling et al.
2014/0316432 A1 10/2014 Malkowski
2015/0012134 A1 1/2015 Robinson et al.
2015/0038981 A1 2/2015 Kilroy et al.
2015/0230697 A1 8/2015 Phee et al.
2015/0293596 A1 10/2015 Krausen et al.
2016/0045271 A1 2/2016 McGrogan et al.
2016/0081714 A1 3/2016 Kobayashi et al.
2016/0128790 A1 5/2016 Ogawa et al.
2016/0135909 A1 5/2016 Ogawa et al.
2016/0135911 A1 5/2016 Yanagihara et al.
2016/0144504 A1 5/2016 Kuth et al.
2016/0166343 A1 6/2016 Poon et al.
2017/0071587 A1 3/2017 Harshman et al.
2017/0071687 A1 3/2017 Cohen et al.
2017/0071688 A1 3/2017 Cohen et al.
2017/0095236 A1 4/2017 Sharma et al.
2017/0095299 A1 4/2017 Hendrick et al.
2017/0112581 A1 4/2017 Cohen et al.
2017/0112583 A1 4/2017 Cohen et al.
2017/0135771 A1 5/2017 Auld et al.
2017/0135776 A1 5/2017 Cohen et al.
2017/0156808 A1 6/2017 Auld
2017/0165002 A1 6/2017 Sharma et al.
2017/0189126 A1 7/2017 Weir
2017/0231701 A1 8/2017 Cohen et al.
2017/0239005 A1 8/2017 Cohen et al.
2017/0258538 A1 9/2017 Cohen et al.
2017/0258539 A1 9/2017 Cohen et al.
2017/0273702 A1 9/2017 Dewaele et al.
2017/0274533 A1 9/2017 Berghofer et al.
2017/0296170 A1 10/2017 Shelton, IV et al.
2017/0340399 A1 11/2017 Ogawa
2018/0078034 A1* 3/2018 Savall ...................... B25J 13/06
2018/0235719 A1 8/2018 Jarc
2018/0256235 A1 9/2018 Cohen et al.
2018/0256241 A1 9/2018 Cohen et al.
2018/0256265 A1 9/2018 Cohen et al.
2018/0256266 A1 9/2018 Cohen et al.
2018/0256267 A1 9/2018 Cohen et al.
2018/0256268 A1 9/2018 Cohen et al.
2019/0000574 A1 1/2019 Dvir et al.
2019/0167363 A1 6/2019 Cohen et al.
2019/0167364 A1 6/2019 Cohen et al.
2019/0231445 A1 8/2019 Cohen et al.
2019/0357918 A1 11/2019 Otto et al.
2020/0170736 A1 6/2020 Cohen et al.
2020/0289225 A1 9/2020 Cohen et al.
2021/0196407 A1 7/2021 Cohen et al.
2022/0054205 A1 2/2022 Cohen et al.
2023/0052027 A1 2/2023 Cohen et al.

FOREIGN PATENT DOCUMENTS

CN 102596062 7/2012
CN 103120596 5/2013
DE 10122316 11/2002
EP 2550926 9/2017
JP 2006-516910 7/2006
JP 2007-509698 4/2007
JP 2008-501477 1/2008
JP 2008/132352 6/2008
JP 2009/136384 6/2009
JP 2009/136684 6/2009
JP 2010/099530 5/2010
JP 2011-004880 1/2011
JP 2011-172766 9/2011
JP 2011/528576 11/2011
JP 2012/525916 10/2012
JP 2013-126464 6/2013
JP 2014/000265 1/2014
JP 2014/516657 7/2014
JP 5744455 7/2015
JP 2019-187994 10/2019
WO WO 88/04544 6/1988
WO WO 2010/096580 8/2010
WO WO 2013/116869 8/2013
WO WO 2015/019675 2/2015
WO WO 2015/023793 2/2015
WO WO 2016/035084 3/2016
WO WO 2016/035086 3/2016
WO WO 2016/035085 8/2016
WO WO 2017/037723 3/2017
WO WO 2021/111394 6/2021
WO WO 2023/286066 1/2023

OTHER PUBLICATIONS

Notice Of Allowance Dated Jun. 15, 2022 From the US Patent and Trademark Office Re. U.S. Appl. No. 15/358,331. (23 pages).

Official Action Dated Jun. 17, 2022 from US Patent and Trademark Office Re. U.S. Appl. No. 15/916,302. (120 pages).

Requisition of the Examiner Dated Apr. 6, 2022 From the Innovation, Science and Economic Development Canada, Canadian Intellectual Property Office Re. Application No. 2,957,620 togethr with Claims. (25 Pages).

Office Action Dated Dec. 23, 2021 From the Israel Patent Office Re. Application No. 283641 and Its Translation Into English. (6 Pages).

Restriction Official Action Dated Dec. 30, 2021 from US Patent and Trademark Office Re. U.S. Appl. No. 15/916,302. (5 pages).

Restriction Official Action Dated Dec. 30, 2021 from US Patent and Trademark Office Re. U.S. Appl. No. 16/377,280. (6 pages).

Notice of Reason(s) for Rejection Dated Mar. 7, 2023 From the Japan Patent Office Re. Application No. 2021-117181 and Its Translation Into English. (7 Pages).

Requisition by the Examiner Dated May 4, 2022 From the Innovation, Science and Economic Development Canada, Canadian Intellectual Property Office Re. Application No. 2,957,624 with Claims. (9 Pages).

Official Action Dated Sep. 30, 2022 from US Patent and Trademark Office Re. U.S. Appl. No. 16/841,848. (83 pages).

Official Action Dated Jul. 6, 2023 from the US Patent and Trademark Office Re. U.S. Appl. No. 17/468,745. (87 pages).

Communication Pursuant to Article 94(3) EPC Dated Oct. 26, 2022 From the European Patent Office Re. Application No. 20187025.0. (6 Pages).

International Search Report and the Written Opinion Dated Nov. 27, 2022 From the International Searching Authority Re. Application No. PCT/IL2022/050763 (22 Pages).

Requisition by the Examiner Dated Dec. 7, 2022 From the Innovation, Science and Economic Development Canada, Canadian Intellectual Property Office Re. Application No. 2,957,362.(20 pages).

Requisition by the Examiner Dated Apr. 28, 2022 From the Innovation, Science and Economic Development Canada, Canadian Intellectual Property Office Re. Application No. 2,957,622. (3 Pages).

(56) References Cited

OTHER PUBLICATIONS

Requisition by the Examiner Dated Oct. 14, 2021 From the Innovation, Science and Economic Development Canada, Canadian Intellectual Property Office Re. Application No. 2,957,624. (22 Pages).
Requisition by the Examiner Dated Oct. 14, 2021 From the Innovation, Science and Economic Development Canada, Canadian Intellectual Property Office Re. Application No. 2,957,622. (37 Pages).
Notice of Allowance Dated May 26, 2023 From the US Patent and Trademark Office Re. U.S. Appl. No. 15/916,302. (17 Pages).
Advisory Action Before the Filing of An Appeal Brief Dated Feb. 13, 2019 From the US Patent and Trademark Office Re. U.S. Appl. No. 15/454,116. (4 pages).
Advisory Action Before the Filing of an Appeal Brief Dated Jul. 13, 2018 From the US Patent and Trademark Office Re. U.S. Appl. No. 15/454,123. (3 pages).
Advisory Action Before the Filing of An Appeal Brief Dated May 21, 2019 From the US Patent and Trademark Office Re. U.S. Appl. No. 15/312,732. (23 pages).
Advisory Action Before the Filing of An Appeal Brief Dated Jan. 24, 2019 From the US Patent and Trademark Office Re. U.S. Appl. No. 15/454,116. (5 pages).
Applicant-Initiated Interview Summary Dated Oct. 2, 2017 From the US Patent and Trademark Office Re. U.S. Appl. No. 15/358,331. (3 pages).
Applicant-Initiated Interview Summary Dated Oct. 6, 2017 From the US Patent and Trademark Office Re. U.S. Appl. No. 15/454,123. (2 pages).
Applicant-Initiated Interview Summary Dated Mar. 7, 2018 From the US Patent and Trademark Office Re. U.S. Appl. No. 15/312,732. (3 pages).
Applicant-Initiated Interview Summary Dated Jul. 19, 2017 From the US Patent and Trademark Office Re. U.S. Appl. No. 15/418,891. (3 pages).
Applicant-Initiated Interview Summary Dated Nov. 22, 2019 From the US Patent and Trademark Office Re. U.S. Appl. No. 15/501,862. (3 pages).
Applicant-Initiated Interview Summary Dated Apr. 24, 2019 From the US Patent and Trademark Office Re. U.S. Appl. No. 15/358,331. (3 Pages).
Applicant-Initiated Interview Summary Dated Jan. 26, 2018 From the US Patent and Trademark Office Re. U.S. Appl. No. 15/418,891. (3 pages).
Application-Initiated Interview Summary Dated May 31, 2019 From the US Patent and Trademark Office Re. U.S. Appl. No. 16/271,915. (3 Pages).
Communication Pursuant to Article 94(3) EPC Dated Mar. 4, 2019 From the European Patent Office Re. Application No. 15838758.9. (9 Pages).
Communication Pursuant to Article 94(3) EPC Dated Apr. 8, 2019 From the European Patent Office Re. Application No. 15838126.9. (15 Pages).
Communication Pursuant to Article 94(3) EPC Dated Mar. 11, 2019 From the European Patent Office Re. Application No. 17160061.2. (6 Pages).
Decision of Rejection Dated Apr. 10, 2019 From the State Intellectual Property Office of the People's Republic of China Re. Application No. 201580052098.8. (3 Pages).
European Search Report and the European Search Opinion Dated Nov. 4, 2020 From the European Patent Office Re. Application No. 20187025.0. (10 Pages).
European Search Report and the European Search Opinion Dated Oct. 21, 2020 From the European Patent Office Re. Application No. 20176879.3. (12 Pages).
European Search Report and the European Search Opinion Dated Aug. 22, 2017 From the European Patent Office Re. Application No. 17160061.2. (9 Pages).
Ex Parte Quayle OA Dated Nov. 7, 2018 From the US Patent and Trademark Office Re. U.S. Appl. No. 15/501,862. (8 pages).
Examiner's Answer Dated Sep. 9, 2019 Before The Patent Trial and Appeal Board of the US Patent and Trademark Office Re. U.S. Appl. No. 15/312,732. (12 pages).
Final Official Action Dated Jun. 9, 2021 From the US Patent and Trademark Office Re. U.S. Appl. No. 15/358,331. (42 Pages).
Final Official Action Dated Oct. 8, 2020 from the US Patent and Trademark Office Re. U.S. Appl. No. 15/916,304. (12 pages).
International Preliminary Report on Patentability Dated Mar. 15, 2018 From the International Bureau of WIPO Re. Application No. PCT/IL2015/050892. (9 Pages).
International Preliminary Report on Patentability Dated Mar. 16, 2017 From the International Bureau of WIPO Re. Application No. PCT/IL2015/050891. (16 Pages).
International Preliminary Report on Patentability Dated Mar. 16, 2017 From the International Bureau of WIPO Re. Application No. PCT/IL2015/050892.
International Preliminary Report on Patentability Dated Mar. 16, 2017 From the International Bureau of WIPO Re. Application No. PCT/IL2015/050893. (11 Pages).
International Search Report and the Written Opinion Dated Dec. 6, 2016 From the International Searching Authority Re. Application No. PCT/IL2015/050892. (36 Pages).
International Search Report and the Written Opinion Dated Mar. 10, 2016 From the International Searching Authority Re. Application No. PCT/IL2015/050893.
International Search Report and the Written Opinion Dated Mar. 11, 2016 From the International Searching Authority Re. Application No. PCT/IL2015/050892.
International Search Report and the Written Opinion Dated Feb. 26, 2016 From the International Searching Authority Re. Application No. PCT/IL2015/050891.
Interview Summary Dated Aug. 11, 2020 from the US Patent and Trademark Office Re. U.S. Appl. No. 15/358,331. (3 pages).
Invitation to Pay Additional Fees Dated Dec. 3, 2015 From the International Searching Authority Re. Application No. PCT/IL2015/050891.
Invitation to Pay Additional Fees Dated Jan. 12, 2016 From the International Searching Authority Re. Application No. PCT/IL2015/050893.
Notice of Allowance Dated Jul. 3, 2019 From the US Patent and Trademark Office Re. U.S. Appl. No. 16/271,922. (26 pages).
Notice of Allowance Dated May 17, 2021 From the US Patent and Trademark Office Re. U.S. Appl. No. 16/121,704. (9 Pages).
Notice of Allowance Dated Nov. 19, 2020 from the US Patent and Trademark Office Re. U.S. Appl. No. 15/916,304. (4 pages).
Notice Of Allowance Dated Nov. 21, 2019 From the US Patent and Trademark Office Re. U.S. Appl. No. 15/454,116. (36 pages).
Notice Of Allowance Dated Jul. 25, 2019 From the US Patent and Trademark Office Re. U.S. Appl. No. 16/271,915. (27 pages).
Notice Of Allowance Dated Jun. 26, 2019 From the US Patent and Trademark Office Re. U.S. Appl. No. 15/454,123. (24 pages).
Notice Of Allowance Dated Jan. 28, 2019 From the US Patent and Trademark Office Re. U.S. Appl. No. 15/924,635. (15 pages).
Notice of Allowance Dated Mar. 31, 2021 From the US Patent and Trademark Office Re. U.S. Appl. No. 15/924,546. (18 Pages).
Notice of Reason for Rejection Dated Dec. 15, 2020 From the Japan Patent Office Re. Application No. 2019-215144 and Its Translation Into English. (16 Pages).
Notice of Reasons for Rejection Dated Jul. 2, 2019 From the Japan Patent Office Re. Application No. 2017-532229 and Its Translation Into English. (11 Pages).
Notification of Office Action and Search Report Dated Dec. 2, 2019 From the State Intellectual Property Office of the People's Republic of China Re. Application No. 201580052098.8 and Its Summary in English. (7 Pages).
Notification of Office Action and Search Report Dated Jan. 15, 2021 From the State Intellectual Property Office of the People's Republic of China Re. Application No. 202011456521.X and Its English Summery. (5 Pages).
Notification of Office Action and Search Report Dated Jul. 20, 2020 From the State Intellectual Property Office of the People's Republic of China Re. Application No. 201580052098.8 and Its Translation of Office Action Into English. (6 Pages).

(56) References Cited

OTHER PUBLICATIONS

Notification of Office Action Dated Sep. 3, 2018 From the State Intellectual Property Office of the People's Republic of China Re. Application No. 201580052098.8. (4 Pages).
Notification of Office Action Dated Jan. 19, 2018 From the State Intellectual Property Office of the People's Republic of China Re. Application No. 201580052098.8. (4 Pages).
Office Action Dated Apr. 28, 2020 From the Israel Patent Office Re. Application No. 250896 and Its Translation Into English. (4 Pages).
Official Action Dated Apr. 4, 2019 From the US Patent and Trademark Office Re. U.S. Appl. No. 16/271,915. (12 pages).
Official Action Dated Dec. 4, 2017 From the US Patent and Trademark Office Re. U.S. Appl. No. 15/358,325. (20 pages).
Official Action Dated Feb. 4, 2021 From the US Patent and Trademark Office Re. U.S. Appl. No. 16/121,704. (74 Pages).
Official Action Dated Jul. 5, 2019 From the US Patent and Trademark Office Re. U.S. Appl. No. 15/501,862. (7 pages).
Official Action Dated Jun. 5, 2017 From the US Patent and Trademark Office Re. U.S. Appl. No. 15/418,891. (28 pages).
Official Action Dated Aug. 7, 2017 From the US Patent and Trademark Office Re. U.S. Appl. No. 15/358,325. (25 pages).
Official Action Dated Aug. 7, 2019 From the US Patent and Trademark Office Re. U.S. Appl. No. 15/358,331. (46 pages).
Official Action Dated Jan. 9, 2019 From the US Patent and Trademark Office Re. U.S. Appl. No. 15/358,331. (40 pages).
Official Action Dated Mar. 9, 2017 From the US Patent and Trademark Office Re. U.S. Appl. No. 15/401,045. (23 pages).
Official Action Dated Jul. 10, 2017 From the US Patent and Trademark Office Re. U.S. Appl. No. 15/358,331. (32 pages).
Official Action Dated Mar. 10, 2017 From the US Patent and Trademark Office Re. U.S. Appl. No. 15/402,342. (25 pages).
Official Action Dated Dec. 13, 2017 From the US Patent and Trademark Office Re. U.S. Appl. No. 15/402,257. (44 pages).
Official Action Dated Jan. 13, 2020 From the US Patent and Trademark Office Re. U.S. Appl. No. 15/501,862. (6 pages).
Official Action Dated Dec. 14, 2018 From the US Patent and Trademark Office Re. Application No. 15/454, 116. (27 pages).
Official Action Dated Nov. 14, 2018 From the US Patent and Trademark Office Re. U.S. Appl. No. 15/312,732. (25 pages).
Official Action Dated Dec. 17, 2020 From the US Patent and Trademark Office Re. U.S. Appl. No. 15/924,546. (78 Pages).
Official Action Dated Feb. 20, 2020 From the US Patent and Trademark Office Re. U.S. Appl. No. 15/358,331. (33 pages).
Official Action Dated Mar. 20, 2018 From the US Patent and Trademark Office Re. U.S. Appl. No. 15/454,123. (36 pages).
Official Action Dated May 21, 2020 from the US Patent and Trademark Office Re. U.S. Appl. No. 15/916,304. (82 pages).
Official Action Dated Mar. 22, 2019 From the US Patent and Trademark Office Re. U.S. Appl. No. 15/454,123. (32 pages).
Official Action Dated Jul. 23, 2018 From the US Patent and Trademark Office Re. U.S. Appl. No. 15/924,635. (20 pages).
Official Action Dated Jan. 26, 2018 From the US Patent and Trademark Office Re. U.S. Appl. No. 15/312,732. (50 pages).
Official Action Dated Nov. 27, 2017 From the US Patent and Trademark Office Re. U.S. Appl. No. 15/418,891. (35 pages).
Official Action Dated Aug. 28, 2017 From the US Patent and Trademark Office Re. U.S. Appl. No. 15/454,123. (32 pages).
Official Action Dated Feb. 28, 2018 From the US Patent and Trademark Office Re. U.S. Appl. No. 15/358,331. (34 pages).
Official Action Dated Jun. 28, 2018 From the US Patent and Trademark Office Re. U.S. Appl. No. 15/454,116. (67 pages).
Official Action Dated Sep. 28, 2020 from the US Patent and Trademark Office Re. U.S. Appl. No. 15/358,331. (35 pages).
Official Action Dated Jun. 29, 2018 From the US Patent and Trademark Office Re. U.S. Appl. No. 15/312,732. (34 pages).
Official Action Dated Jan. 30, 2019 From the US Patent and Trademark Office Re. U.S. Appl. No. 15/501,862. (6 pages).
Restriction Official Action Dated May 2, 2018 From the US Patent and Trademark Office Re. U.S. Appl. No. 15/501,862. (6 pages).
Restriction Official Action Dated Aug. 7, 2018 From the US Patent and Trademark Office Re. U.S. Appl. No. 15/501,862. (6 pages).
Restriction Official Action Dated Feb. 7, 2018 From the US Patent and Trademark Office Re. U.S. Appl. No. 15/454,116. (6 pages).
Restriction Official Action Dated Oct. 16, 2020 from the US Patent and Trademark Office Re. U.S. Appl. No. 16/121,704. (6 pages).
Restriction Official Action Dated Mar. 17, 2017 From the US Patent and Trademark Office Re. U.S. Appl. No. 15/418,891. (7 pages).
Summons to Attend Oral Proceedings Pursuant to Rule 115(1) EPC and Communication From the Examining Division Dated May 14, 2019 From the European Patent Office Re. Application No. 16840991.0 (5 Pages).
Summons to Attend Oral Proceedings Pursuant to Rule 115(1) EPC Dated Dec. 2, 2019 From the European Patent Office Re. Application No. 15838758.9. (14 Pages).
Summons to Attend Oral Proceedings Pursuant to Rule 115(1) EPC Dated Sep. 16, 2019 From the European Patent Office Re. Application No. 15838758.9. (14 Pages).
Summons to Attend Oral Proceedings Pursuant to Rule 115(1) EPC Dated Nov. 19, 2019 From the European Patent Office Re. Application No. 17160061.2. (6 Pages).
Summons to Attend Oral Proceedings Pursuant to Rule 115(1) EPC Dated Sep. 27, 2019 From the European Patent Office Re. Application No. 17160061.2. (8 Pages).
Supplementary European Search Report and the European Search Opinion Dated Apr. 9, 2018 From the European Patent Office Re. Application No. 15838758.9. (12 Pages).
Supplementary Europcan Search Report and the European Search Opinion Dated Jun. 11, 2018 From the European Patent Office Re. Application No. 15838126.9. (11 Pages).
Supplementary European Search Report and the European Search Opinion Dated Jun. 21, 2018 From the European Patent Office Re. Application No. 16840991.0 (7 Pages).
Translation Dated Dec. 5, 2019 of Notification of Office Action Dated Dec. 2, 2019 From the State Intellectual Property Office of the People's Republic of China Re. Application No. 201580052098. 8. 4 Pages).
Translation Dated Sep. 13, 2018 of Notification of Office Action Dated Sep. 3, 2018 From the State Intellectual Property Office of the People's Republic of China Re. Application No. 201580052098.8. (3 Pages).
Translation Dated Apr. 22, 2019 of Decision of Rejection Dated Apr. 10, 2019 From the State Intellectual Property Office of the People's Republic of China Re. Application No. 201580052098.8. (4 Pages).
Translation of Notification of Office Action Dated Jan. 19, 2018 From the State Intellectual Property Office of the People's Republic of China Re. Application No. 201580052098.8. (2 Pages).
Box et al. "Rapid Communciation: Robot-Assisted NOTES Nephrectomy: Initial Report", Journal of Endourology, 22(3): 503-506, Mar. 2008.
Domingo et al. "Overview of Current Trends in Hysterectomy", Expert Reviews of Obstetrics & Gynaecology, 4(6): 673-685, 2009.
Hubens et al. "What Have We Learnt After Two Years Working With the Da Vinci Robot System in Digestive Surgery?", Acta Chirurgica Belgica, 104(6): 609-614, Nov.-Dec. 2004.
Irvine et al. "Anaesthesia for Robot-Assisted Laporoscopic Surgery", Continuing Education in Anaesthesia, Critical Care & Pain, 9(4): 125-129, Advance Access Published Jun. 25, 2009.
Kho et al. "Vaginal Versus Laparoscopic Hysterectomy. Vaginal Hysterectomy: The Best Minimally Invasive Approach", Contemporary OB/GYNObstetrics & Women's Health, 7 P., Oct. 1, 2013.
Komura et al. "An Inverse Kinematics Method for 3D Figures With Motion Data", Proceedings of the Computer Graphics International, CGI'03, Jul. 9-11, 2003, p. 266-271, Jul. 2003.
Lee "Anesthetic Considerations for Robotic Surgery", Korean Journal of Anesthesiology, 66(1): 3-11, Jan. 2014.
Piccigallo et al. "Design of A Novel Bimanual Robotic System for Single-Port Laparoscopy", IEEE/ASME Transactions on Mechatronics, 15(6): 871-878, Dec. 13, 2010.
Ramos et al. "Human Hybrid NOTES Transvaginal Sleeve Gastrectomy: Initial Experience", Surgery for Obesity and Related Diseases, 4: 660-663, 2008.

(56) References Cited

OTHER PUBLICATIONS

Teljeur et al. "Economic Evaluation of Robot-Assisted Hysterectomy: A Cost-Minimisation Analysis", BJOG: An International Journal of Obstetrics and Gynaecology, 121(12): 1546-1555, Published Online May 9, 2014.
Official Action Dated May 3, 2023 from the US Patent and Trademark Office Re. U.S. Appl. No. 17/976,954. (44 pages).
Interview Summary Dated Jan. 20, 2022 from US Patent and Trademark Office Re. U.S. Appl. No. 15/358,331. (2 pages).
Requisition of the Examiner Dated Oct. 4, 2021 From the Innovation, Science and Economic Development Canada, Canadian Intellectual Property Office Re. Application No. 2,957,620. (7 Pages).
Notice of Allowance Dated Aug. 23, 2023 from the US Patent and Trademark Office Re. U.S. Appl. No. 16/672,579. (38 pages).
Office Action Dated Aug. 20, 2023 From the Israel Patent Office Re. Application No. 302177. (5 Pages).
Official Action Dated Jul. 7, 2022 from US Patent and Trademark Office Re. U.S. Appl. No. 16/377,280. (110 pages).
Notice of Allowance Dated May 12, 2023 from the US Patent and Trademark Office Re. U.S. Appl. No. 16/841,848. (24 pages).
Requisition by the Examiner Dated Oct. 3, 2023 From the Innovation, Science and Economic Development Canada, Canadian Intellectual Property Office Re. Application No. 2,957,362. (4 Pages).
Final Official Action Dated Jan. 6, 2023 From the US Patent and Trademark Office Re. U.S. Appl. No. 16/377,280. (31 Pages).
Requisition by the Examiner Dated Sep. 8, 2023 From the Innovation, Science and Economic Development Canada, Canadian Intellectual Property Office Re. Application No. 2,960,354. (7 Pages).
Notice of Reasons for Rejection Dated Jul. 26, 2022 From the Japan Patent Office Re. Application No. 2021-117181 and Its Translation Into English. (14 Pages).
Official Action Dated Jul. 11, 2023 from the US Patent and Trademark Office Re. U.S. Appl. No. 16/377,280. (24 pages).
Notification of Office Action and Search Report Dated Sep. 25, 2023 From the National Intellectual Property Administration of the People's Republic of China Re. Application No. 202011456521.X and Its Translation Into English. (14 Pages).
Advisory Action Dated Sep. 10, 2021 From the US Patent and Trademark Office Re. U.S. Appl. No. 15/358,331. (6 Pages).
Official Action Dated Oct. 4, 2022 from US Patent and Trademark Office Re. U.S. Appl. No. 16/672,579. (86 pages).
Communication Pursuant to Article 94(3) EPC Dated Oct. 13, 2022 From the European Patent Office Re. Application No. 20176879.3. (10 Pages).
Notice of Allowance Dated Nov. 3, 2022 from the US Patent and Trademark Office Re. U.S. Appl. No. 15/916,302. (19 pages).

* cited by examiner

Bend a distal bendable portion of a surgical arm, where the bendable portions is distal of at least one other proximal bendable portion, to partially retroflect the surgical arm
2200

↓

Bend the proximal bendable portion to retroflect the arm
2202

INPUT ARM FOR CONTROL OF A SURGICAL MECHANICAL ARM

RELATED APPLICATIONS

This application is a continuation of U.S. patent Ser. No. 15/924,546 filed on Mar. 19, 2018, which claims the benefit of priority under 35 USC § 119(e) of U.S. Provisional Patent Application No. 62/583,559 filed Nov. 9, 2017.

This application is also a Continuation of U.S. patent application Ser. No. 15/916,304 filed Mar. 9, 2018, now U.S. Pat. No. 10,973,592, which is a Continuation-In Part of U.S. patent application Ser. No. 15/454,123 filed Mar. 9, 2017, now U.S. Pat. No. 10,463,438 and also claims the benefit of priority under 35 USC § 119(e) of U.S. Provisional Patent Application No. 62/583,582 filed on Nov. 9, 2017.

This application is also related to:

PCT Patent Application No. PCT/IL2015/050893 filed on Sep. 4, 2015,

PCT Patent Application No. PCT/IL2015/050892 filed on Sep. 4, 2015,

PCT Patent Application No. PCT/IL2015/050891 filed on Sep. 4, 2015,

PCT Patent Application No. PCT/IL2016/050976 filed Sep. 4, 2016 and

U.S. patent application Ser. No. 15/454,123 filed Mar. 9, 2017.

The contents of the above applications are all incorporated by reference as if fully set forth herein in their entirety.

FIELD AND BACKGROUND OF THE INVENTION

The present invention, in some embodiments thereof, relates to a control console and, more particularly, but not exclusively, to a control console including at least one control arm.

SUMMARY OF THE INVENTION

Following are examples of some embodiments of the invention. Features of one example may be combined with features of one or more other examples, unless expressly prohibited and form additional examples of some embodiments of the invention.

Example 1. A control console for control of a medical surgical device comprising at least one surgical mechanical arm, which control console comprising:

a control console base at least one user support coupled to said control console base;

a processor configured to receive data regarding a selected surgical configuration of said at least one surgical mechanical arm and at least one camera;

an input arm support coupled to said control console base;

at least one input arm comprising a plurality of sections sequentially coupled by joints, coupled to and extending from said input arm support where a direction of extension of said input arm, with respect to said at least one user support is adjustable to match an input arm configuration to said selected surgical configuration, a camera view of said at least one surgical mechanical arm thereby corresponding to a user view of said input arm.

Example 2. The control console according to Example 1, comprising a user interface;

wherein said processor is configured to receive at least a portion of said data from said user interface.

Example 3. The control console according to any one of Examples 1-2, comprising a user interface; wherein said user interface is configured to display an indication of a selected surgical configuration.

Example 4. The control console according to any one of Examples 1-3, comprising a user interface display configured to display images collected by said camera.

Example 5. The control console according to any one of Examples 1-4, wherein said data comprises one or more of, a direction of insertion of said at least one surgical mechanical arm, a direction of insertion of said camera, a region of insertion of said at least one surgical mechanical arm, a region of insertion of said camera.

Example 6. The control console according to any one of Examples 1-5, wherein said processor is configured to receive at least a portion of said data from at least one control console sensor.

Example 7. The control console according to Example 6, wherein said at least one control console sensor is configured to send a signal to said processor based on said direction of extension of said input arm from said input arm support.

Example 8. The control console according to Example 7, wherein said processor is configured to:

compare said signal to said data; and generate an alarm upon identifying a discrepancy between a selected surgical configuration and said direction of extension of said input arm.

Example 9. The control console according to any one of Examples 7-8, wherein said processor is configured to:

compare said signal to said data; and generate a signal disabling one or more actuator configured to control movement of said surgical mechanical upon identifying a discrepancy between a selected surgical configuration and said direction of extension of said input arm.

Example 10. The control console according to any one of Examples 1-9, wherein said processor is configured to receive at least a portion of said data from said at least one surgical mechanical arm.

Example 11. The control console according to any one of Examples 1-10, wherein said processor is configured to receive at least a portion of said data from said camera.

Example 12. The control console according to any one of Examples 1-11, wherein a separation between said at least one input arm and said at least one user support is adjustable.

Example 13. The control console according to any one of Examples 1-12, wherein said at least one support comprises a user seat.

Example 14. The control console according to any one of Examples 1-13, wherein said at least one support comprises at least one user arm rest.

Example 15. The control console according to any one of Examples 1-14, comprising a first and a second input arm, according to said at least one input arm.

Example 16. The control console according to any one of Examples 1-15, comprising at least one sensor configured to generate an input arm signal based on a measured angle between two of said input arm sections;

wherein said a processor is configured to:

receive said input arm signal;

generate a control signal instructing movement of said at least one surgical mechanical arm, based on said input arm signal;

send said control signal to said surgical mechanical arm.

Example 17. A system comprising:

a control console according to any one of Examples 1-16;

at least one surgical mechanical arm;

at least one camera;

at least one sensor configured to measure one or more of:

a position of said surgical mechanical arm with respect to a position of said camera;

a location of insertion into a patient of said surgical mechanical arm with respect to a location of insertion into a patient of said camera;

a direction of insertion into a patient of said surgical mechanical arm with respect to a direction of insertion into a patient of said camera.

Example 18. A surgical method comprising:

selecting a surgical approach for at least one surgical mechanical arm and a laparoscopic camera; and adjusting a direction of extension of an input arm from an input arm support to correspond to said surgical approach;

controlling movement of said surgical mechanical arm using measured movement of said input arm.

Example 19. The surgical method according to Example 18, wherein said selecting comprises:

selecting a camera insertion direction of a laparoscopic camera into a patient;

selecting an arm insertion direction of a surgical mechanical arm into said patient;

wherein said adjusting comprises:

adjusting a direction of extension of an input arm from an input arm support with respect to a user support, where:

when said camera insertion direction is away from said arm insertion direction said input arm extends away from said user support;

when said camera insertion direction is towards from said arm insertion direction said input arm extends towards said user support.

Example 20. The method according to Example 19, wherein said adjusting comprises adjusting a vertical angle of said direction of extension of said input arm to correspond to said angle of insertion of said surgical mechanical arm with respect to an angle of insertion of said laparoscopic camera.

Example 21. The method according to any one of Examples 19-20, wherein said adjusting comprises adjusting a horizontal angle of said direction of extension of said input arm to correspond to said angle of insertion of said surgical mechanical arm with respect to an angle of insertion of said laparoscopic camera.

Example 22. The method according to any one of Examples 19-21, wherein adjusting comprises adjusting a separation between attachment of said user support and said input arm support, to maintain a separation between a volume of allowable positions of said input arm and said user support.

Example 23. The surgical method according to Example 18, wherein said selecting comprises: selecting a camera insertion location of a laparoscopic camera into a patient;

selecting an arm insertion location of a surgical mechanical arm into said patient;

wherein said adjusting comprises:

comparing a separation between said camera insertion location and an arm insertion location with a threshold;

adjusting a direction of extension of an input arm from an input arm support with respect to a user support, where:

when said separation is below said threshold said input arm extends away from said user support;

when said separation is below said threshold extends towards said user support.

Example 24. A control console for control of a medical surgical device comprising at least one surgical mechanical arm, which control console comprising:

an elongate control console base sized and shaped for a user to comfortably sit astride said control console base;

at least one input arm coupled to said control console base and comprising a plurality of sections sequentially coupled by joints;

at least one sensor configured to measure user controlled movement of said sections; and circuitry configured to receive a measurement signal from said sensor and to generate a control signal, based on said measurement signal for control of movement of said surgical mechanical arm.

Example 25. The control console according to Example 24, wherein said elongate base is 5-30 cm wide.

Example 26. The control console according to any one of Examples 24-25, wherein said elongate base is 0.5-2 m long.

Example 27. The control console according to any one of Examples 24-26, comprising a seat coupled to said base.

Example 28. The control console according to Example 27, wherein a position of said seat is adjustable with respect to said base.

Example 29. The control console according to any one of Examples 27-28, wherein a separation between said at least one input arm and said seat is adjustable.

Example 30. The control console according to any one of Examples 24-29, comprising one or more arm rest coupled to said base.

Example 31. The control console according to any one of Examples 24-29, comprising two input arms according to said input arm.

Example 32. The control console according to any one of Examples 24-31, wherein a footprint of said control console is elongate.

Example 33. A surgical method comprising:

providing a surgical mechanical arm comprising:

an elongate support portion;

a first bendable portion coupled to said elongate support portion;

a second bendable portion coupled to said first bendable portion;

a tool coupled to said second bendable portion:

positioning said surgical mechanical arm at a surgical site;

identifying a potential collision between said surgical mechanical arm and an obstacle, bending said surgical mechanical arm at said second bendable portion; and bending said surgical mechanical arm at said first bendable portion.

Example 34. The method according to Example 33, wherein said identifying comprises: identifying, using a processor, based on data received from one or more sensor.

Example 35. The method according to Example 34, wherein said one or more sensor includes a camera configured to collect images including said obstacle and at least a portion of said surgical mechanical arm.

Example 36. The method according to any one of Examples 33-35, wherein said obstacle is an inner abdominal wall.

Example 37. The method according to Example 36 wherein said obstacle is an inner abdominal wall of an insufflated patient.

Example 38. A surgical system for control of a surgical mechanical arm, which system comprises:

at least one input arm comprising:
- a first section rotatable about a first section axis;
- a second section rotatable about a second section axis;
- a first bendable joint coupling said first and said second sections, where said first section axis and said second section axis are not collinear, for all angles of bending of said first bendable joint;
- at least one sensor configured to measure movement of one or more of said sections; and
- circuitry configured to receive a measurement signal from said at least one sensor and to generate a control signal, based on said measurement signal for control of movement of said surgical mechanical arm.

Example 39. The surgical system of Example 38, wherein said where bending at said bendable joint changes an angle of said first section axis with respect to said second section axis.

Example 40. The surgical system of Example 38, wherein said first section is rotatable at a first rotational joint.

Example 41. The surgical system of Example 40, wherein said first rotational joint couples said first section to a support section.

Example 42. The surgical system of Example 41, wherein said first rotational joint couples a proximal portion of said first section to said support section.

Example 43. The surgical system of Example 42, wherein said bendable joint couples a distal portion of said first portion to a proximal portion of said second section.

Example 44. The surgical system of Example 38, wherein said second section is rotatable at a second rotational joint.

Example 45. The surgical system of Example 38, wherein when said input arm is in a straight configuration, said first axis and said second axis are parallel.

Example 46. The surgical system of Example 45, wherein, when said input arm is in said straight configuration, there is an offset between said first and said second axes.

Example 47. The surgical system of Example 46, wherein said offset is 0.01-5%, of a maximum portion cross sectional thickness.

Example 48. The surgical system of Example 46 wherein said offset is 1-5 mm.

Example 49. The surgical system according to Example 38, wherein said axes of rotation of said rotational joints are at different separations from an axis of flexion of a flexion joint disposed between said rotational joints.

Example 50. The surgical system according to Example 38, where a difference in separation between said first axis and said second axis as measured at an axis of flexion of said bendable joint is 0.005-5% of a portion thickness.

Example 51. The surgical system according to Example 38, where a difference in separation between said first axis and said second axis as measured at an axis of flexion of said bendable joint is 1-5 mm.

Example 52. The surgical system according to Example 38, wherein said bendable joint is a pivot joint.

Example 53. The surgical system according to Example 50, wherein said bendable joint is a pivot joint and said axis of flexion is an axis of said pivot joint.

Example 54. The surgical system according to Example 38, wherein said at least one sensor comprises a magnetic sensor connected configured to measure movement of a magnet mounted to one of said sections.

Example 55. The surgical system according to Example 38, wherein said at least one sensor comprises:
- a first sensor configured to measure rotation of said first section; and
- a second sensor configured to measure rotation of said second section.

Example 56. The surgical system according to Example 55, wherein said first sensor is a magnetic sensor configured to configured to measure movement of a magnet configured to rotate with said first section;

wherein said second sensor is a magnetic sensor configured to configured to measure movement of a magnet configured to rotate with said second section.

Example 57. The surgical system of Example 38, wherein said bendable joint is bendable by at least 120°.

Example 58. The surgical system of Example 38, wherein said bendable joint is bendable by at least 180°.

Example 59. The surgical system of Example 44, wherein said second section is coupled at a distal end to a handle by second bendable joint.

Example 60. The surgical system of Example 59, wherein said second section rotatable with respect to said handle about said second rotational joint.

Example 61. A method of surgical device control comprising:
- providing an input arm including a first portion rotatable about a first rotational joint coupled, by a bendable joint, to a second portion rotatable by a second rotational joint;
- applying a torque to said first rotatable portion of an input arm to rotate sais first rotatable portion about an axis of rotation of said first rotational joint, where torque transferred to said second rotatable portion is reduced by transfer and is not sufficient to overcome friction at said second rotational joint and rotate said second rotatable portion.

Example 62. The method of Example 61, wherein said axis of rotation of said first portion and an axis of rotation of said second rotational joint is non-coaxial with said axis of said first rotational joint reducing said torque transferred to said second rotatable.

Example 63. A surgical system comprising:
- a surgical mechanical arm comprising a plurality of sections sequentially coupled by joints;
- an input device for control of a surgical mechanical arm comprising:
  - a plurality of sections sequentially coupled by input arm joints, where said plurality of sections includes a handle;
  - at least one sensor configured to measure user controlled movement of said sections;
  - a user interface disposed on said handle whereby an orientation of said user interface moves under friction between a user and the user interface, as a user moves the handle; and
- circuitry configured to receive a measurement signal from said sensor and to generate a control signal, based on said measurement signal for control of movement of said surgical mechanical arm.

Example 64. The surgical system according to Example 1, comprising at least one actuator configured to:
- receive said control signal; and
- move at least one of said surgical arm sections, based on said control signal.

Example 65. The surgical system according to any one of Examples 63-64, comprising circuitry configured to receive a signal from said user interface and to generate a user interface control signal, based on said signal received from said user interface.

Example 66. The surgical system according to Example 65, comprising at least one actuator configured to:

receive said user interface control signal; and move at least one of said surgical arm sections, based on said control signal.

Example 67. The surgical system according to Example 66, wherein said surgical mechanical arm comprises a surgical tool;

wherein said actuator actuates said surgical tool.

Example 68. The surgical system according to Example 67, wherein said surgical tool is connected to a distal end of said surgical mechanical arm.

Example 69. The surgical system according to any one of Examples 63-68, wherein said user interface is a switch.

Example 70. The surgical system according to Example 69, wherein said user interface is biased in an open position.

Example 71. The surgical system according to any one of Examples 63-70, wherein friction between said user interface and a user's hand, when a user is touching the user interface is sufficient to change an orientation of said user interface as the user moves said handle.

Example 72. A method of surgical device control comprising:

changing an orientation of a handle of an input device with respect to a user hand;

adjusting an orientation of a user interface with respect to said handle to maintain an orientation of a user interface disposed on said handle with respect to said user hand.

Example 73. The method according to Example 72, wherein said adjusting comprises moving said user interface under friction between at least a portion of said user interface and a portion of a user's hand.

Example 74. A surgical system comprising:

a surgical mechanical arm comprising a plurality of surgical arm sections sequentially coupled by surgical arm joints;

an input arm comprising:

a plurality of input arm sections sequentially coupled by input arm joints; and an elongate handle, coupled to a distal end of said input arm and comprising:

a rotatable body of said handle; and a user interface coupled to said body;

at least one sensor configured to measure rotation of said rotatable portion;

wherein a processor configured to receive a measurement signal from said sensor and a user interface signal from said user interface generates a control signal, based on said measurement signal and said user interface signal, instructing control of rotation of a surgical arm section.

Example 75. The surgical system according to Example 74, wherein said user interface is a second rotatable portion, rotatable with respect to said handle.

Example 76. The surgical system according to Example 75, wherein said user interface is a dial coupled to said handle and rotatable with respect to said handle.

Example 77. The surgical system according to Example 76, wherein said dial is disposed on an end of said handle coupled to said input arm.

Example 78. The surgical system according to Example 74, wherein said rotatable portion is an elongate body of said handle, rotatable about a long axis of said elongate body.

Example 79. The surgical system according to any one of Examples 74-78, wherein said at least one sensor comprises a magnetic sensor configured to measure movement of a magnet configured to rotate with said rotatable portion.

Example 80. The surgical system according to Example 75, wherein said at least one sensor comprises:

a first sensor configured to measure rotation of said rotatable portion; and a second sensor configured to measure rotation of said second rotational portion.

Example 81. The surgical system according to Example 80, wherein said first sensor is a magnetic sensor configured to configured to measure movement of a magnet configured to rotate with said rotatable portion;

wherein said second sensor is a magnetic sensor configured to configured to measure movement of a magnet configured to rotate with said second rotatable portion.

Example 82. A surgical system for control of a surgical mechanical arm, which system comprises:

at least one input arm comprising:

a plurality of sections;

a plurality of joints sequentially coupling said plurality of sections;

at least one sensor configured to measure movement of one or more of said sections; and a weight attached to one of said plurality of sections which biases said one of said plurality of sections to a null configuration, by movement under gravity of said one of said plurality of sections about one or more of said joints; and circuitry configured to receive a measurement signal from said at least one sensor and to generate a control signal, based on said measurement signal for control of movement of said surgical mechanical arm.

Example 83. The surgical system of Example 82, wherein said weight is sufficient to overcome friction of movement of said section about one or more joint coupling said section to one or more adjacent section.

Example 84. The surgical system according to any one of Examples 82-83, wherein said joints include one or more rotational joint.

Example 85. The surgical system according to Example 84, wherein said weight is coupled to a section which rotates about a rotational joint;

wherein said section rotates about said rotational joint to return to said section to said null configuration.

Example 86. The surgical system according to Example 85, wherein said section is coupled to a flexion joint.

Example 87. The surgical system according to Example 86, wherein said flexion joint is bendable in a single bending plane.

Example 88. The surgical system according to any one of Examples 86-87, wherein said at least one sensor is configured to measure an angle at said flexion joint, where said angle is an angle between adjacent sections connected by said joint.

Example 89. The surgical system according to Example 87, wherein said flexion joint is bendable in one rotational direction about said single bending plane from a straight configuration.

Example 90. The surgical system according to Example 89, wherein said plurality of sections are coupled to a support.

Example 91. The surgical system according to Example 90, wherein said weight biases said flexion joint such that an axis of said flexion joint is above a top of said support.

Example 92. The surgical system according to Example 91, wherein said weight biases said flexion joint in an orientation where bending at said flexion joint, by less than 90°, about said single bending plane from a straight configuration in said rotational direction moves a section distal and adjacent to said flexion joint away from said support.

Example 93. The surgical system according to any one of Examples 90-92, wherein said weight biases said flexion joint such that said rotational direction is in a generally upwards direction.

Example 94. The surgical system according to any one of Examples 85-93, wherein a weight is coupled to an input section adjacent to each said rotational joint.

Example 95. The surgical system according to any one of Examples 82-94, wherein said input arm sections are alternatively coupled by rotational and flexion joints.

Example 96. The surgical system according to Example 95, wherein said flexion joints are bendable in a single bending plane.

Example 97. The surgical system according to Example 96, wherein said flexion joints are bendable in one rotational direction about said single bending plane from a straight configuration.

Example 98. The surgical system according to any one of Examples 95-97, wherein one or more of said flexion joints include ball bearings.

Example 99. The surgical system according to any one of Examples 95-97, wherein one or more of said rotational joints include ball bearings.

Example 100. The surgical system according to Example 82-99, wherein said input arm includes a first flexion joint, a second flexion joint, a first rotational joint and a second rotational joint.

Example 101. The surgical system according to Example 100,

- wherein said first rotational joint couples a first input arm section to an input arm support;
- wherein said first flexion joint couples a second input arm section to said first input arm section;
- wherein said second rotational joint couples a third input arm section to said second input arm section;
- wherein said second flexion joint couples a fourth input arm section to said third input arm section;
- wherein a handle section is coupled to said third input arm section.

Example 102. The surgical system according to Example 101, comprising:

- a first weight coupled to said second section, said first weight configured to maintain an axial orientation of said second section.

Example 103. The surgical system according to Example 102, comprising:

- a second weight coupled to said fourth section, said second weight configured to maintain an axial orientation of said fourth section.

Example 104. The surgical system of Example 97, wherein said flexion joints are pivot joints.

Example 105. The surgical system of Example 97, wherein one or more of said flexion joints are bendable by at least 120°.

Example 106. The surgical system of Example 97, wherein one or more of said flexion joints are bendable by at least 180°.

Example 107. The surgical system of Example 97, wherein each of said flexion joints are bendable by at least 120°.

Example 108. The surgical system of Example 97, wherein each of said flexion joints are bendable by at least 180°.

Example 109. A surgical system comprising:

- a surgical mechanical arm comprising a plurality of surgical arm sections sequentially coupled by surgical arm joints;
- an input arm comprising:
  - a plurality of input arm sections sequentially coupled by input arm joints; and
  - an elongate handle:
    - sized and shaped to be held between a human adult's thumb and one or more finger, where a maximum dimension of said handle perpendicular to a handle long axis is 5 mm-15 mm and a long axis length of said handle is 20-200 mm;
  - coupled to a distal end of said input arm by a flexion joint; and
  - extending proximally with respect to a most distal input arm section so that a user grasping said handle bends said flexion joint to hold said handle above other portions of the input arm
  - at least one sensor configured to measure movement of one or more of said sections; and
  - circuitry configured to receive a measurement signal from said at least one sensor and to generate a control signal, based on said measurement signal for control of movement of said surgical mechanical arm.

Example 110. The surgical system of Example 109, where one or more of said plurality of sections are sized such that a user holding said elongate handle is able to support one or more section with the user's palm of the hand holding the handle.

Example 111. The surgical system of Example 110, wherein a portion of said input arm includes a protrusion which protrudes from a body of said input arm, said protrusion at a distance from said handle and sized and shaped to be held in a user's palm of a hand holding the handle.

Example 112. The surgical system of Example 111, wherein said protrusion is at least a portion of a flexion joint.

Example 113. The surgical system according to Example 109, wherein said input arms sections are alternatively coupled by rotational and flexion joints.

Example 114. The surgical system according to Example 113, wherein said flexion joints are bendable in a single bending plane.

Example 115. The surgical system according to Example 114, wherein one or more of said flexion joints is bendable by at least 120°.

Example 116. The surgical system according to Example 114, wherein one or more of said flexion joints is bendable by at least 180°.

Example 117. The surgical system according to Example 116, wherein said flexion joints are bendable in one rotational direction about said single bending plane from a straight configuration.

Example 118. The surgical system according to any one of Examples 109-117, wherein said input arm includes a first flexion joint, a second flexion joint, a first rotational joint and a second rotational joint.

Example 119. The surgical system according to Example 118, wherein said flexion joints are each bendable by at least 120°.

Example 120. The surgical system according to any one of Examples 109-119, wherein said handle extends proximally with respect to a most distal input arm section.

Example 121. The surgical system according to any one of Examples 109-120, wherein said handle extends towards a most distal input arm joint.

Example 122. The surgical system according to Example 121, wherein said most distal input arm joint is a flexion joint.

Example 123. The surgical system according to any one of Examples 109-122, wherein a long axis length of said handle is 30-100% of a maximum length of said input arm.

Example 124. The surgical system according to any one of Examples 109-123, wherein said handle comprises:

a rotatable portion;

at least one sensor configured to measure rotation of said rotatable portion;

wherein a processor configured to receive a measurement signal from said sensor generates a control signal, based on said measurement signal, instructing control of rotation of a surgical arm section.

Example 125. The surgical system according to Example 124, wherein said rotatable portion is a dial coupled to said handle and rotatable with respect to said handle.

Example 126. The surgical system according to Example 125, wherein said dial is disposed on an end of said handle coupled to said input arm.

Example 127. The surgical system according to Example 124, wherein said rotatable portion is an elongate body of said handle, rotatable about a long axis of said elongate body.

Example 128. The surgical system according to Example 124, wherein said handle comprises a second rotatable portion;

wherein said at least one sensor is configured to measure rotation of said second rotatable portion.

Example 129. The surgical system according to Example 128, wherein said first rotatable portion is a dial coupled to said handle and rotatable with respect to said handle; and wherein said second rotatable portion an elongate body of said handle, rotatable about a long axis of said elongate body.

Example 130. The surgical system according to any one of Examples 128-129, wherein said at least one sensor comprises:

a first sensor configured to measure rotation of said first rotatable portion; and a second sensor configured to measure rotation of said second rotatable portion.

Example 131. A control console for control of a medical surgical device comprising:

a control console base;

a seat attached to said control console base;

an input arm attached to said control console base comprising:

a support coupled to said control console base;

a proximal end coupled to said support;

a distal end;

a handle section;

a plurality of sections sequentially coupled by input arm joints, extending from said proximal end where said plurality of sections terminates at said distal end with said handle section;

an armrest attached to said control console base;

a first volume of possible positions of said handle section said first volume defined by lengths of said sections and;

a second volume of user hand positions when a user sitting at said seat resting a forearm of said user on said armrest, said second volume defined by a position of said armrest and by a size of said user arm;

wherein said first volume is contained by said second volume, for average human adult arm dimensions.

Example 132. The control console according to Example 131, wherein said handle extends proximally with respect to a most distal input arm section.

Example 133. The control console according to any one of Examples 131-132, wherein said handle extends towards a most distal input arm joint.

Example 134. The control console according to any one of Examples 131-133, wherein a long axis length of said handle is 30-100% of a maximum length of said input arm.

Example 135. The control console according to any one of Examples 131-134, wherein said first volume is a portion of a sphere.

Example 136. The control console according to Example 135, wherein said sphere is of 200-500 mm diameter.

Example 137. The control console according to any one of Examples 131-136, wherein said second volume is a volume of human adult hand positions.

Example 138. The control console according to any of Examples 131-137, comprising a first input arm and a second input arm coupled to said control base according to said input arm, said first volume of said first input arm contained by a second volume of a first user hand, said first volume of said second input arm contained by a second volume of a second user hand.

Example 139. The control console according to Example 138, comprising a first armrest and a second armrest;

wherein said second volume of said first user hand is defined by a position of said first armrest; and wherein said second volume of said second user hand is defined by a position of said second armrest.

Example 140. The control console according to any one of Examples 131-139, wherein said input arms sections are alternatively coupled by rotational and flexion joints.

Example 141. The control console according to Example 140, wherein said flexion joints are bendable in a single bending plane.

Example 142. The control console according to Example 141, wherein said flexion joints are bendable in one rotational direction about said single bending plane from a straight configuration.

Example 143. The control console according to any one of Examples 131-142, wherein said input arm includes a first flexion joint, a second flexion joint, a first rotational joint and a second rotational joint.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
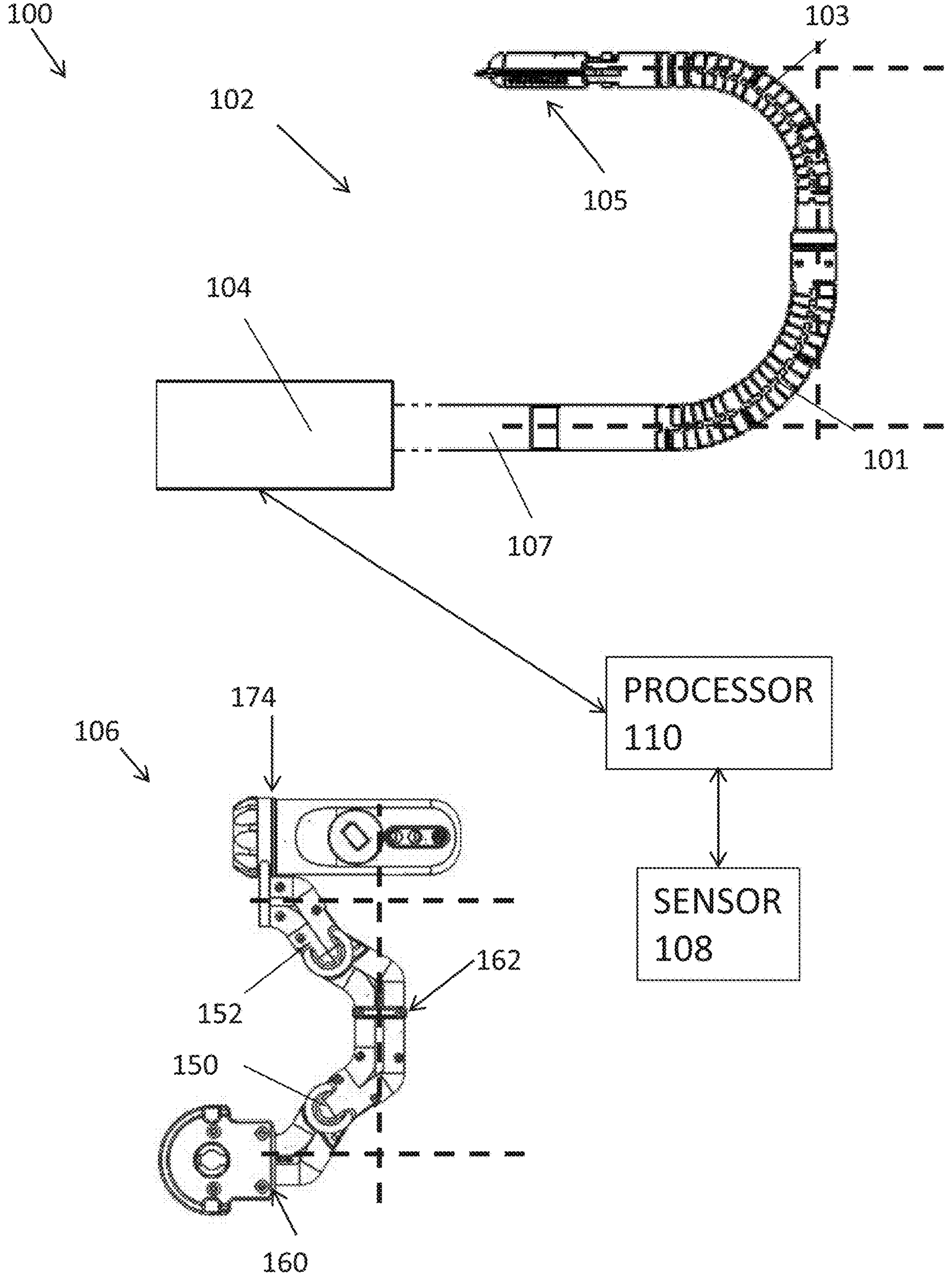
FIG. 1 is a simplified schematic of a surgical system, according to some embodiments of the invention.

The present invention, in some embodiments thereof, relates to a control console and, more particularly, but not exclusively, to a control console including at least one control arm.

Overview

A broad aspect of some embodiments of the invention relates to a mobile control console including at least one input arm for control of a surgical system including at least one surgical device. In some embodiments, at least one surgical device is a surgical mechanical arm where movement of the surgical mechanical arm is controlled by measured movement of the input arm.

In some embodiments, the control console is configured to be easily positioned and/or repositioned by a user before and/or during a surgery. In some embodiments, user control of the system, for example, at a control console, is mechanically decoupled from the surgical instrument.

In some embodiments, a control console has an elongate footprint, for example, with a footprint aspect ratio of 1:1.1-1:20, or 1:1.1-1:5, or 1:1-1:3, or lower or higher or intermediate ranges or aspect ratios. In some embodiments, a control console base to which one or more input arm and/or one or more user support are attached (e.g. base) is elongate, e.g. with an aspect ratio of 1:1.1-1:20, or 1:1.1-1:5, or 1:1-1:3, or lower or higher or intermediate ranges or aspect ratios.

In some embodiments, the control console is configured to be sat on by a user. In some embodiments, a use sits astride a portion of the control console, for example astride a control console base. In some embodiments, one or more user support is coupled to the base and/or one or more input arm.

In some embodiments, the base is configured so that a user can move the control console with user feet e.g. while the user sits astride the control console. For example, where one or more wheel is coupled to the base where the wheels have sufficiently low friction and/or the control console is light enough for the user to move the control console. For example, in some embodiments, the control console includes one or more user support e.g. including a user seat. In some embodiments, a weight of a user seated on the control console contributes to stability of the control console e.g. potentially enabling the console to be lighter.

For example, in some embodiments, the control console is small (e.g. less than 3×2 meters, or less than 2×1 meters, or lower or higher or intermediate footprint areas or ranges of footprint areas) and/or light (e.g. weighing less than 200 kg, or less than 150 kg, or less than 100 kg, or about 80 kg, or 20-100 kg, or 60-80 kg, or about 72 kg or lower or higher or intermediate weights or ranges of weights), and/or moves under application of a small force e.g. moves under a manual force easily applied by a single user, for example, 1-50 Kgf, or 5-15 Kgf, or 7-12 Kgf, or about 10 Kgf, or lower or higher or intermediate ranges or forces In some embodiments, the control console includes one or more wheel on which the control console is configured to move.

In some embodiments, the control console is configured such that a user using the control console is able to be positioned close to the patient being treated by the at least one surgical instrument. For example, an average and/or minimum distance between one or more edge (e.g. front edge) of the control console and a center of a control console seat is 0.5-3 m, or 0.5-2 m or 0.8-1.3 m or 0.95-1.19 m or about 1 m, for example, when the control console is not sterile. In some embodiments, a distance between a side of the control console and a center of a control seat is smaller, for example, less than half the distance between a front (and/or back) edge of the control console and the seat for example, 0.1-2 m, or 0.5-1.3 m or 0.5-1 or about.

In some embodiments, one or more portion of the control console is sterile. Potentially enabling the control console to be positioned close to a patient. Where, in some embodiments, an average and/or minimum distance between one or more edge of the control console and a seat of the control console is about 0.5-200 cm, or 1-50 cm, or 1-20 cm or 1-10 cm or lower or higher or intermediate distances or ranges.

In some embodiments, the control console is sized and/or shaped such that the user is able to see at least a portion of the patient whilst using the control console. For example, in some embodiments, a maximum height of the control console (e.g. height of top of a display) above a seat of the control console is about 20-100 cm, or 20-70 cm or 30-60 cm, or 36-53 cm, or lower or higher or intermediate distances or ranges.

In some embodiments, the control console is configured (e.g. sized and/or shaped) to be positioned between a patient's legs e.g. where patient legs are spread e.g. when one or more surgical device is inserted into a patient's undercarriage (e.g. through a natural orifice e.g. vagina and/or anus).

In some embodiments, the control console is configured to be located above a patient and/or for the user to be positioned above the patient. Potentially providing a user with improved view of the patient during use of the console. In some embodiments, the control console is configured to be connected (e.g. hung from) a ceiling.

A broad aspect of some embodiments of the invention relates to an input arm, where movement of the input arm controls movement of a surgical arm and a direction of extension of the input arm from a support with respect to a user and/or user support is orientated, based on a spatial relationship between the surgical arm and a camera, where the user views images of the surgical arm collected by the camera (e.g. on a user interface). In some embodiments, the surgical arm and/or camera is inserted into a patient e.g. during laparoscopic treatment of the patient. A potential advantage of user control of a surgical arm by moving an input arm, where a user view of the input arm corresponds with a view of displayed images of the surgical arm is intuitive control of the surgical arm by the user.

In some embodiments, the direction of extension of the input arm is based on a direction of extension of the surgical mechanical arm with respect to a field of view (FOV) of the camera.

In some embodiments, the surgical mechanical arm includes a rigid portion coupled to a portion including at least one joint e.g. a plurality of joints. In some embodiments, the direction of extension of the input arm is based on an angle of the surgical arm rigid portion with respect to the camera. Where the angle of the surgical arm rigid portion is measured with respect to a direction of insertion of the camera e.g. an angle of a support of the camera and/or a center of the camera's FOV.

In some embodiments, insertion points (e.g. incision/s and/or ports) on a patient for a surgical arm and a laparoscopic camera are selected and, in some embodiments, a direction of extension of the input arm from an input arm support is orientated based on a separation between the insertion points.

Where, for example, in some embodiments, the surgical arm and camera are inserted through the same region of a patient and the surgical arm is advanced further into the patient than the camera, such that at least a portion of the surgical arm (e.g. a distal end of the surgical arm) is within the camera FOV. The input arm is adjusted to extend away from the user and/or a user support (e.g. arm rest and/or seat), in some embodiments, the camera view of the surgical arm extending away from the camera corresponds with the user's view of the input arm extending away from the user. Where extending away, in some embodiments, means that proximal portion/s of the surgical arm are in the foreground of the camera images and distal portion/s of the surgical arm are in the background of camera images, at least when the surgical arm is in a straight configuration. During control of the surgical arm using the input arm, a configuration of the input arm changes e.g. by bending of input arm joints (e.g. towards the user). As, in some embodiments, the surgical arm configuration is controlled by the input arm configuration, when the configuration of the input arm changes, in some embodiments, the user view of the input arm and camera view of the surgical arm continue to correspond.

In some embodiments, insertion into a same region of a patient is defined as where the arm and camera are inserted into a patient with a small separation between insertion points (e.g. 0-20 cm or 0-10 cm or 0-5 cm or lower or higher or intermediate distances or ranges) and/or where the arm and camera are inserted through a single port and/or through a single incision and/or through the same natural orifice (e.g. vagina, anus, mouth, esophagus, windpipe, nostril, ear canal.

In some embodiments, when the surgical arm and camera are inserted through different entry locations and/or entry locations in different regions of a patient, and the surgical arm is advanced towards the camera FOV, the input arm is adjusted to extend towards the user and/or user support. In some embodiments, the camera view of the surgical arm then extends towards the camera corresponding with the user's view of the input arm which extends towards the user.

Alternatively or additionally, in some embodiments, the direction of extension of the input arm is orientated based on an angle of entrance into the patient of the camera and/or surgical arm.

In some embodiments, the surgical arm includes a rigid support portion and, in some embodiments, a distal end of the surgical arm including one more joint is coupled to the rigid support portion (e.g. coupled to a distal end of the rigid support portion). In some embodiments, the input arm is orientated based on an angle of the support portion with respect to an angle of entrance and/or FOV (e.g. center of the FOV) of the camera.

In some embodiments, a control console includes more than one input arm, movement of which is used to control one or more surgical arms. In an exemplary embodiment, each input arm is used to control a surgical arm, e.g. in some embodiments, two surgical arms are used where one movement of each of two input arms controls one of the surgical arms.

In some embodiments, orientation of each input arm is adjusted based on insertion points and/or angles of insertion and/or angle of the support portion with respect to the camera (e.g. as described above) for the corresponding surgical arm.

In some embodiments, the input arms have two possible configurations, extending towards a user and/or user support and extending away from a user and/or user support. In some embodiments, when vectors of insertion of surgical mechanical arm/s and the camera are directed towards each other, the input arm is adjusted to extend towards the user. Conversely, in some embodiments, where the vectors of insertion are directed in the same direction or not directed towards each other, the input arm is adjusted to extend away from the user.

In some embodiments, the input arms have a range of configurations where vertical and/or horizontal angle of extension of the input arm is adjustable, based on the angle between (e.g. insertion angle) surgical mechanical arm/s and the camera.

In some embodiments, a control console and/or a system processor receives data regarding a selected surgical configuration. Data, for example, including one or more of, a number of entry port/s (e.g. for surgical mechanical arms), position of entry port/s, an angle of entry of one or more device (e.g. camera and/or surgical arm) a number of devices, data regarding which device/s are inserted through which entry port.

In some embodiments, a user selects a surgical configuration through a system user interface (e.g. control console user interface). For example, by selecting from a menu of displayed options displayed on the user interface. Alternatively or additionally, in some embodiments, a user selects a surgical configuration by orientating input arm/s. Alternatively or additionally, in some embodiments, a user selects a surgical configuration by positioning and/or inserting surgical devices.

In some embodiments, the processor receives data regarding the surgical configuration from the user interface. Alternatively or additionally, in some embodiments, a system processor receives data regarding the surgical configuration from one or more sensor. For example, one or more sensor measuring orientation of input arm/s. For example, one or more sensor measuring a separation and/or orientation of surgical devices (e.g. surgical arm/s and/or camera/s).

In some embodiments, orientation of extension of control console input arm/s is adjusted, based on the selected surgical configuration e.g. manually and/or automatically by one or more actuator receiving instructions from the processor. In some embodiments, surgical arm/s are inserted and/or orientated based on the selected surgical configuration e.g. manually and/or automatically by one or more actuator receiving instructions from the processor.

A broad aspect of some embodiments of the invention relates to input arm/s which are configured for comfortable and fatigue free manipulation by a user. Where measured movement of an input arm is used to control movement of a surgical arm, the shape of the input arm, for example, corresponding with the shape of the surgical arm.

An aspect of some embodiments of the invention relates to control of a surgical mechanical arm using measured movement of a jointed input arm, where a user manipulates the jointed input arm using hand and/or wrist movement. In some embodiments, one user arm is used to manipulate a single jointed input arm. For example, in some embodiments, the user manipulates a first input arm with their left arm and a second input arm with their right arm.

In some embodiments, a volume of possible positions of one or more portion of a jointed input arm (e.g. an input arm handle) is defined by input arm portion sizes and range of angles at each joint. In some embodiments, the input arm/s are configured so a user can move an input arm through the volume using wrist movement of a single user arm, where, for example, the user's forearm remains on an armrest.

In some embodiments, the control console is configured for comfortable user by a user, where distance between the input arms and/or between the input arms and other portions of the control console (e.g. user support/s) is selected for user comfort and/or is adjustable.

In some embodiments, positions of a plurality of input arm segments coupled by freely moving joints are controlled by a user grasping a single portion of the input arm e.g. a distal portion of the input arm which, in some embodiments, includes or is a handle.

An aspect of some embodiments of the invention relates to an input arm, including a handle sized and shaped for manipulation by a user where the user comfortably holds the handle in a tripod grasp and/or in a prismatic finger grasp (e.g. similar to grasps associated with holding an elongated writing implement e.g. pencil, pen).

In some embodiments, whilst holding the handle in a tripod grasp, a user supports a portion of the device with a user palm. A potential advantage being improved control of a position of the portion of the device supported by the palm. In some embodiments, the input device is sized and/or shaped such that portion/s supported (e.g. directly contacted) by a user palm when the user is holding the handle in a tripod and/or prismatic finger grasp and/or supporting the handle between user fingers, include a flexion joint (flexion joints also herein termed “bendable joints”).

In some embodiments, the input arm includes one or more lock, such that, when the input arm is released by a user, the input arm remains in a last user-controlled configuration before the release. In some embodiments, the input arm includes one or more sensor (e.g. contact sensor e.g. located in the input arm handle) which is used to detect if a user (e.g. a user’s hand) is in contact with the handle and/or is grasping the handle. In some embodiments, the sensor/s provides a signal, which is analyzed by a processor to assess whether the user’s hand is in contact with the handle and/or is grasping the handle (e.g. by comparing the sensor signal/s with threshold/s). In some embodiments, the processor, upon identifying that a user has released the handle, sends one or more signal to the input arm instructing lock/s (e.g. which in some embodiments include motors within the input device) to hold and/or lock the input arm in the last position before user release. In some embodiments, sensor signals are analyzed by the processor (e.g. continuously and/or periodically) to identify resumption of contact and/or grasp (grasp, in some embodiments, corresponding to higher sensor values than contact which can be identified, e.g. by comparison with a threshold). Where, in some embodiments, upon identifying resumption of contact, the processor sends control signal/s to the lock/s to release so that the user can resume moving the input device to control the surgical device.

A broad aspect of some embodiments of the invention relates to an input arm where a user is able to control movement of the arm at joints independently.

An aspect of some embodiments of the invention relates to biasing of an input arm into one or more configuration. In some embodiments, biasing is by one or more weights, attached to one or more portion of the input arm. In some embodiments, a weight is attached to one or more input arm portion. In some embodiments, the weight is configured to return the input arm portion to which it is attached (e.g. under gravity) to a null configuration. In some embodiments, a portion to which the weight is attached is coupled to another input arm portion by a rotational joint. In some embodiments, a weight is coupled to a portion distal of a rotational joint. For example, in some embodiments, (e.g. when the input arm includes a first and a second rotational joint) a weight is attached to a portion distal of a first rotational joint and a portion distal of a second rotational joint. In some embodiments, a weight is 10 g-1 kg, or 20 g-400 g, or 50 g-100 g, or lower or higher or intermediate weights or ranges. In some embodiments, a weight is 0.1-10 times, or 0.1-0.5 times, or 0.1-5 times, or 1-5 times, or lower or higher or intermediate multiples of a weight of a section to which it is attached and/or a total weight of the input arm.

In some embodiments, weight/s return the input arm to a straight configuration (e.g. where rotational axes are parallel) upon release of the input arm. In some embodiments, weight/s mean that rotation of one portion does not result in rotation of a weighted portion of the input arm.

In some embodiments, a mass of a weight is selected to provide sufficient torque to overcome friction (e.g. at a rotational joint) to rotate a portion of the input arm to which it is attached. In some embodiments, a mass of one or more weights is selected to lower a center of gravity of one or more portion of the input arm below a central long axis of the input arm (e.g. in a straight configuration) and/or one or more portion of the input arm.

In some embodiments, weight/s are configured to return one or more portion of input arm, upon release, to a null position e.g. under gravity. In some embodiments, weights are selected to bias the input arm without increasing weight of the input arm to a level where a user manipulating the arm is fatigued easily.

Potentially, weighting of the input arm improves user ability to control rotational joints individually. For example, in some embodiments, (e.g. when a portion of the arm between the rotational joints is in a straight configuration) rotation of one rotational joint tends to generate rotation in other rotational joint/s e.g. rotational joints proximal to the joint being rotated by a user. Potentially, weighting at the rotational joint/s prevents and/or reduces the extend of rotation of a joint due to rotation of another joint.

An aspect of some embodiments of the invention relates to and input arm which includes more than one rotational joint where the joints have different axes of rotation when the arm is in a straight configuration. In some embodiments, a bendable joint (e.g. pivot joint) connect the rotational joints, for example the input arm including a first rotatable section coupled to a second rotatable section by a bendable joint. In some embodiments, axes of rotation of the rotational joints have a different separation from an axis of a flexion joint disposed between the rotational joints. In some embodiments, the axes of the rotational joints are parallel and axially offset from each other, in at least one direction, when the arm is in a straight configuration. Potentially, offsetting the rotational joints improves user ability to control rotational joints individually, for example, when the user is grasping a single portion of the input device (e.g. the handle). For example in some embodiments, rotation of one rotational joint tends to generate rotation in other rotational joint/s.

In some embodiments, the axial offset and/or difference in separation between the input axes and the flexion joint therebetween is sufficiently small e.g. with respect to one or more dimension of the input arm that a shape of the input arm continues to correspond to a shape of a surgical mechanical arm controlled by the input arm. In some embodiments, the difference in separation and/or axial offset is 0.5-20 mm, or 0.5-10 mm, or 0.5-5 mm, or about 3 mm, or lower or higher or intermediate distances or ranges. In some embodiments, the difference in separation and/or axial offset is 0.01-5%, or 0.01-0.1%, about 5% or lower or higher or intermediate percentages or ranges of a maximum input arm portion thickness. In some embodiments, the difference in separation and/or axial offset is 0.005-5%, or 0.010-0.2%, about 0.015 or lower or higher or intermediate percentages or ranges of a maximum input arm length. Where, in some embodiments, the surgical mechanical arm rotational joints are coaxial when the arm is in a straight configuration and/or where axes of rotational joints have about the same separation from an axis of a flexion joint therebetween. In some embodiments, a maximum length of an input arm is 5-50 cm, or 5-30 cm, or 10-30 cm or 15-25 cm or about 19 cm. In some embodiments, a maximum and/or average input portion width (e.g. diameter of a tubular input portion) is 1-15 cm or 1-10 cm or 2-7 cm, or about 5.5 cm.

A broad aspect of some embodiments of the invention relates to an input arm where control by a user of the arm remains comfortable for a range of input arm configurations, e.g. for a range of handle orientations with respect to the user.

An aspect of some embodiments of the invention relates to an input arm where more than one signal, generated by the input arm is used to control movement of a single portion of a corresponding surgical mechanical arm. In some embodiments, measured movement of more than one portion (e.g. measurement by more than one sensor, each sensor generating a signal) of the input arm is used to control movement of a single portion of the surgical arm. In some embodiments, measured movement of a portion of the input device and a user interface (e.g. switch, button, dial) control movement of a single portion of the surgical arm. In an exemplary embodiment, both rotation of a body of an input arm handle (e.g. about a handle long axis) and an input device control rotation of a portion of the surgical arm e.g. surgical arm end effector. In some embodiments, the user interface is a rotation user interface e.g. a dial which, in some embodiments, is disposed to an end of the handle coupled to the input arm. Potentially, more than one control (e.g. at the handle) for a single movement enables comfortable user control in different input arm configurations e.g. different handle orientations.

An aspect of some embodiments of the invention relates to an input arm user input with adjustable orientation. In some embodiments, one or more input arm user interface changes orientation with movement of the input arm. In some embodiments, orientation changes due to friction between a user and the user interface. For example, in an exemplary embodiment, a handle of an input arm includes a user input, the orientation of which moves under friction between a user finger and/or thumb as the handle is moved by the user holding the handle. In some embodiments, orientation of one or more user interface changes orientation with respect to a moving input device portion under gravity (e.g. the user interface is weighted) for example, the user interface maintaining an orientation with respect to the vertical for more than one (e.g. all) configuration of the input arm. In some embodiments, one or more user interface orientation is controlled by an actuator.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Surgical System

FIG. 1 is a simplified schematic of a surgical system 100, according to some embodiments of the invention.

In some embodiments, system 100 includes a surgical mechanical arm 102. In some embodiments, surgical mechanical arm 102 includes a first flexible portion 101 coupled to a second flexible portion 103, coupled to a tool 105. In some embodiments, a distal portion of the surgical mechanical arm (e.g. including portions 101, 103, 105) is coupled to a surgical mechanical arm support 107. In some embodiments, support 107 is rigid.

In some embodiments, surgical arm 102 is actuated by a motor unit 104. In some embodiments, surgical mechanical arm 102 is supplied with electrical power e.g. for electrosurgery through motor unit 104. In some embodiments, motor unit 104 receives electrosurgical power from an electrosurgical power generator (not illustrated).

In some embodiments, system 100 includes an input arm 106. In some embodiments, input arm includes a first flexion joint 150 and a second flexion joint 152. In some embodiments, system includes one or more sensor 108 which senses position of one or more portion of input arm 106. In some embodiments, sensor/s 108 measure movement between portion/s of the input device, for example, flexion at flexion joints 150. 150 and/or rotation about rotational joint/s 160, 162, 174.

In some embodiments, system 100 includes a processor 110 which receives a signal from sensor/s 108 and generates one or more control signal. In some embodiments, processor 110 sends the generated control signal to motor unit 104 which, in some embodiments, actuates movement of surgical mechanical arm 106, based on the control signal.

In some embodiments, the processor instructs the motor unit to move the surgical mechanical arm into a configuration where a shape of the surgical arm corresponds to a shape of the input arm. For example, where the surgical device has about the same angles between corresponding segments as the input device. Where, in some embodiments, angles between segments are measured as intersections between central long axes of the arm at rotational joints. For example, as illustrated by dashed lines on FIG. 1.

Figure 2:
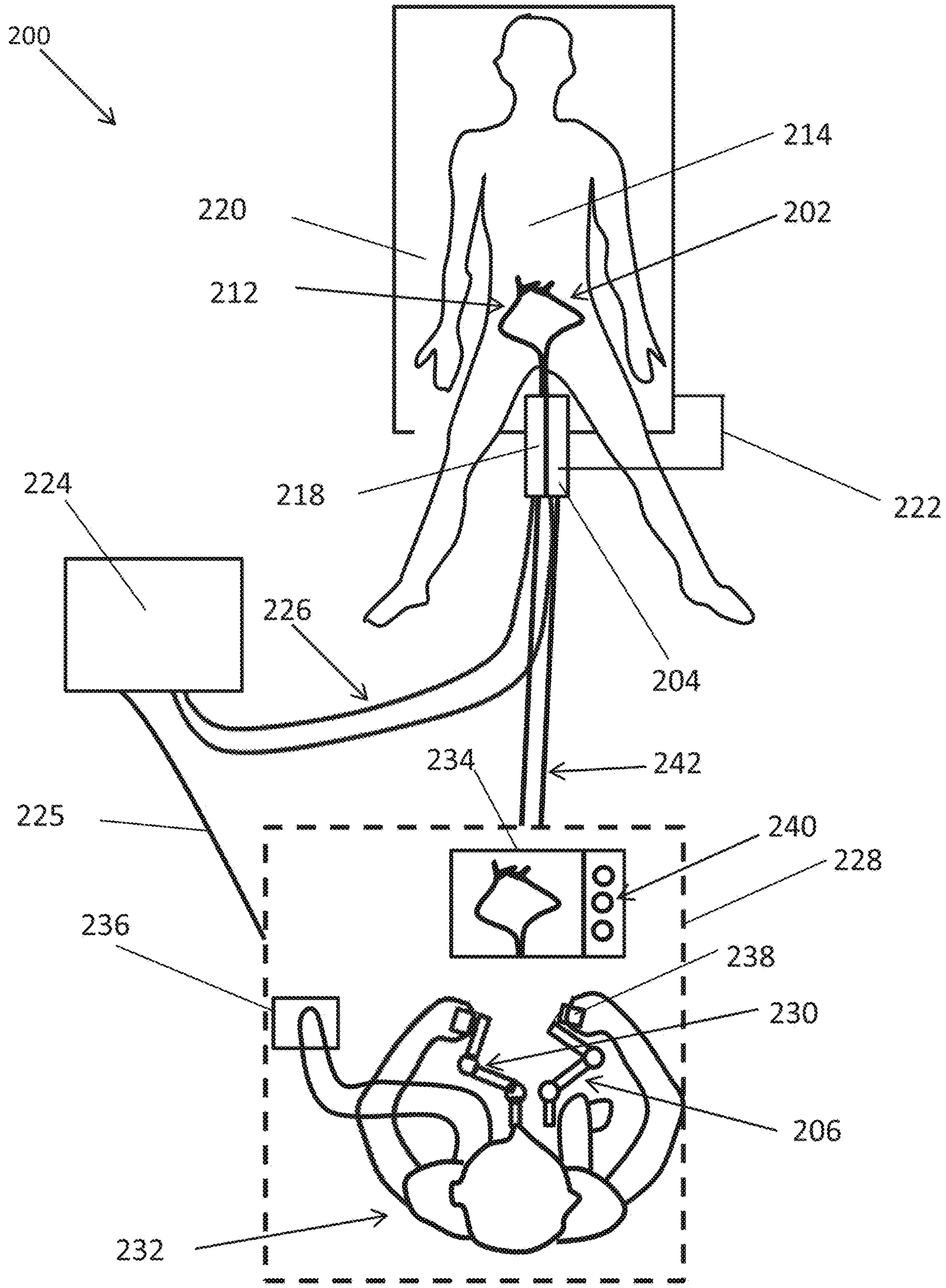
FIG. 2 is a simplified schematic of a surgical system, according to some embodiments of the invention.

FIG. 2 is a simplified schematic of a surgical system 200, according to some embodiments of the invention.

In some embodiments, surgical system 200 includes at least one surgical mechanical arm, for example, a plurality of surgical mechanical arms 202, 212 e.g. two surgical mechanical arms. In some embodiments, surgical mechanical arms are sized and/or shaped for insertion into a human patient's body 214.

In some embodiments, the system includes at least one motor unit, for example, a plurality of motor units 204, 218, where, in some embodiments, each of surgical mechanical arms 202, 204 is actuated by a motor unit. For example, where a first surgical arm 202 is actuated by a first motor unit 204 and/or a second surgical arm 212 is actuated by a second motor unit 218.

In some embodiments, one or more motor unit and/or one or more surgical arm is attached to a patient support surface 220 (e.g. a bed), for example by a support 222. In an exemplary embodiment, one or more motor unit is attached to patient support surface 220. A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

In FIG. 2, patient 214 is illustrated in a suitable position for insertion of the device into and/or through the vagina (and/or anus and/or undercarriage), where, for example, the patient's legs are apart (e.g. elevated and/or held apart e.g. held by stirrups which are not illustrated).

In some embodiments, surgical arms 202, 212 are controlled (e.g. by a user 232) at a control console 228. In some embodiments, movement of surgical arms 202, 212 is controlled. In some embodiments, electrosurgical charging of arms 202, 212 is controlled. In some embodiments, one or more motor unit (e.g. each motor unit 204, 218) is connected to control console via data and/or electrical supply connections 242. In some embodiments, control console 228 includes a plurality of user interfaces: In some embodiments, control console 228 includes one or more input arm 206, 230, where the control console is configured to generate control signals upon movement of the arm/s. For example, in some embodiments, a processor (not illustrated) generates control signals when input arm/s are moved (e.g. as described regarding sensor 108 and processor 110, FIG. 1). In some embodiments, one or more input arm includes an additional user interface (not illustrated), for example, one or more button and/or switch.

In some embodiments, control console includes a display 234. In some embodiments, display 234 is configured to display imaging of a surgical zone, for example, to display images collected by a camera inserted into patient 214 e.g. with surgical arms 202, 212. In some embodiments, display 234 is a touch screen configured to receive user input, potentially providing a user input.

In some embodiments, control console 228 includes one or more additional user interface 240 (e.g. button, switch) e.g. located on and/or near display 234.

In some embodiments, system 200 includes connectivity to and/or includes an electrosurgical generator 224. In some embodiments, for example, as known in the art of electrosurgery, electrosurgical generator 224 supplies high-frequency (e.g. radio frequency) alternating polarity electrical current. In some embodiments, electrosurgical generator 224 is configured to supply different frequencies and/or powers, for example, suitable for cutting and/or coagulating and/or desiccating and/or fulgurating tissue.

In some embodiments, electrosurgical generator 224 is a part of control console 228. Alternatively, in some embodiments, electrosurgical generator 224 is a separate device the control console and/or motor units, for example including connectivity to the electrosurgical generator. For example, in an exemplary embodiment, electrosurgical generator 224 is a Covidien Force FX ESU Electrosurgical Generator. In some embodiments, supply to the motor units is via cable/s 226 which are, for example, configured to transfer radio frequency electrosurgical power.

In some embodiments, one or more surgical mechanical arm 202, 212 is supplied with electrical power by a motor unit to which the arm is attached. In some embodiments, surgical arm/s are supplied (e.g. indirectly through motor unit/s) with power by electrosurgical generator 224.

In some embodiments, electrosurgical generator 224 includes one or more user interface e.g. for control of supply of electrosurgical power supply to arms 202, 212. In some embodiments, the electrosurgical generator is controlled by a control console user interface e.g. 234 and/or 240.

In some embodiments, control console includes a foot pedal 236. Alternatively or additionally, foot pedal 236 is provided as part of and/or attached to electrosurgical generator 224. In some embodiments, foot pedal 236 is connected via a data and/or power connection 225 to electrosurgical power generator 224. In some embodiments, foot pedal 236 controls supply of electrosurgical power to the surgical mechanical arm/s 202, 212.

In some embodiments, system 200 includes a processor (not illustrated) configured to receive signal/s from user input/s (e.g. one or more of input arm/s 206, 230, display 234, additional user interface/s 240, foot pedal 236). In some embodiments, the processor sends control signals to motor units 204, 218 and/or electrosurgical generator 224 e.g. based on signal/s received from user input/s.

In some embodiments, the processor sends control signals to control console actuator/s, for adjustment of portion/s of the control console. For example, in some embodiments, a user inputs a command through a user interface (e.g. display 234) to adjust one or more portion of the control console (e.g. position and/or orientation of input arm/s, height of a user support). In some embodiments, the processor generates a control signal, based on the user inputted command, the processor, for example, then sending the control signal to actuator/s to adjust the control console. In some embodiments, the processor generates the signal based on measurements, e.g. measured position/s and or movement/s of input arm/s. For example, in some embodiments, when input arms are moved (e.g. by a user) towards a collision, in some embodiments, a separation between the input arms is automatically increased, for example, by movement of one or more input arm support.

In some embodiments, control console 228 includes a processor. Alternatively or additionally, in some embodiments, processing is hosted by an external processor which is, for example, configured to receive user input signal/s and/or send control signals to motor unit/s and/or the electrosurgical generator.

In some embodiments, foot pedal 236 and/or electrosurgical generator 224 include a processor configured to generate control signals (e.g. based on sensed pressure of user 232 pressing on portion/s of foot pedal 236). Where, for example, electrical power supplied to motor units is varied 208, 210 based on the control signals. In some embodiments, foot pedal control signals do not pass through a control console processor.

In some embodiments, a first input arm 204 controls movement of first surgical arm 202 and/or a second input arm 230 controls movement of second surgical arm 212. In some embodiments, a user positions and/or moves an input arm 206 by grasping an input arm handle 238.

In some embodiments, a system includes an electrosurgical switching unit, for example, connected between electrosurgical generator 212 and motor units 204, 218 which, for example, switches electrosurgical power supply (e.g. on and/or off) from the electrosurgical generator, for example, upon receiving a signal (e.g. from a electrosurgical switching unit user interface and/or from an external processor).

Exemplary Control Console

Figure 3A:
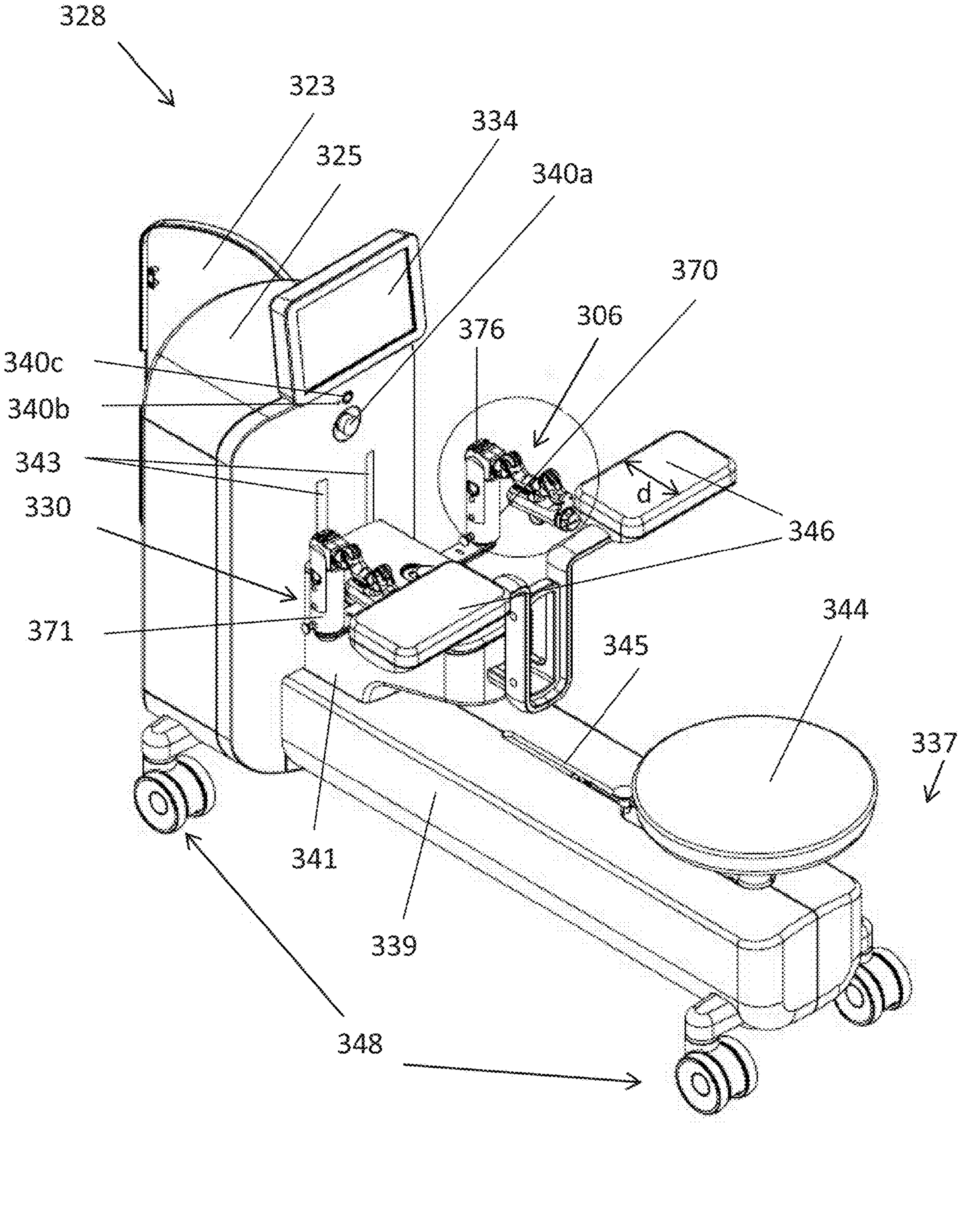
FIGS. 3A-3B are simplified schematic views of a control console, according to some embodiments of the invention.
Figure 3B:
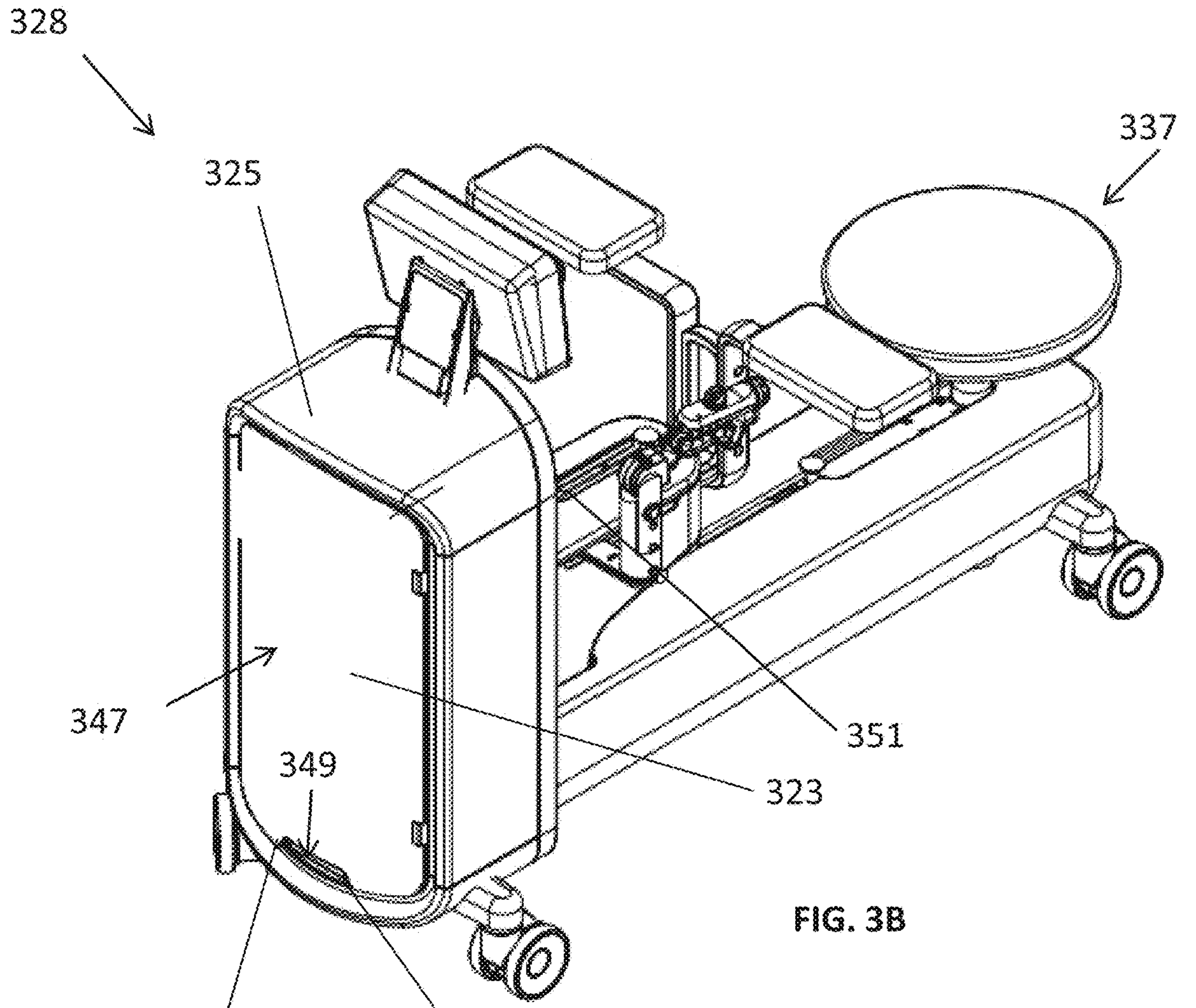

FIGS. 3A-B are simplified schematic views of a control console, according to some embodiments of the invention.

Figure 3C:
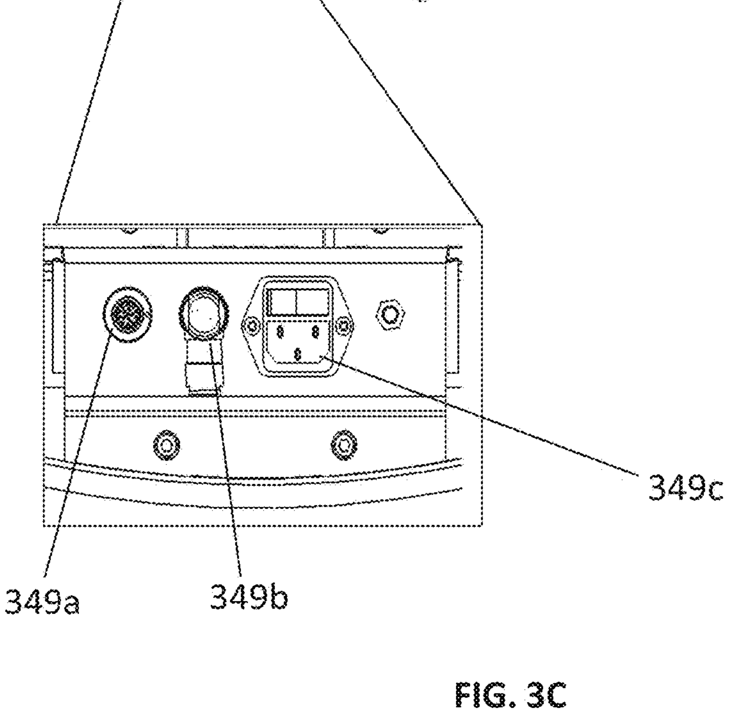
FIG. 3C is an enlarged portion of FIG. 3B according to some embodiments of the invention.

FIG. 3C is an enlarged portion of FIG. 3B according to some embodiments of the invention.

In some embodiments, control console 328 includes a first input arm 306 and a second input arm 330. In some embodiments, two input arms are used to control one, two, or more than two surgical mechanical arms. Where, for example, a user selects surgical arms for control with the surgical arms, for example, then changing and/or switching the surgical arm selection.

Alternatively, in some embodiments, control console 328 includes one input arm and/or more than two input arms, for example, 3, 1-10, 1-5 or lower or higher or intermediate numbers of input arms. In some embodiments, each input arm controls a surgical instrument (e.g. a surgical mechanical arm). In some embodiments, more than one input arm controls a surgical instrument and/or a single input arm is used to control more than one surgical instrument.

In some embodiments, movement of a camera, e.g. laparoscopic camera, is controlled by movement of an input arm. In some embodiments, a laparoscopic camera is mounted on a mechanical arm, for example, forming or replacing an end effector of a surgical mechanical arm (e.g. as described elsewhere in this document). For example, in some embodiments, a control console includes three input arms, one for control of each of a first surgical arm, a second surgical arm and a laparoscopic camera. In some embodiments, a control console includes input arms of different sizes. In some embodiments an input arm (e.g. a third input arm) is smaller than other input arm/s. For example, in some embodiments, a control console includes an input arm which is sized for control by one or more user finger and/or thumb and/or for control by a user by a single user hand, e.g. without the user needing to move their hand from contact with a handle (e.g. grip on the handle). In some embodiments, a miniature (e.g. with one or more dimension which is half that of an input arm) third input arm is mounted to one or more input arm.

In some embodiments, the control console is mobile, for example, is configured to be moved around (e.g. within an operating theatre). For example, in some embodiments, the control console is sized and/or shaped for ease of movement. For example, in some embodiments, control console 328 has less than 3×2 meters, or less than 2×1 meters, or lower or higher or intermediate footprint areas or ranges of footprint areas. For example, in some embodiments, control console weighs less than 200 kg, or less than 150 kg, or less than 100 kg, or about 80 kg, 20-100 kg, or 60-80 kg, or about 72 kg or lower or higher or intermediate weights or ranges of weights.

In some embodiments, control console 328 includes one or more wheel 348 which are, for example, mounted to base 339. In some embodiments, one or more wheel includes a lock and/or brake.

In some embodiments, an input arm is attached to control console 328 by a stand. For example, first input arm 306 is attached to control console 328 by stand 370 and second input arm 330 is attached to control console 328 by second stand 371. In some embodiments, an orientation of stand/s 370, 371 with respect to control console 328 is adjustable. For example, in some embodiments, one or both of the stands are rotatable about a stand long axis. Potentially adjustability of a stand enables a user to adjust input arm/s to desired position/s and/or orientations e.g. with respect to a user and/or user support (e.g. seat 344 and/or arm support/s 346). In some embodiments, height and/or lateral position of one or more of stand/s 370, 371 is adjustable. In some embodiments, a direction of extension of input arm 306 from stand 370/371 is adjustable e.g. to change a direction of extension of the arm with respect to a user and/or user support. For example, in some embodiments, input arm 306 is coupled to stand 370 by one or more joint (e.g. as described regarding and/or illustrated joint 376, FIG. 3D).

In some embodiments, control console 328 includes one or more user support. For example, a seat 344 and/or one or more arm support 346.

In some embodiments, position of seat 344 and/or arm supports 346 are adjustable. In some embodiments, the seat and/or arm supports have adjustable height and/or lateral position. For example, in some embodiments a base 329 of the control console includes one or more linear rail. In an exemplary embodiment, seat 344 is linearly moveable on base 339 along seat linear rail 345. In an exemplary embodiments, seat 344 is height adjustable by a spring (e.g. a gas spring) and lock where the spring urges the seat towards a maximum height and the lock, when locked, holds the seat at a selected height position.

In some embodiments, input arms 306, 330 and/or arm rests 346 are coupled to base 339 by an arm base 341. In some embodiments, arm base 341 is moveable with respect to base 339 e.g. along one or more linear rails, for example, arm base linear rails 343 for vertical movement. In some embodiments, the arm base is moveable in direction/s towards and/or away from a back end of the control console 337 and/or seat 344 (e.g. on another linear rail which is not illustrated). In some embodiments, input arm/s and/or arm rest/s are height adjustable with respect to arm base 341, for example, along linear rails (not illustrated). In some embodiments, arm/s are moveable e.g. towards and/or away from seat 344 and/or back end 337, for example, moving on linear rail/s 351 on arm base 341. In an exemplary embodiment, linear rail/s 351 for movement of input arm/s are located on an underside of arm base 341. In some embodiments, for example, alternatively or additionally to linear rails, arm rest/s and/or input arm/s include spring and lock position adjustment.

In some embodiments, a seat height (measured from a lowest point of the wheels to a top surface of the seat) is between and/or is adjustable between 200-700 mm or 390-530 mm, or lower or higher or intermediate distances or ranges.

In some embodiments, an arm support height (measured from a lowest point of the wheels to a top surface of the seat) is between and/or is adjustable between 300-1000 mm or 670-840 mm, or lower or higher or intermediate distances or ranges.

In some embodiments, a distance between arm rest supports (e.g. an arm rest "reach") is between and/or is adjustable between 50-700 mm or 151-401 mm, or lower or higher or intermediate distances or ranges.

In some embodiments, an arm rest depth, where the depth, d (FIG. 3A) is 100-200 mm or about 150 mm, or lower or higher or intermediate distances or ranges.

In some embodiments, arm rests 346 are laterally adjustable, e.g. with respect to base 329 is adjustable between 10-400 mm or 81-241, or lower or higher or intermediate distances or ranges.

In some embodiments, a seat diameter is 200-600 mm or about 380 mm, or lower or higher or intermediate distances or ranges In some embodiments, for example, in addition or alternatively to changing on orientation of input arm/s a position of one or more portion of the control console is adjustable with respect to the input arms. For example, to change a direction of extension of the arms with respect to a user and/or user support, in some embodiments, the user support/s are moved. For example, rotating portion/s of the control console around the input arm/s e.g. rotating the seat and/or arm supports e.g. around the input arm/s. In some embodiments, the control console is configured for a user to use the input arm from more than one viewing direction of the input arm. For example, in some embodiments, the control console includes more than one seat (and optionally arm rest/s associated with each seat), where the seats are at different positions around the input arm/s (e.g. one seat on each side of the input arms, e.g. disposed on a base).

In some embodiments, the control console includes a display 334, for example, for display of imaging during surgery (e.g. from a camera inserted with and/or mounted on surgical arm/s). Optionally, display 334 is a touch screen and is configured to receive user inputs. In some embodiments, the console includes additional user interface/s, for example, in some embodiments including one or more of an on/off switch 340*a*, a light indicator 340*b*, and/or off button 340*c* (e.g. emergency off button), user interface/s on the input arm/s. In some embodiments, height and/or lateral position of the display is adjustable. In some embodiments, an angle of a plane of the display e.g. with respect the control console and/or user is adjustable.

In some embodiments, control console 328 includes one or more storage compartment 325. In some embodiments, a storage compartment 325 is located behind display 334. In some embodiments, storage compartment 324 includes one or more door 323. In FIG. 3A door 323 is illustrated in an open position. In FIG. 3B, door 323 is illustrated in a closed position. In some embodiments, storage compartment 325 is sized and/or shaped to house one or more surgical mechanical arm (e.g. surgical mechanical arm 1 FIG. 1, 202, 212 FIG. 2, and/or one or more motor unit (e.g. motor unit/s 204, 218, FIG. 2).

In some embodiments, control console includes one or more power and/or data connection. For example, as described regarding connections 242 and/or 224 and/or 226 of FIG. 2. In some embodiments, the control console includes one or more socket for attachment thereto of power and/or data connections. In an exemplary embodiment, a front of control 347 console includes sockets 349. In some embodiments, FIG. 3C illustrates an enlarged view of sockets 349. In some embodiments, the control console includes a power socket 349*a*, an earth socket 349*b* and sockets for connections to motor unit/s 349*c* which include, for example, data and/or power sockets.

Exemplary Input Arm

Figure 3D:
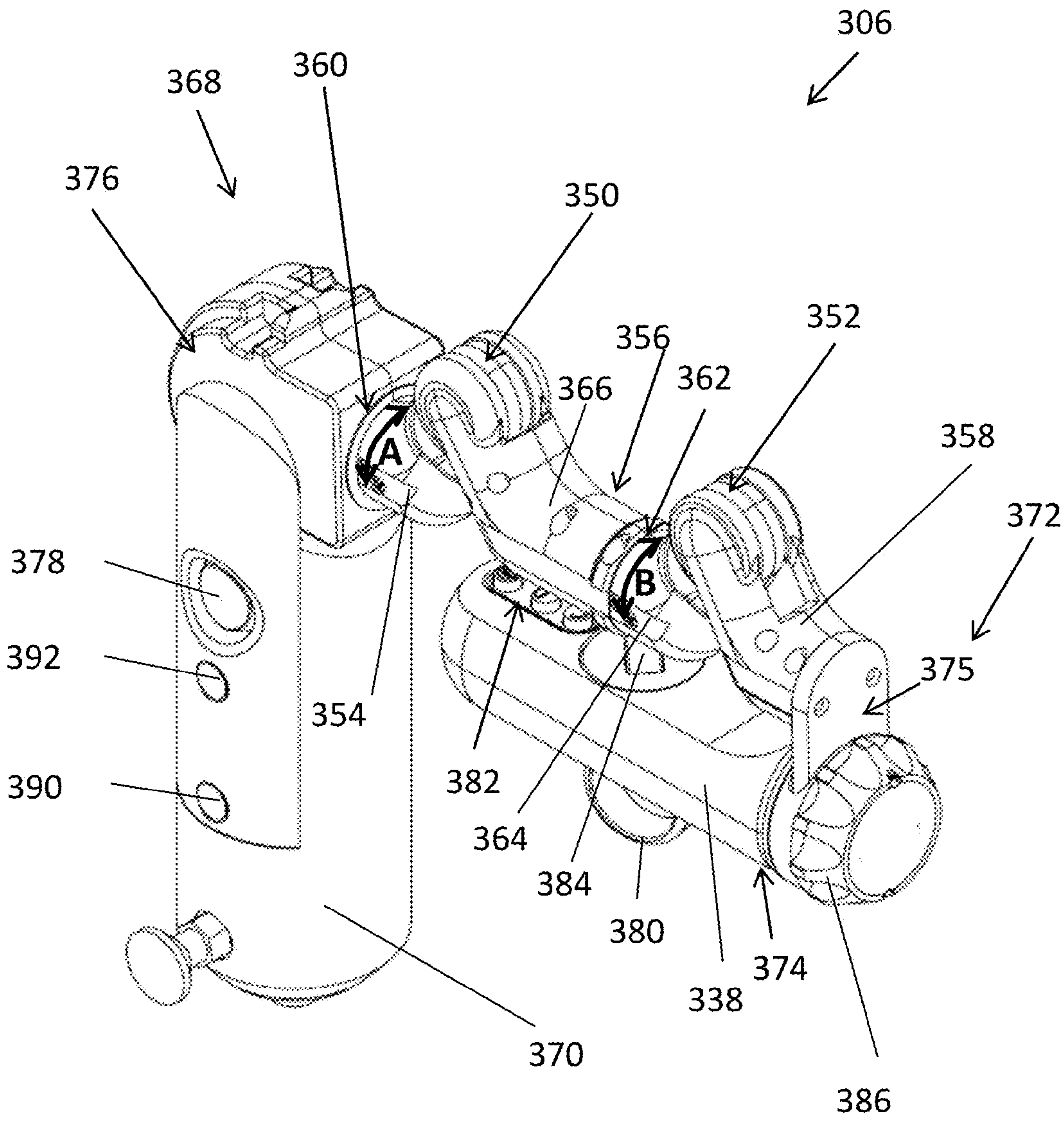
FIG. 3D is a simplified schematic side view of an input arm, according to some embodiments of the invention.

FIG. 3D is a simplified schematic side view of an input arm 306, according to some embodiments of the invention. In some embodiments, a control console includes more than one input arm, e.g. as described with respect to FIGS. 3A-B.

In some embodiments, input arm 304 includes a plurality of sections sequentially coupled by joints. In some embodiments, joints alternate between rotational joints and flexion joints. In some embodiments, input arm 304 includes a proximal end 368 coupled to a stand 370 and a distal end 372.

In some embodiments, input arm 306 is coupled to stand 370 by a stand connection joint 376. In some embodiments, stand is a pivot joint. In some embodiments, rotation of the arm about stand connection joint 376 changes an orientation of input arm 304 with respect to stand 370.

In an exemplary embodiment, input arm 304 includes a first flexion joint 350 (also termed "shoulder joint") and a second flexion joint 352 (also termed "elbow joint").

In some embodiments, the flexion joints are independently bendable (e.g. by a user). In some embodiments, one or more of flexion joints 350, 352 are pivot joints. In some embodiments, one or more of flexion joints has restricted flexion, where, for example, a shape of the input arm portions prevents flexion beyond a maximum angle. In some embodiments, one or both of flexion joints has maximal flexion of about 180°.

In an exemplary embodiment, input arm 306 includes four sections, where, for example, a first section 354 is coupled to a 376 stand connection joint 376 by a first rotational joint 360, first section 354 is coupled to a second section 366 by a first flexion joint 350, second section 366 is coupled to a third section 364 by a second rotational joint 362, and third section 364 is coupled to a fourth section 358 by a second flexion joint 352.

Figure 20:
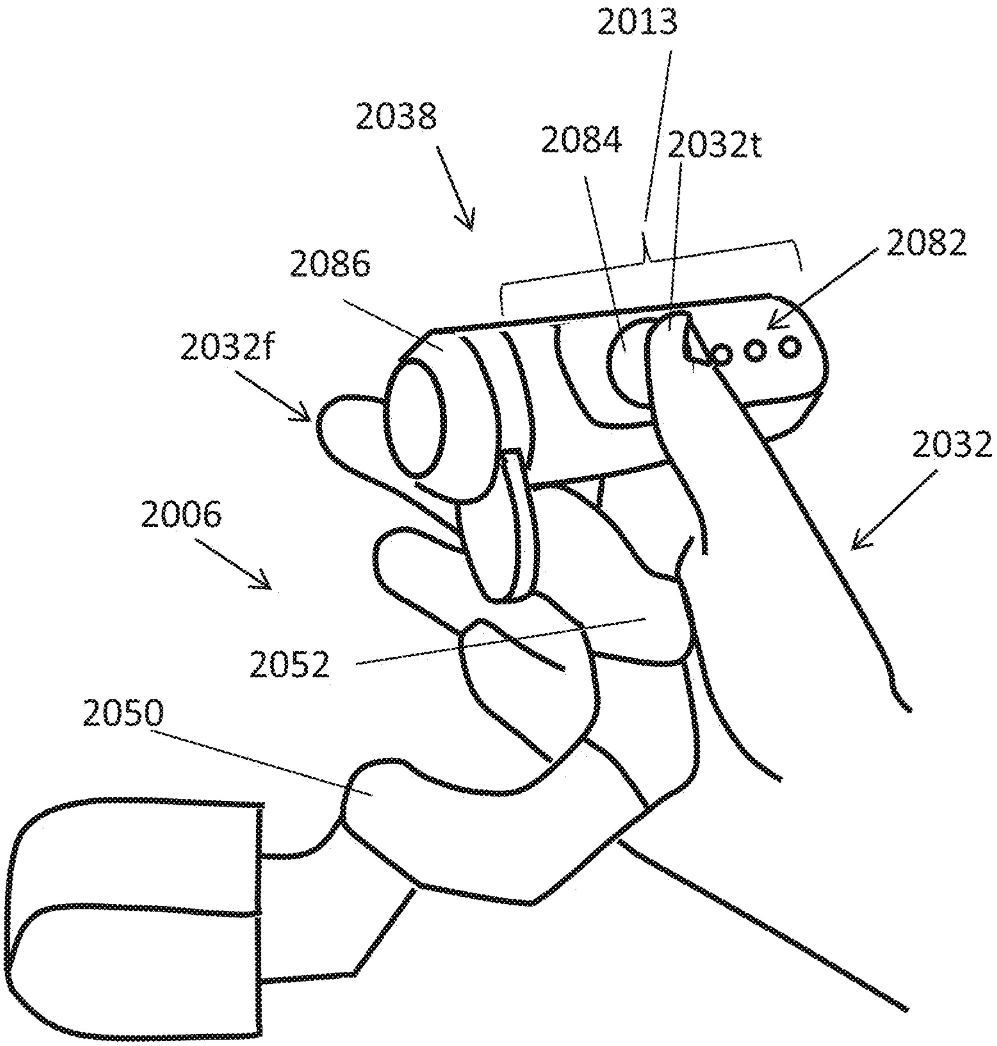
FIG. 20 is a simplified schematic of a user manipulating an input arm, according to some embodiments of the invention.

In some embodiments, a user controls movement of input arm 306 by holding a handle 338 (e.g. as described regarding handle 2038, FIG. 20). In some embodiments, handle 338 is attached to fourth portion 358 by a connector 375, where, in some embodiments, connector 375 is rigid.

In some embodiments, handle 338 extends in a direction towards second flexion joint from connector 375. In some embodiments, handle 338 is has an elongate shape where a long axis of the handle extends towards second flexion joint from connector 375.

Extending towards e.g. instead of away from rotational joint means that you can have the handle sized nicely for gripping while not increasing the volume of the possible positions. For example, in some embodiments a long axis length of the handle is 10-100%, or 10-95% or 30-100%, or 30-95%, or lower or higher or intermediate percentages or ranges of a maximum length of said input arm.

Optionally, in some embodiments, input arm 306 includes a third rotational joint 374. In some embodiments, handle 338 is rotatable e.g. with respect to fourth portion 358 about third rotational joint 374.

In some embodiments, an orientation of stand 370 is adjustable, with respect to a control console (e.g. as described regarding FIG. 3A).

In an exemplary embodiment, button 378, activates ability of movement of the input arm about joint 374, for example, in some embodiments, input arm 306 is held (e.g. locked) in position with respect to stand 370 and, in some embodiments, pressing on the button enables rotation (e.g. releasing a lock).

In some embodiments, to control movement of input arm 306, a user grasps handle 338. In some embodiments, handle 338 includes a loop 380, the user, for example, inserting a finger (e.g. index finger) into loop 380. In some embodiments, handle 338 includes one or more user interface 382, 384, 386 (e.g. as described regarding FIGS. 6A-B). In some embodiments, while grasping handle 338, a user interacts with one or more handle user interface 382, 384, 386 (e.g. as described regarding FIG. 20).

In some embodiments, input arm 306 is connected to stand 370 by connectors 390 and 392 (in an exemplary embodiment, connectors 390, 392 are bolts) which, when removed, provide access to connection of the input arm to stand 370 e.g. for removal and/or replacement of the input arm from the stand.

Figure 3E:
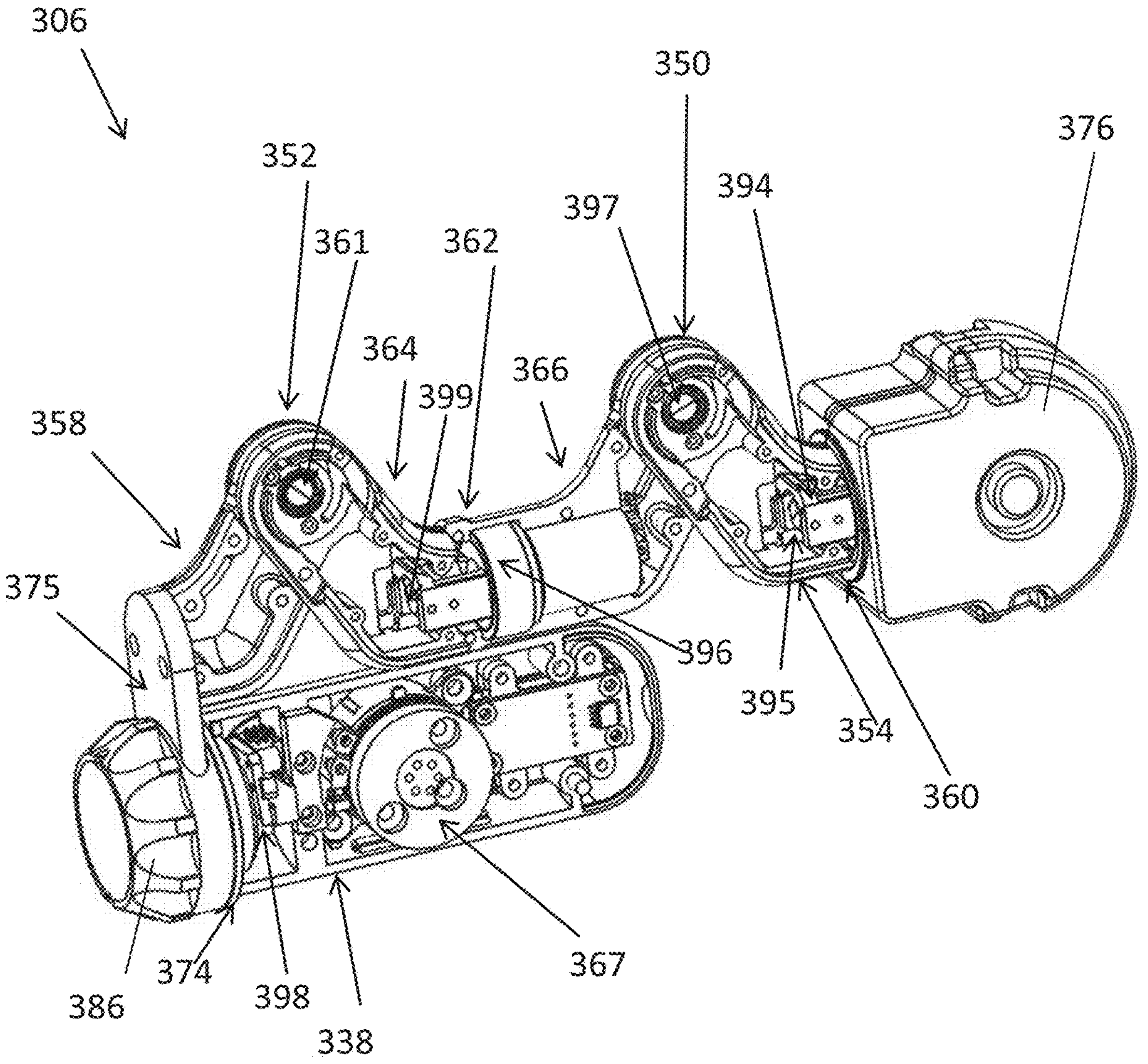
FIG. 3E is a simplified schematic view of an input arm, according to some embodiments of the invention.

FIG. 3E is a simplified schematic view of an input arm 306, according to some embodiments of the invention. In some embodiments, FIG. 3E illustrates a view of the input arm 306 illustrated in FIG. 3A and/or FIG. 3D where covers for portions of the arm and the handle have been removed to provide a view of inner elements of the input arm.

In some embodiments, input arm 306 includes a first and a second flexion joint 308, 320.

In some embodiments, segments move against each other, during rotation of the segments about a flexion joint. For example, in some embodiments, portion 362 moves against segment 356 during flexing of first flexion joint 350. In some embodiments, movement of portions against each other during flexion of one or more joint are configured to have low friction movement. For example, in some embodiments a first contacting portion having a brass surface in contact with a second contacting portion having a stainless steel surface.

In some embodiments, input arm 306 includes one or more sensor, configured to measure flexion at flexion joint/s and/or rotation at rotational joint/s. In some embodiments, sensor/s measure angle/s at one or more joint e.g. an orientation of one portion with respect to another portion, where the portions are coupled by a joint. In some embodiments, one or more sensor is a magnetic differential sensor, where, for example, a magnet is affixed to a first portion of a joint and a magnetic sensor is affixed to second portion of a joint which moves with respect to the first portion (e.g. rotation and/or flexion). In some embodiments, the sensor senses a change in magnetic field. In some embodiments, magnetic sensor/s transfer sensor signal/s through cables, e.g. to a processor. Alternatively or additionally, in some embodiments, connection between sensor/s and a processor is wireless.

In an exemplary embodiment, for one or more joint e.g. for both the first and second rotational joints, the sensor is connected to the more distal portion of the joint. In some embodiments, in the case of magnetic sensing, the magnet is connected to the more proximal portion of the joint. In some embodiments, for one or more joint, the sensor is connected to the more proximal portion of the joint and the magnet is connected to the more distal portion of the joint. Where a proximal end of the input arm is where it is connected to the stand and the distal end of the arm is at the handle.

In some embodiments, a first magnetic sensor 395 senses rotation of first section 354 at first rotational joint 360 e.g. by sensing movement and/or rotation of a magnet (not visible in FIG. 3E). In some embodiments, the magnet is coupled to and/or mounted on and/or within a screw.

In some embodiments, rotation of a second magnet 397 is measured e.g. by a magnetic sensor (not visible in FIG. 3E) e.g. to measure flexion at first flexion joint 350.

In some embodiments, a third magnetic sensor 399 senses rotation of second section 362 with respect to third section 364 at second rotational joint 362 e.g. by sensing rotation of a magnet (not visible in FIG. 3E). In some embodiments, the magnet is mounted on and/or within a screw.

In some embodiments, rotation of a forth magnet 361 is measured e.g. by a magnetic sensor (not visible in FIG. 3E) e.g. to measure flexion at second flexion joint 352.

In some embodiments, a fifth magnetic sensor 398 senses movement e.g. rotation of dial user interface 386 e.g. with respect to forth section 358 e.g. by sensing rotation of a magnet which rotates with dial 386. In some embodiments, sensed rotation of dial 386 is used to control rotation of a surgical mechanical arm end effector. Alternatively or additionally, in some embodiments, handle 338 is rotatable about a handle long axis e.g. as described regarding FIG. 3F.

In some embodiments, the input arm does not include sensors. For example, movement of the input arm being measured by sensor/s external to the input arm For example, in some embodiments, movement of an input arm is measured using motion capture technology where, for example, in some embodiments, movement of the input arm is inferred from images collected by one or more camera.

In some embodiments, electrical supply, for example, for sensor/s and/or user inputs (e.g. on handle 338) is supplied to input arm 306. In some embodiments, data (e.g. from sensor/s within the input arm) is passed through the arm.

For example, through a stand (not illustrated), passing through stand connection joint 376. In some embodiments, electrical supply and/or data is transferred through one or more rotational joint by slip rings. For example, first slip ring 394 transferring power and/or data from stand connection joint 376 to segment 356 and second slip ring 396 transferring power and/or data from portion 366 to portion 362.

In some embodiments, stand connection joint 376 includes a slip ring (not illustrated) for transfer of electrical power (and/or data) to the input arm through a stand (e.g. stand 370 FIGS. 3A-B).

In some embodiments, cable/s pass power and/or data across one or more of flexion joints 350, 352. In some embodiments, the cables are sufficiently long and/or have sufficient slack that flexion joints bend without tensioning the cables. Alternatively, in some embodiments, flexion joints also include slip rings for transfer of power and/or data.

Figure 6A:
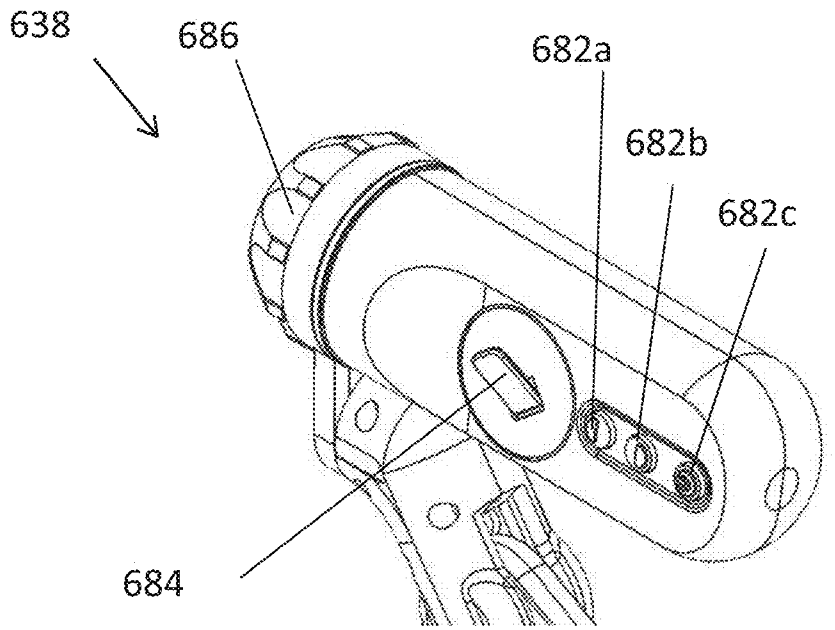
FIGS. 6A-6B are simplified views of an input arm handle, according to some embodiments of the invention.
Figure 6B:
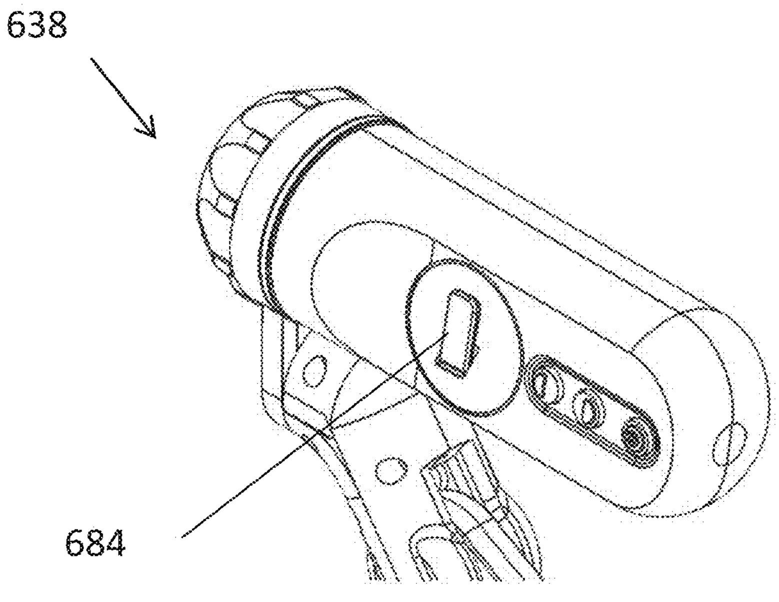

In some embodiments, handle 338 includes a slip ring 367 for power supply to and/or data transfer to a handle user interface (e.g. 384 FIG. 3B), where, an orientation of the handle user interface is adjustable with respect to the handle, e.g. as described regarding handle user interface 684 in FIGS. 6A-B.

In some embodiments, rotational joints (e.g. rotational joints) 356, 394 share an axis of rotation.

Figure 3F:
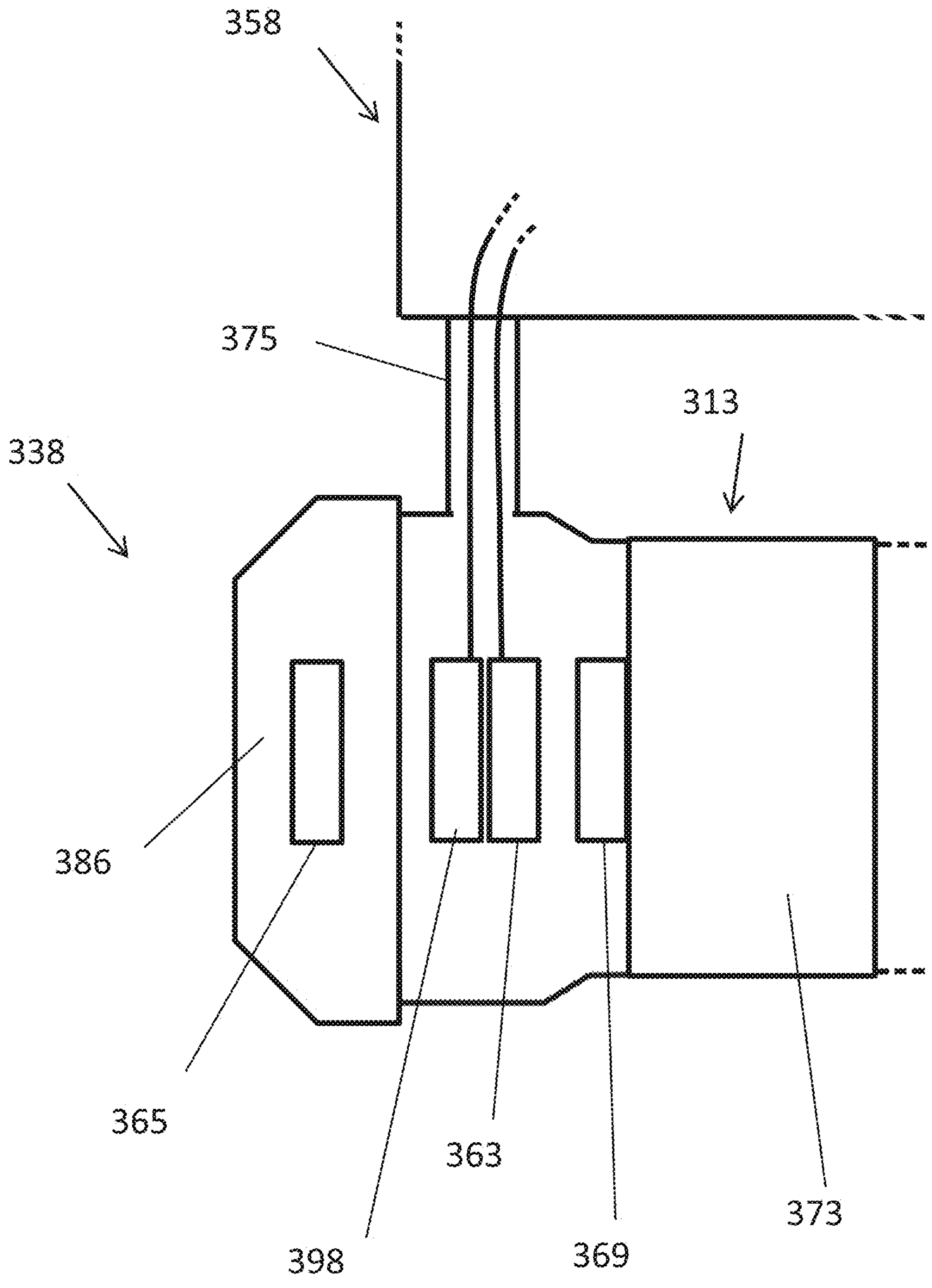
FIG. 3F is a simplified schematic cross sectional view of a portion of an input device handle, according to some embodiments of the invention.

FIG. 3F is a simplified schematic cross sectional view of a portion of an input device handle 338, according to some embodiments of the invention.

In some embodiments, control of a single movement of a surgical mechanical arm is controlled by measured movement of more than one input arm portion and/or controlled by more than one input arm user interface. Where a single movement is, for example, bending of a surgical device joint, rotation of a surgical device joint, actuation of a surgical device tool. In some embodiments, control signal/s for a single type of surgical device movement (e.g. control signals controlling one or more actuator e.g. a single surgical device actuator) are generated by more than one sensor signal (e.g. from more than one sensor). In some embodiments, a surgical mechanical arm movement is controlled by both a movement of the input arm and by an input arm user interface.

In an exemplary embodiment, both rotation of a dial and rotation of a body 313 of handle of input device handle 338 control rotation of a portion of a surgical mechanical device, e.g. rotation of an end effector of the surgical mechanical device. In some embodiments, an elongate body 313 of the handle 338 which is grasped by a user (e.g. as described and/or illustrated regarding handle body 2013 FIG. 20) is rotatable e.g. about a long axis of the body of the handle.

In some embodiments, one or more sensor 398, 363 detect rotation of two magnets 365 magnet 369. In some embodiments, a fifth magnet 365 moves with movement of user interface 386 where, for example, fifth magnet 365 is connected to user interface 386. In some embodiments, e.g. as described regarding FIGS. 3A-E, user interface 386 is a dial. In some embodiments, a sixth magnet 369 rotates with rotation of body 313 of handle. In some embodiments, a fifth magnetic sensor 398 senses rotation of fifth magnet 365 and a sixth magnetic sensor 363 senses rotation of sixth magnet 369. In some embodiments, the sensors have data and/or power connections which run along and/or through a connecting portion 375 to an input arm forth section 358.

A potential benefit of dual rotation controls on the handle is maintained ease of control, for different orientations and/or user grips on the handle. For example, in some orientations of the handle, it is difficult for a user to rotate the handle, in which case, the user may use the dial and vice versa, in orientations of the handle where it is difficult for the user to rotate the dial.

In some embodiments, handle 338 includes a slip ring 373 for transfer of power and/or data through handle body 313, e.g. to one or more user interface e.g. 382, 384 FIG. 3D.

Although magnets and magnetic sensors in FIG. 3F have been termed “fifth” and “sixth” it is to be understood that, in some embodiments, the handle illustrated in FIG. 3F is part of an input arm with less or more than six magnets and/or magnetic sensors.

Figure 4A:
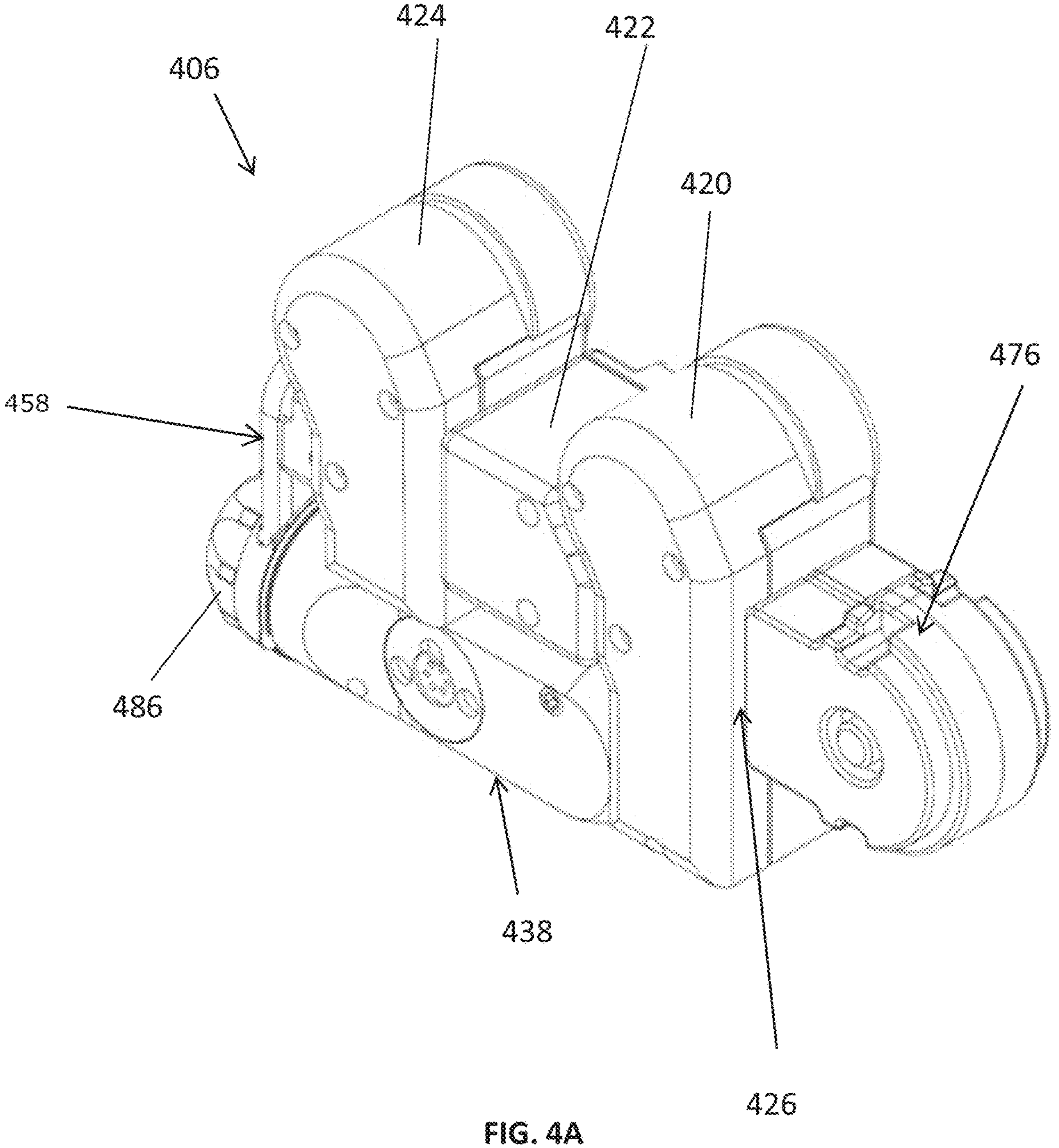
FIG. 4A is a simplified schematic isometric view of an input arm, according to some embodiments of the invention.

FIG. 4A is a simplified schematic isometric view of an input arm 406, according to some embodiments of the invention.

Figure 4B:
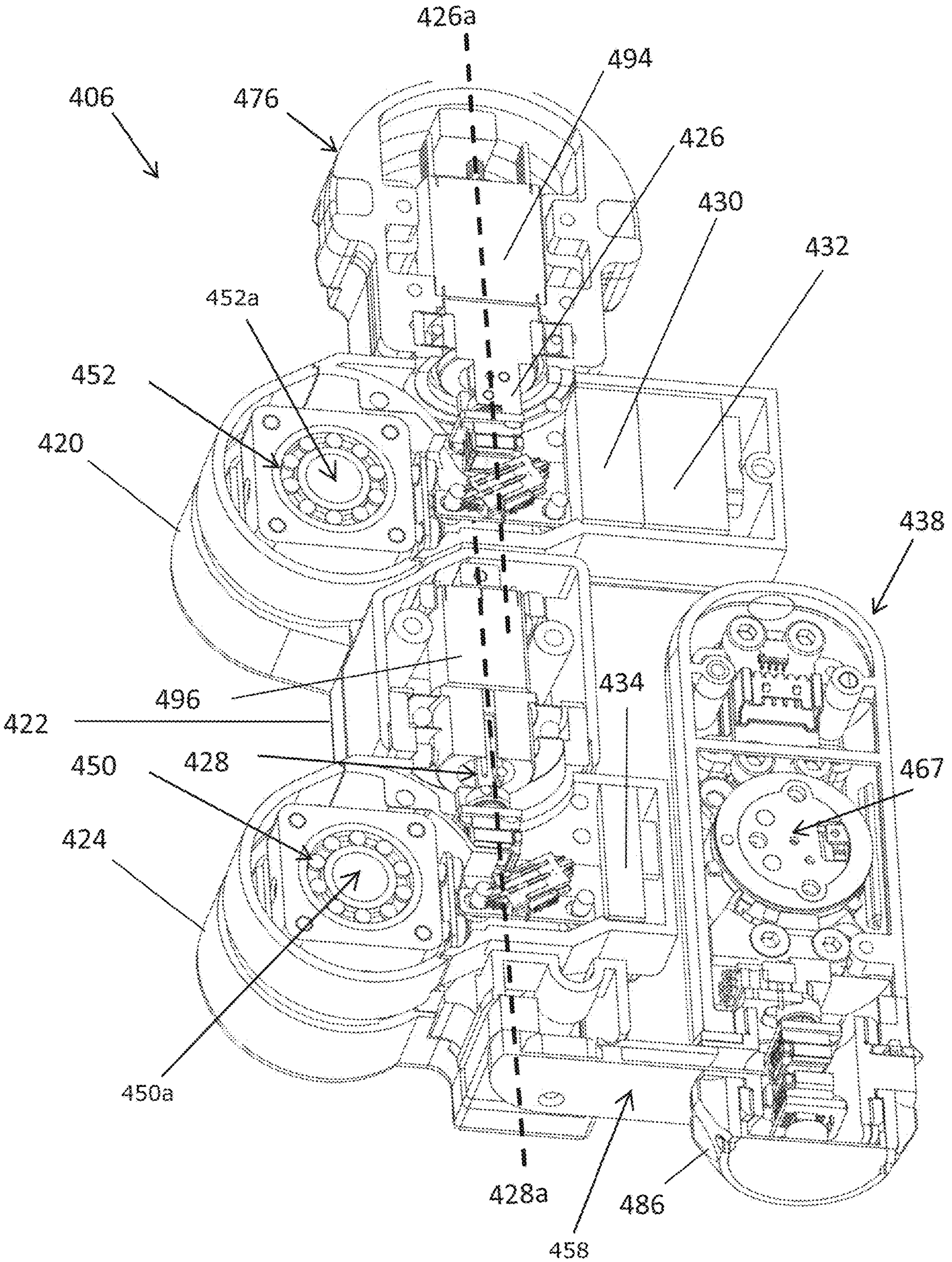
FIG. 4B is a simplified schematic section view of an input arm, according to some embodiments of the invention.

FIG. 4B is a simplified schematic section view of an input arm 406, according to some embodiments of the invention.

In some embodiments, FIG. 4B is a sectional view of the input arm illustrated in FIG. 4A.

In an exemplary embodiment, input arm 406 includes four sections, where, for example, a first section 420 is coupled to a support portion 476 by a first rotational joint 426, first section 420 is coupled to a second section 422 by a first flexion joint 452, second section 422 is coupled to a third section 424 by a second rotational joint 428, and third section 424 is coupled to a fourth section 458 by a second flexion joint 450.

Figure 4C:
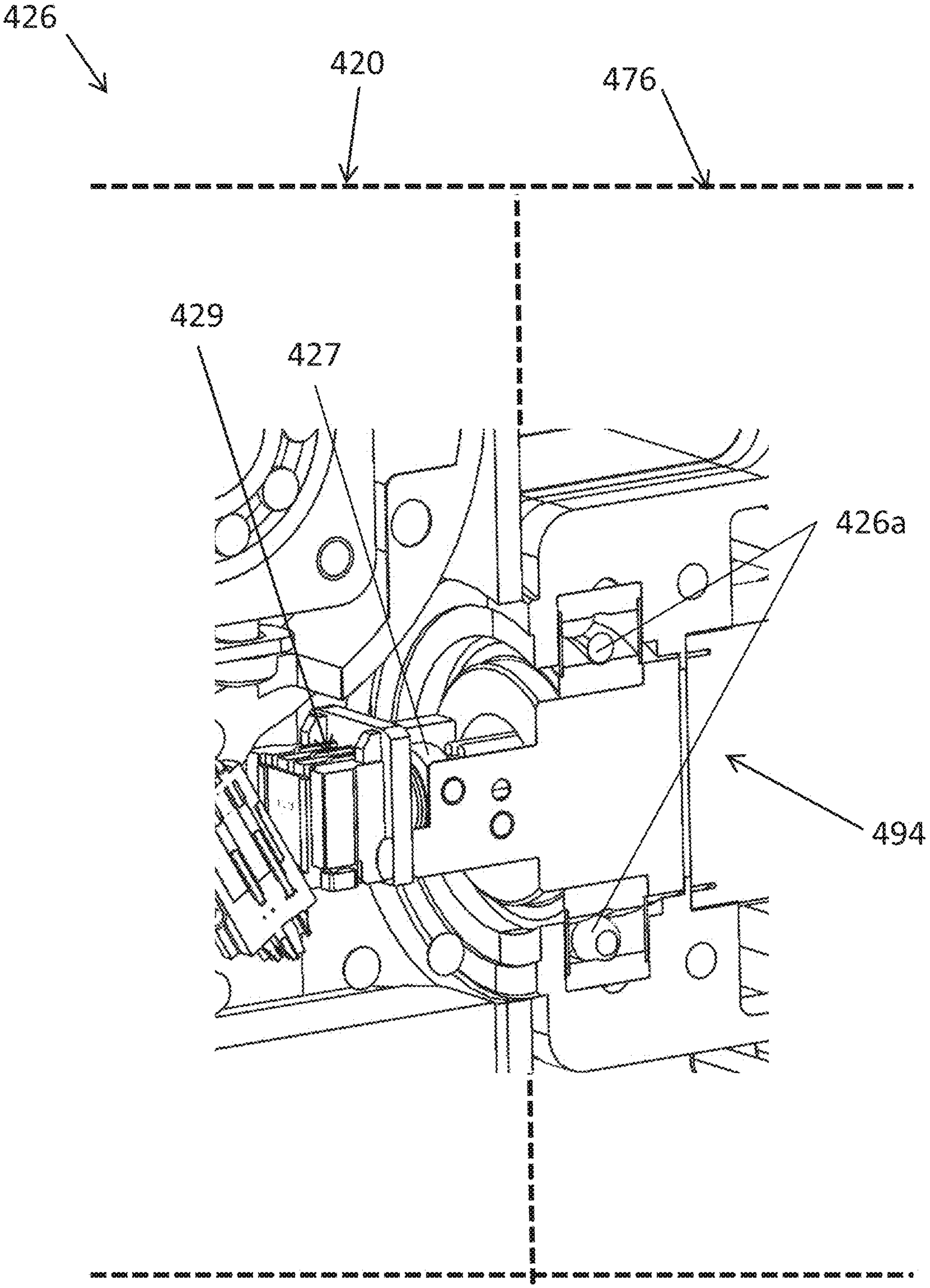
FIG. 4C is a simplified schematic view of a portion of an input device including a first rotational joint, according to some embodiments, of the invention.
Figure 4D:
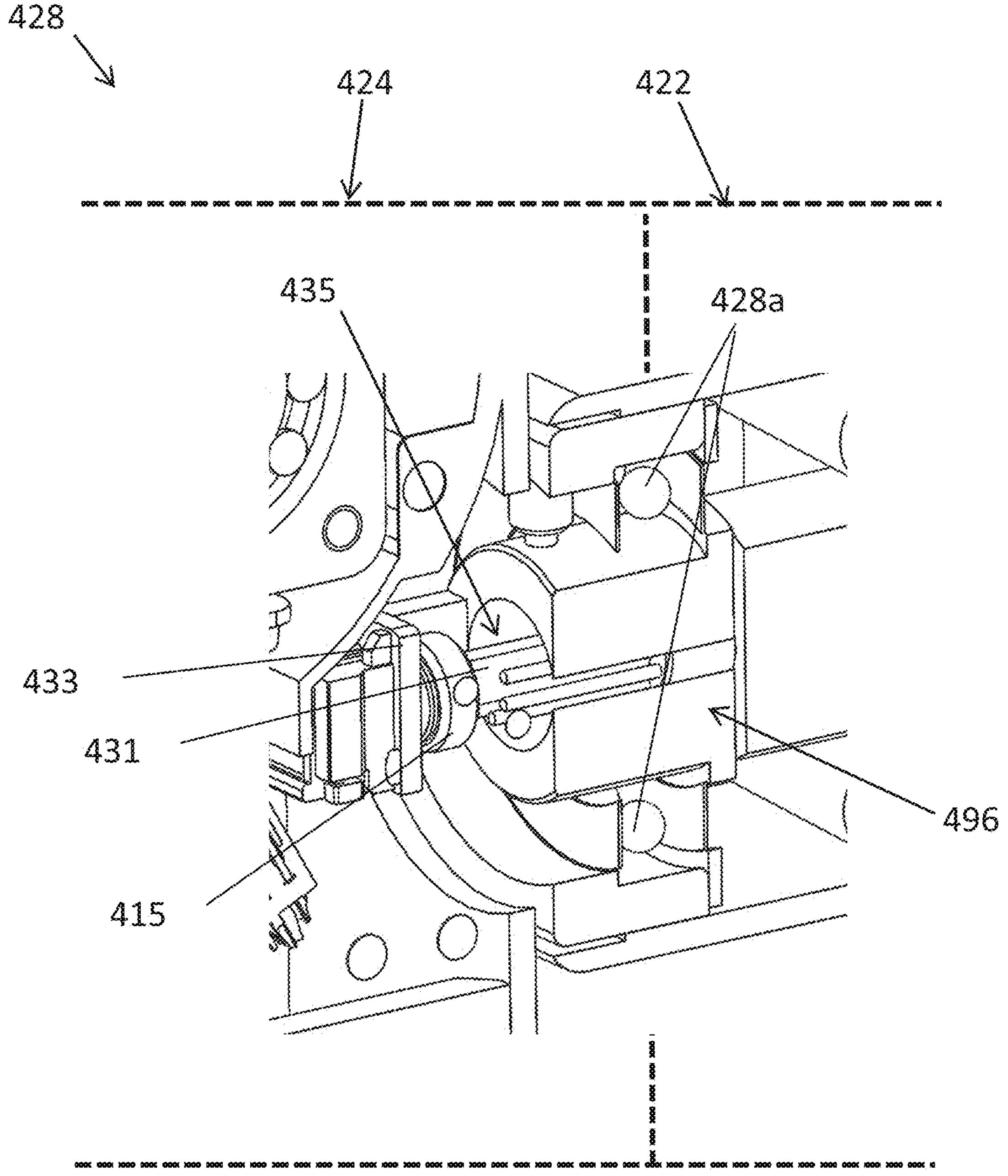
FIG. 4D is a simplified schematic view of a portion of an input device including a second rotational joint, according to some embodiments, of the invention.

In some embodiments one or more flexion joint includes ball bearings 452*a*, 450*a*, and/or one or more rotational joint includes ball bearings e.g. 426*a* FIG. 4C, 428*a* FIG. 4D, potential benefits being robustness of the joint and/or smooth movement and/or low friction movement of portions of the input arm about the joint.

In some embodiments, input arm 406 includes one or more slip ring, 494, 496, for example, the slip ring/s located at rotational joints for example, for transfer of power and/or data through the input arm 406 (e.g. as described regarding slip rings 394, 394 FIG. 3E).

In some embodiments, cable/s pass power and/or data across one or more of flexion joints 450, 452. In some embodiments, the cables are sufficiently long and/or have sufficient slack that flexion joints bend without tensioning the cables.

Alternatively, in some embodiments, flexion joints also include slip rings for transfer of power and/or data.

FIG. 4C is a simplified schematic view of a portion of an input device including a first rotational joint 426, according to some embodiments, of the invention.

FIG. 4D is a simplified schematic view of a portion of an input device including a second rotational joint 428, according to some embodiments, of the invention.

In some embodiments, FIGS. 4C-D are enlarged portions of FIG. 4B.

In some embodiments, FIG. 4C illustrates a part of support portion 476 and a part of first portion 420. In some embodiments, FIG. 4D illustrates a part of second portion 422 and a part of third portion 424.

In some embodiments, one or more rotational joint includes ball bearings 426*a*, 428*a*. Potentially, ball bearings reduce friction at the joints.

In some embodiments, relative rotation of portions of the input device coupled at a rotational joint is measured by one or more sensor.

For example, referring to FIG. 4C, in some embodiments, a magnet 427 is mounted on a shaft (not visible in FIG. 4C) where first portion 420 is rotatable about the shaft. In some embodiments, a magnetic sensor 429, located within the first portion 420 senses rotation of the shaft with respect to the first portion. In some embodiments, the magnet and magnetic sensor are co-axial, for example, the magnetic sensor detecting change in magnetic field.

For example, referring to FIG. 4D, in some embodiments, a magnet 415 is mounted on shaft 431 where second portion 422 is rotatable about shaft 431. In some embodiments, a magnetic sensor 433, located within the third portion 424 senses rotation of the shaft with respect to third portion 424. In some embodiments, the magnet and magnetic sensor are co-axial, for example, the magnetic sensor detecting change in magnetic field.

Visible in FIG. 4D are cables for transfer of power and/or data 335. In some embodiments, do not terminate as illustrated but extend through the joint.

Exemplary Volume of Input Arm Configurations

In some embodiments, the size and shape of the volume of possible positions of the input arm is defined by length of portions of the input device and range of rotation and flexion of the joints.

Figure 3G:
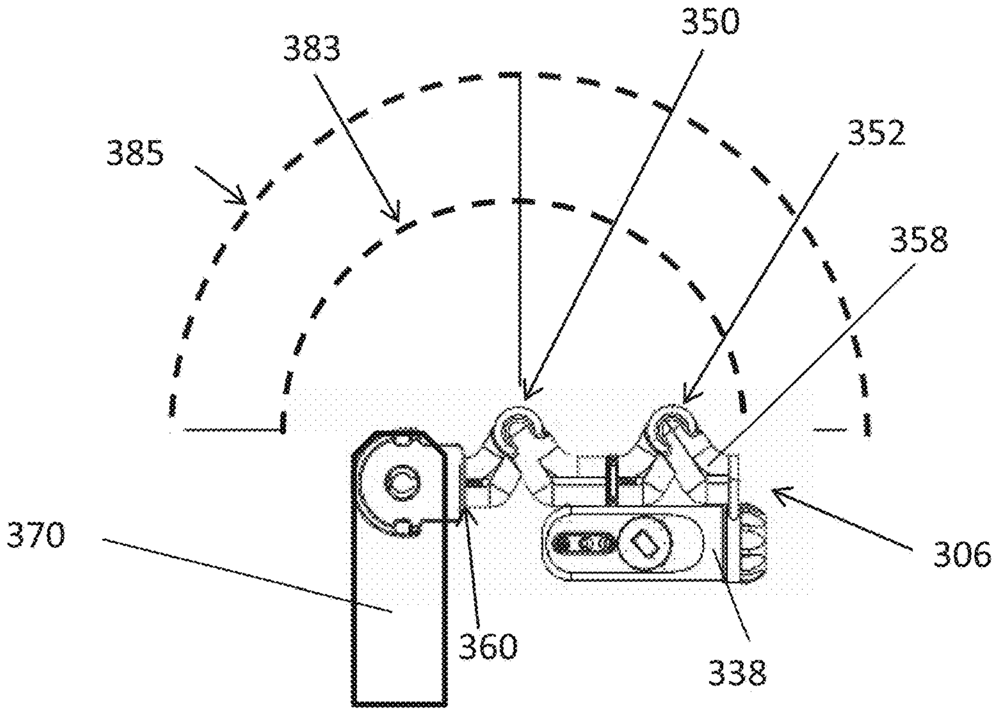
FIGS. 3G-3I are simplified schematic views of configurations of an input arm and outer contours of potential positions of the input arm, according to some embodiments of the invention.
Figure 3H:
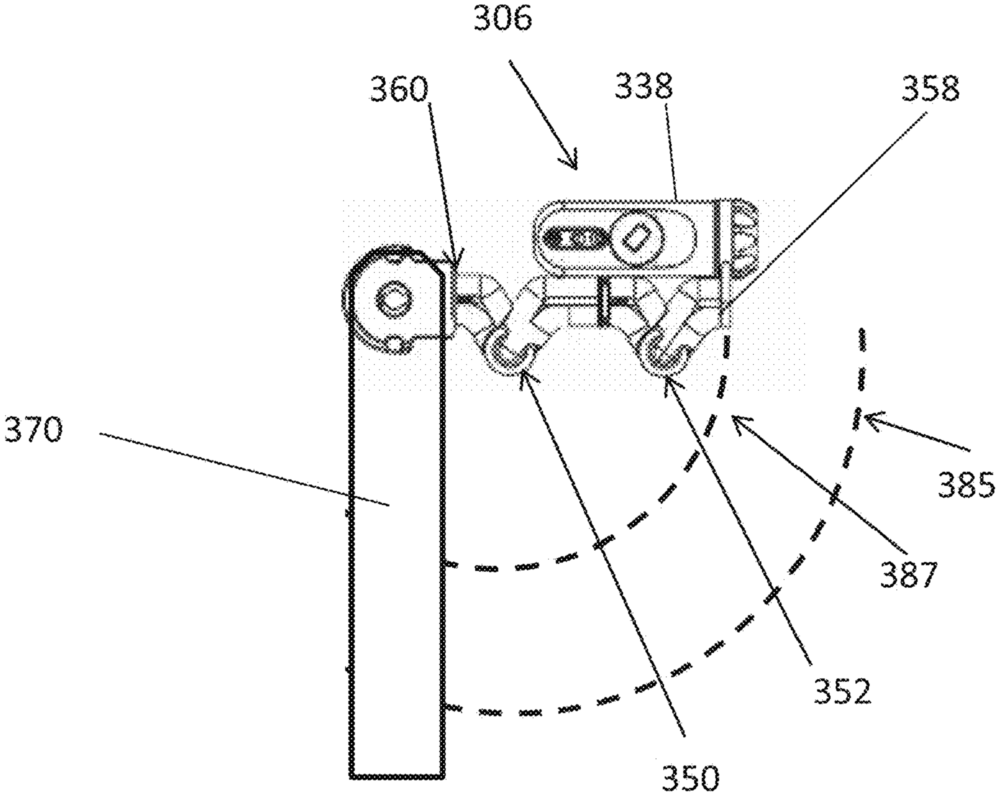
Figure 3I:
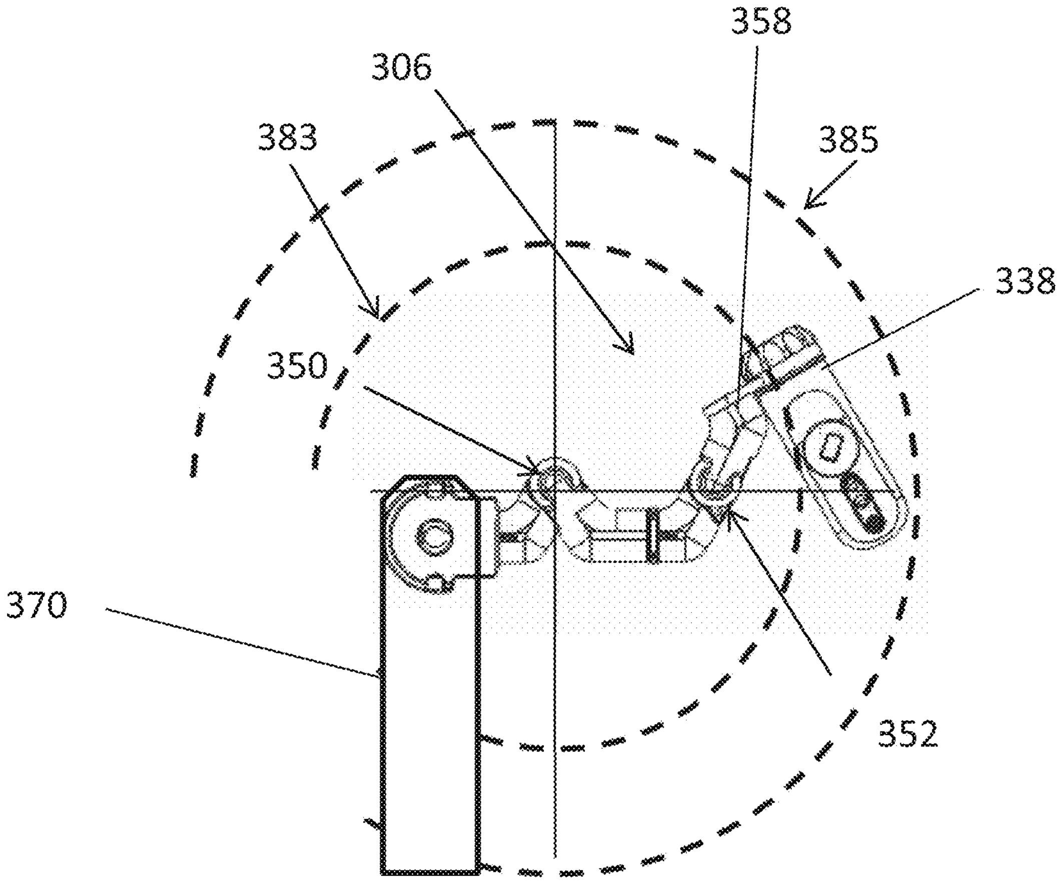

FIGS. 3G-I are simplified schematic views of configurations of an input arm 306 and outer contours 383, 385 of potential positions of the input arm, according to some embodiments of the invention. In some embodiments, the volume of possible positions of input arm 306 is enclosed and/or partially described by spheres centered on a first flexion joint 350.

FIG. 3G illustrates a single configuration of input arm 306 and, in some embodiments, contour 338 illustrates possible positions possible positions of a distal end of an input arm fourth portion 358. In some embodiments contour 338 is a semicircle centered on first flexion joint and/or a portion of a circle, the edges of which are defined by stand 370 and flexion joints 350, 352 which, in some embodiments, each open to a maximum angle. Where, in some embodiments the maximum angle is 170-250°, or 170-220°, or about 180° or lower or higher or intermediate angles or ranges e.g. as illustrated in FIG. 3G. In some embodiments, input arm is rotatable about a first rotation joint 350 meaning that a volume of possible positions of the input arm includes a portion of a sphere (e.g. a hemisphere) extending above a top and/or distal end (where, in some embodiments the top is the distal end) of stand 370. Where stand 370, in some embodiments, prevents rotation of arm portions distal of the first flexion joint about the first flexion joint of more than about 170-250°, or 170-220°, or about 180° or lower or higher or intermediate angles or ranges.

In some embodiments, once flexion joints are rotated about first rotational joint 360 such that the flexion joints are below the top and/or distal end of stand 370, e.g. disposed in space laterally around stand 360, the volume of possible positions of the input arm is reduced. For example, to a quarter sphere, where contour 387 FIG. 3H illustrates possible positions of the distal end of fourth section 358 for the input arm configuration illustrated in FIG. 3H.

Referring now to FIG. 3I, in some embodiments, an elongate handle 338 extending from fourth portion 358, extends a volume of possible positions of the input arm, for at least some angles of rotation of first flexion joint 350 and/or angles of rotation of second flexion joint 352. Where the volume, at least in some regions, is extended to a contour of a sphere 385 centered on first rotational joint 350.

In some embodiments, a volume of possible positions of an input arm is approximately spherical, where a diameter of the sphere is 100-800 mm, or 100-500 mm or about 370 mm, or lower or higher or intermediate ranges or values.

In some embodiments, a control console includes a plurality of input arms (e.g. two) where the volume of possible positions of the input arm is the same shape and/or size. Alternatively, in some embodiments, a control console includes input arms where the volume of potential positions of one input arm is different in shape and/or size to that of another input arm, input arms, for example, being different sizes and/or with different possible extent of rotation and/or flexion at rotational joints and flexion joints respectively.

In some embodiments, an input arm is configured such that a user comfortably moves the input arm throughout the volume of possible positions of the arm using wrist movement of a single arm, where, for example, user forearms remain resting on armrests. In some embodiments, both of two input arms are configured such that the user comfortably controls movement of each arm with wrist movement of one hand.

In some embodiments, a separation between attachment of the input arms to the control console (e.g. separation between centers of stands 370, 371 FIG. 3A) is selected for user comfort. In some embodiments, separation is reduced below a sum of the lengths of the input arms, the input arms potentially colliding. A potential benefit of input arms being close together being user comfort (e.g. when a user controls an input arm with each user hand). In some embodiments, separation between a center of extension of a proximal arm portion from a stand and/or a separation between stand long axes 50-500 mm, or 200-500 mm, or about 340 mm, or lower or higher or intermediate ranges or values.

In some embodiments, different input arms, e.g. as described in this document (e.g. input arm 106 FIG. 1, 206, 230 FIG. 2, 306 FIGS. 3A-F, 406 FIGS. 4A-D, 506 FIG. 5) have a volume of possible positions including one or more feature as described in this section "Exemplary volume of input arm configurations" and/or illustrated in one or more of the figures to which this section refers.

Exemplary Biasing of Exemplary Input Arm

Returning back now to FIG. 4B, in some embodiments, input arm 406 is biased. For example, by one or more weight which is e.g. attached to one or more input arm portion e.g. attached to and/or within a hollow (e.g. tubular) arm portion. In an exemplary embodiment, combined weights of weights 430 and 432 bias first portion 420 about axis 426*a* and weight 534 biases weight of second portion 424 about axis 428*a*.

In some embodiments, the input arm is biased (e.g. one or more weight is selected) to return the input arm to a null position e.g. under gravity e.g. upon a user releasing the input arm.

In some embodiments, a weight is selected to generate sufficient torque to overcome friction in moving (e.g. rotating) one or more portion of the input arm. In some embodiments, a weight is selected to maintain a center of gravity of one or more portion (e.g. a portion, the entire input arm) below a central long axis of the portion and/or input arm.

In some embodiments, a weight on a portion is configured to return the portion, under gravity, to an null orientation, upon release of the portion. In an exemplary embodiment, weights 420 and 432 together weigh 100-200 g, or 130-150 g or about 140 g or lower or higher or intermediate ranges or weights. In some embodiments, one or more of weights 434, 436, 438 include (e.g. are constructed from) stainless steel.

Alternatively or additionally, in some embodiments, biasing is implemented e.g. using magnetic biasing and/or using one or more actuator e.g. one or more spring, one or more motor.

In some embodiments, the input arm is biased so that the null position is where flexion joints are disposed at a further separation from an input arm support and/or attachment of the input arm to the console (e.g. stand 370 FIG. 3D) than other portions of the input arm. For example, in some embodiments (e.g. as illustrated in FIG. 3D) attachment of the input arm extends downwards and the null position (e.g. as illustrated in FIGS. 3A and 3D) is where the flexion joints are above other portion/s of the arm. In some embodiments, a null position is where the arm is straight, e.g. with each flexion joint open to about 180° (e.g. as illustrated in FIGS. 3A and 3D). A potential benefit of this being that the flexion joints are biased in a position that bending of the joints is not restricted by the input arm support (e.g. stand 370 FIG. 3D). A further potential benefit is ease of manipulation of the input arms by the user, where, for example, bending the input arms upwards, in some embodiments is more comfortable and/or easier to control than bending the input arms downwards.

In some embodiments, biasing forces (e.g. weight of the weights) are selected such that movement of the input arm/s has enough inertia that accidental movement of the input arm does not occur and/or so that but not so much inertial that moving the input arms causes excessive user fatigue.

Figure 5:
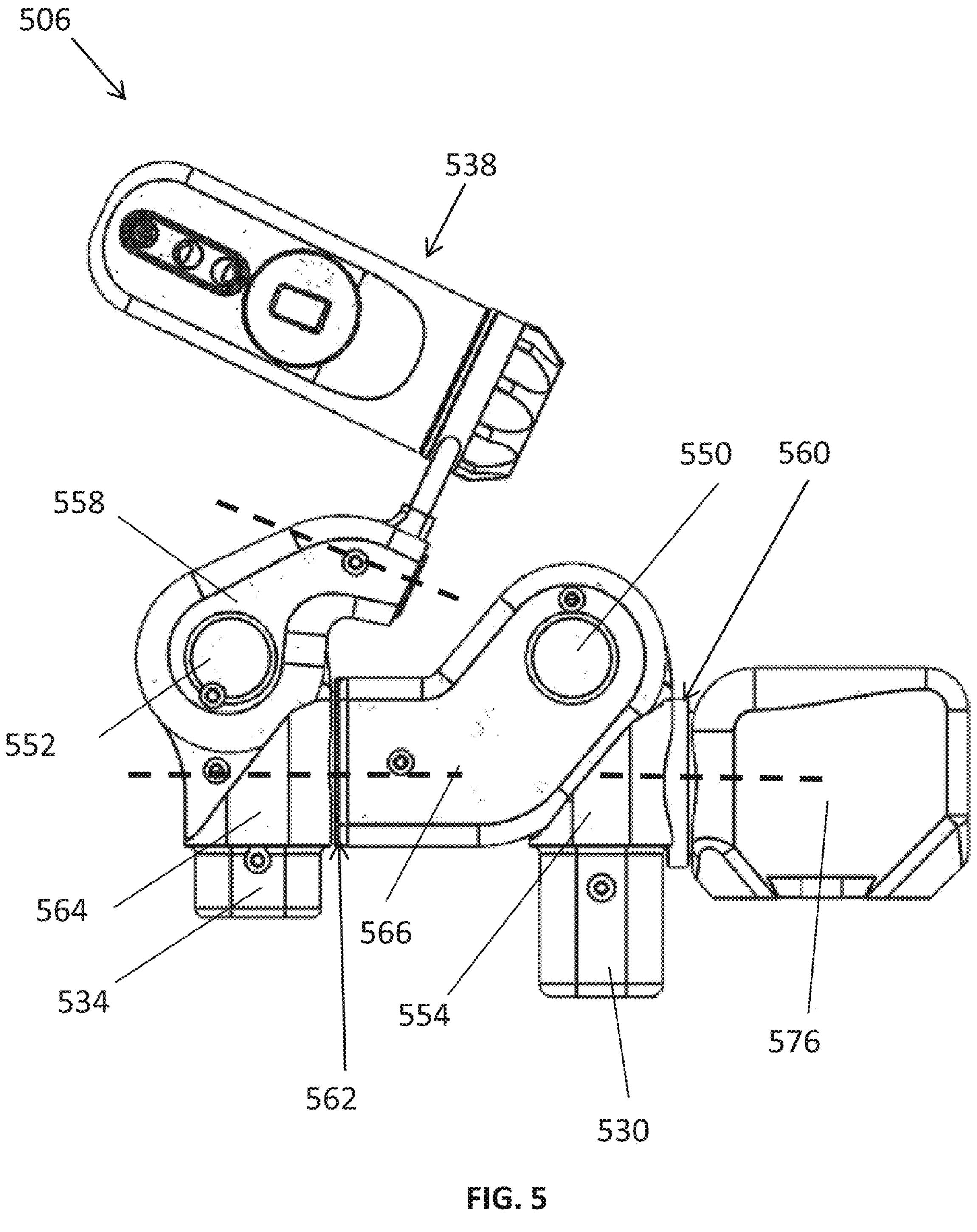
FIG. 5 is a simplified schematic side view of an input arm, according to some embodiments of the invention.

FIG. 5 is a simplified schematic side view of an input arm 506, according to some embodiments of the invention.

In an exemplary embodiment, input arm 506 includes four sections, where, for example, a first section 554 is coupled to a 576 stand connection joint 576 by a first rotational joint 560, first section 553 is coupled to a second section 566 by a first flexion joint 550, second section 566 is coupled to a third section 564 by a second rotational joint 562, and third section 564 is coupled to a fourth section 558 by a second flexion joint 552.

In some embodiments, one or more portion of the input arm is weighted. For example, input arm including one or more of weights 530, 534 where weighting, for example, includes one or more feature as described and/or illustrated regarding weights 430, 434 FIG. 5.

Exemplary Method of Retroflection, Exemplary Control of Retroflection

Figures 21, 22:
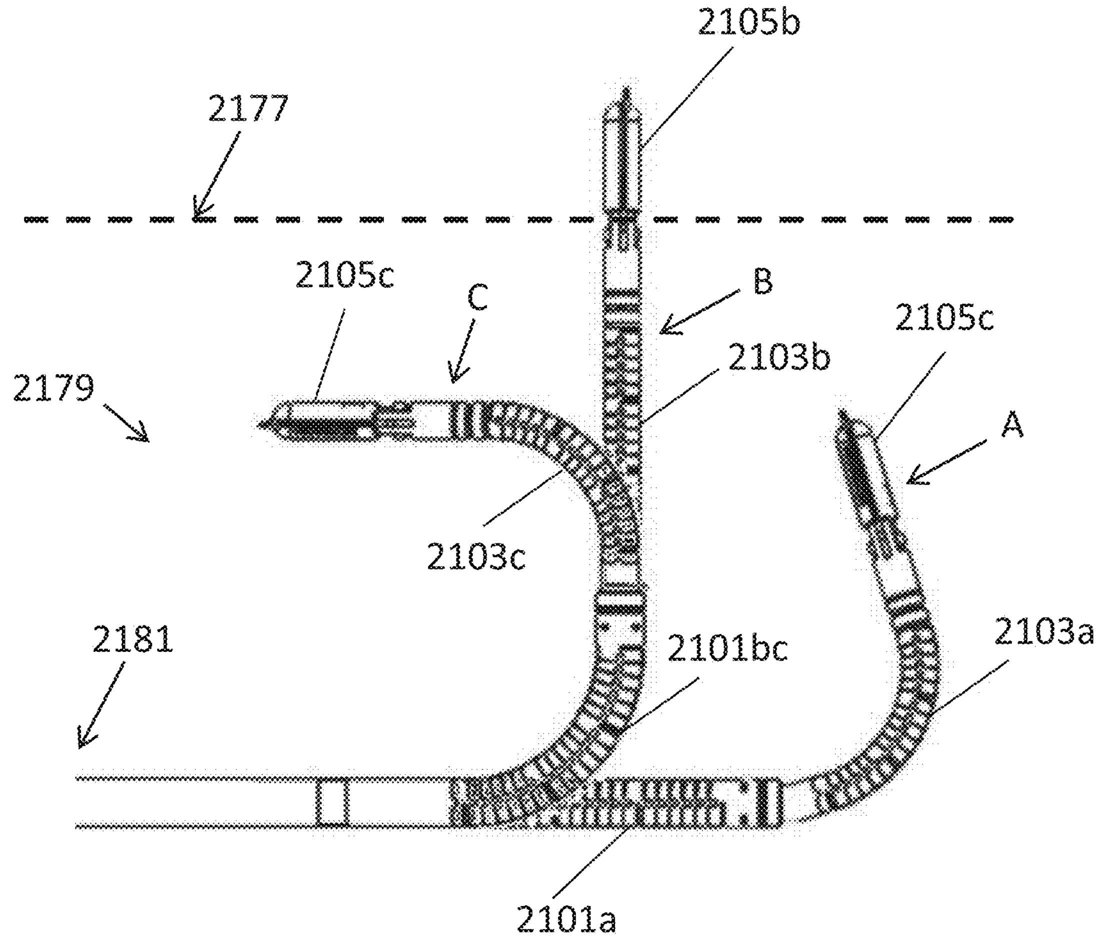
FIG. 21 is a simplified schematic side view of a surgical mechanical arm, in different configurations, according to some embodiments of the invention.
FIG. 22 is a flow chart of a method of surgical device retroflection, according to some embodiments of the invention.
Figure 23A:
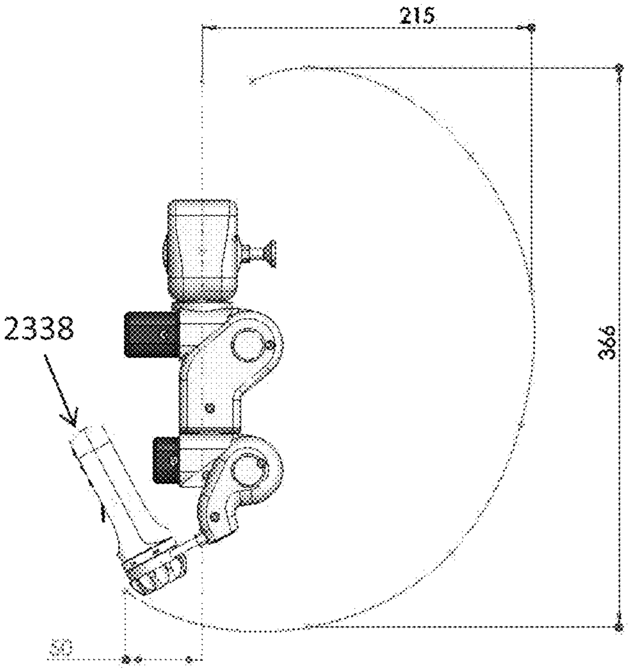
FIGS. 23A-23E are simplified schematic top views of an input arm, according to some embodiments of the invention.
Figure 23B:
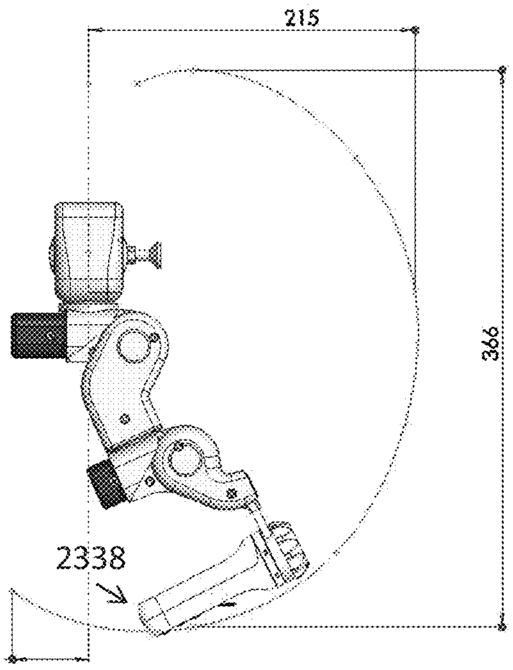
Figure 23C:
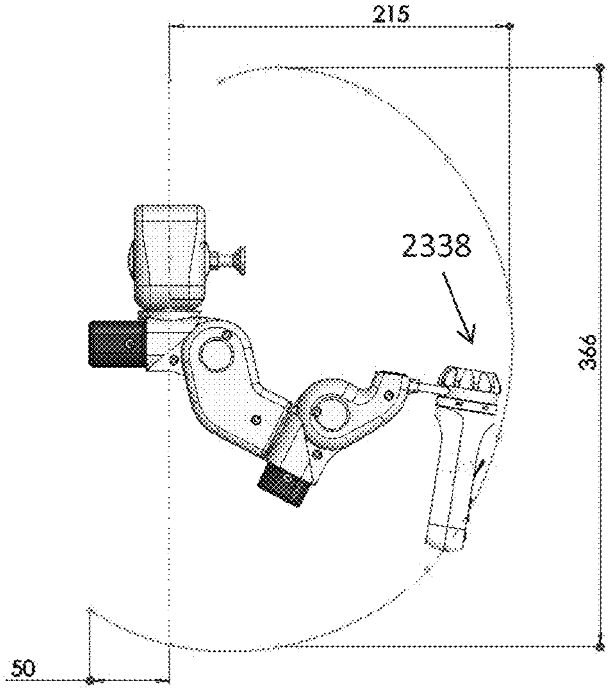
Figure 23D:
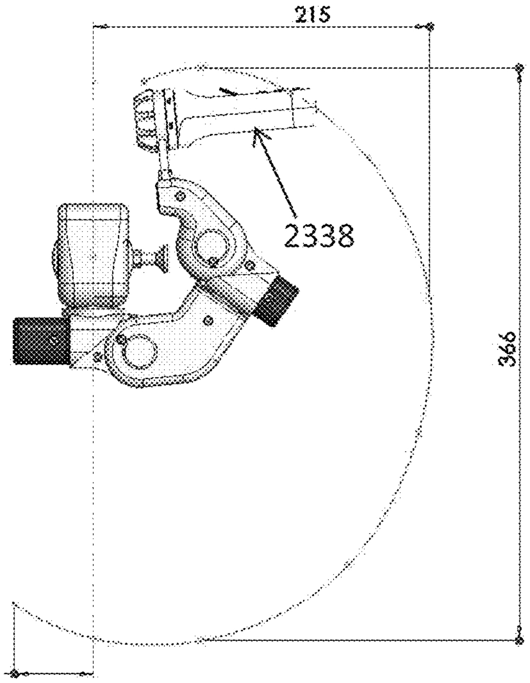
Figure 23E:
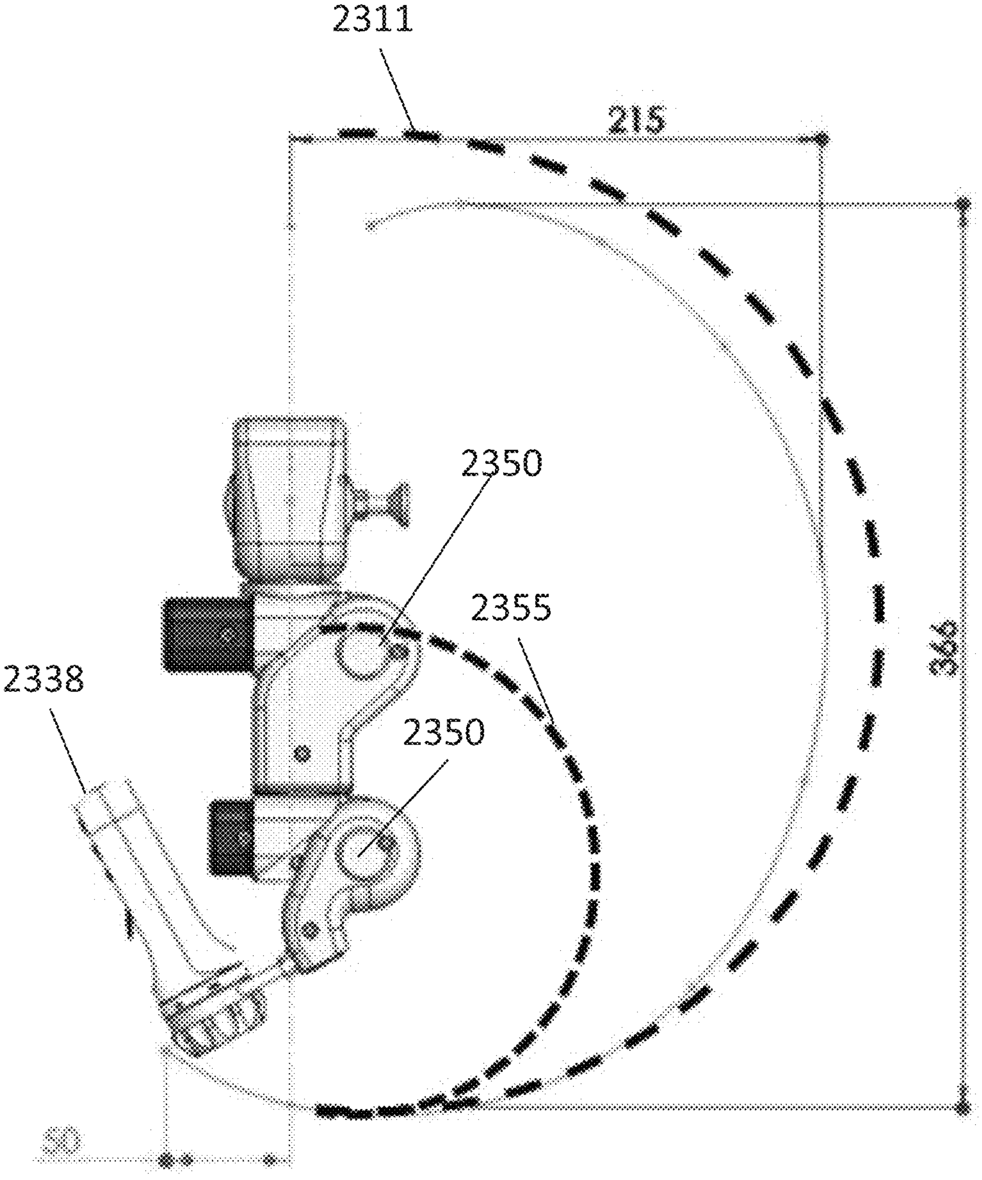

FIG. 21 is a simplified schematic side view of a surgical mechanical arm, in different configurations, according to some embodiments of the invention.

In some embodiments, bending (e.g. retroflection) movement of a surgical mechanical arm is controlled to reduce an area (e.g. within a patient) in which the arm is located, for example, during part of a surgical procedure. In some embodiments, the mechanical arm is controlled to prevent contact or collision of the arm with an obstacle 2177. In some embodiments, the obstacle is a portion of patient tissue for example, an inner wall of the abdomen. In some embodiments, the surgical arm is inserted into a patient through an incision where, in some embodiments, the patient has been insufflated. Insulation, for example, providing a working area 2179 for the surgical device within the patient, where the working area is, in some embodiments, at least partially bounded by user tissue 2177, where, in some embodiments, user tissue is an inner wall of the abdomen.

In some embodiments, the surgical device is a surgical mechanical arm including a plurality of flexible portions 2101*a-c*, 2103*a-c*, disposed between a proximal and a distal end of the surgical arm. Where, in some embodiments, a proximal end 2181 of the arm is coupled to actuator/s configured to actuate movement of the surgical arm and, in some embodiments, the distal and is coupled to an end effector. In some embodiments, the end effector 2105*a-c* is configured to be electrically charged e.g. for electrosurgery.

FIG. 21 illustrates retroflection of the surgical arm to configuration C with (illustrated by configuration B) and without (illustrated by configuration A) contacting and/or broaching boundary 2177.

FIG. 22 is a flow chart of a method of surgical device retroflection, according to some embodiments of the invention.

At, 2200, in some embodiments, a bendable portion distal of one or more other bendable portions of a surgical mechanical arm is bent. In some embodiments, the most distal bendable portion of the surgical arm is bent.

At, 2202, in some embodiments, a proximal bendable portion is bent to retroflect the surgical arm.

In some embodiments, a surgical mechanical arm is retroflected as described and/or illustrated regarding FIGS.

21-22, upon identifying potential collision of the surgical arm with an obstacle, which is, in some embodiments, the abdominal wall.

In some embodiments, a user identifies the potential collision e.g. using images collected by a laparoscopic camera. In some embodiments, the user then retroflects the arm by manipulating an input arm controlling the surgical arm. For example, by first bending an input arm second flexion joint and then bending an input arm first flection joint (e.g. flexion joints as described in one or more embodiment, elsewhere in this document).

In some embodiments, the surgical system includes circuitry configured to identify a possible collision (e.g. hosted by one or more processor, e.g. processor 110 FIG. 1). For example, in some embodiments, a possible collision is identified using data from one or more sensor and/or one or more camera and/or imaging data from one or more imager (e.g. CT, MRI, ultrasound, x-ray).

In some embodiments, upon identifying a possible collision, control instructions are displayed to a user, for example, by one or more user interface e.g. user interface/s 234, 240 FIG. 2). In some embodiments, instructions include display e.g. visual and/or audio guiding retroflection e.g. by first bending an input arm second flexion joint and then bending an input arm first flexion joint.

In some embodiments, upon identifying a possible collision, a user interface and/or the surgical device is prevented from bending into a collision.

For example, in some embodiments, upon detecting a collision, movement/s of the input arm are prevented (e.g. by one or more brake) and/or control of the surgical arm by movements of the input arm is disabled and/or movement of the surgical arm is stopped.

For example, in some embodiments, if user manipulation of the input device would cause the surgical device to collide, a shape of the surgical device fails to correspond and/or match that of the input device. For example, in some embodiments, a user retroflects the input device arm by bending the input arm at the first input device flexion joint. Circuitry then changes the control signal to instruct bending at the second bendable portion followed by bending at the first bendable portion.

FIGS. 23A-E are simplified schematic top views of an input arm, according to some embodiments of the invention.

Figure 24A:
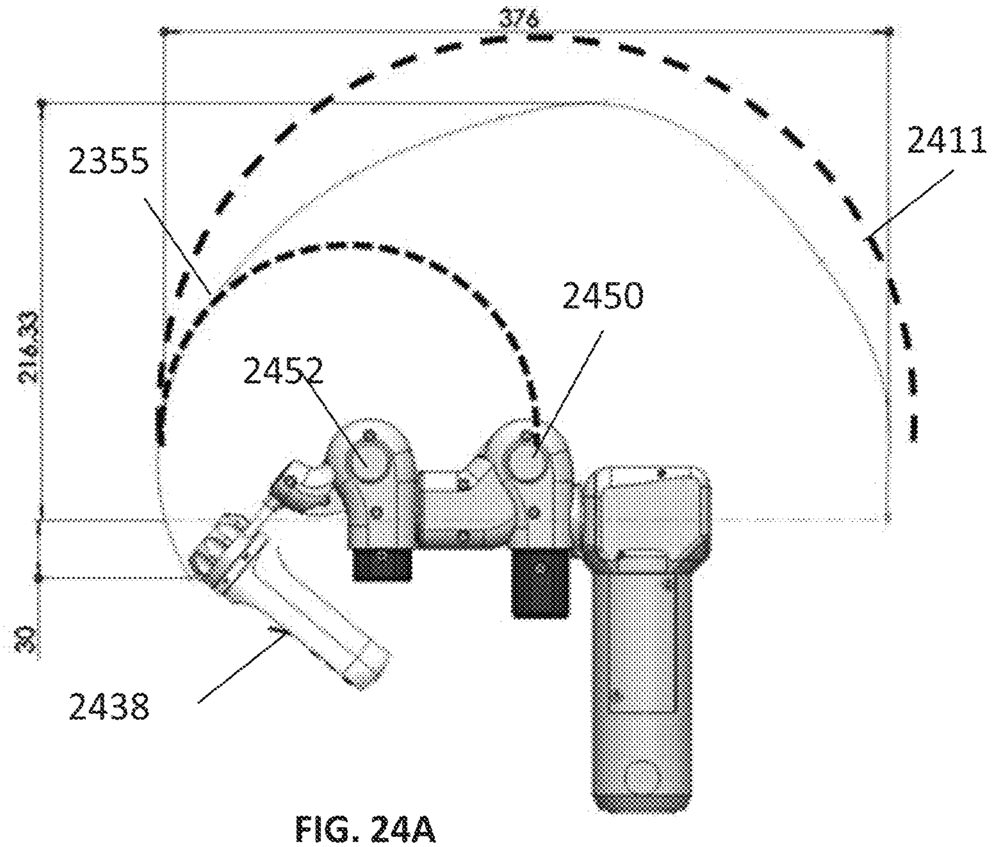
FIGS. 24A-24B are simplified schematic side views of an input arm, according to some embodiments of the invention.
Figure 24B:
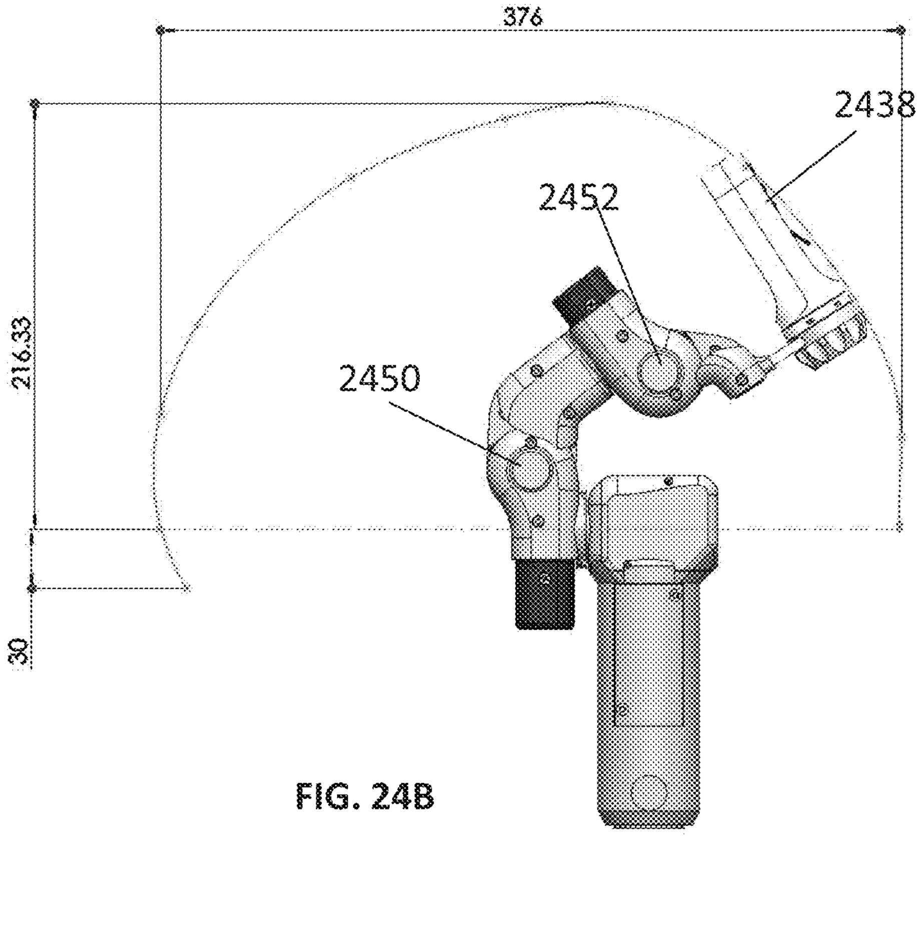

FIGS. 24A-B are simplified schematic side views of an input arm, according to some embodiments of the invention.

In some embodiments, FIGS. 23A-E and FIGS. 24A-B illustrate control of retroflection of a surgical arm, e.g. as described above. In some embodiments, solid contour lines illustrate a contour of a path of an input device handle 2338 FIGS. 23A-E, 2438 FIGS. 24A-B during retroflection.

A potential benefit of retroflection e.g. as described above e.g. where a first input device flexion joint is bent and then a second input device joint is bent is that the path that a user's hand follows (e.g. while holding the handle) during retroflection is sized to be comfortable for a user e.g. sized and/or shaped for control by user wrist movement. For example, where the contour extends to a lesser extent than that of a contour where retroflection is by only bending the first flexion joint 2350, 2450 e.g. as illustrated by dashed line contours 2411 FIG. 23E, 2411 FIG. 24A. For example where the contour extends further than that of a contour 2355, 2455 where retroflection is by only bending the second flexion joint 2352, 2452, a potential benefit being ease of accurate control of bending when the contour is of a larger extent.

Exemplary Rotational Joints

Referring back now to FIG. 4B. In some embodiments, an input arm includes one or more rotational joint which, when the arm is in a straight configuration (e.g. when flexion joints are 450, 452 are opened to 180°, e.g. as illustrated in FIG. 4B) is axially offset from one or more other rotation joint, where axially offset refers to the joints not sharing an axis of rotation.

In some embodiments, an axis of rotation 426*a* of first rotational joint 426 of first rotational joint 426 an axis of rotation of 428*a* of second rotational joint 428 have different separations from one or more flexion joint.

In some embodiments, the separation of axes of rotation 426*a*, 428*a* from flexion joint/s is in at least one direction, or in more than one direction. In some embodiments, difference in separation is in one direction only.

In some embodiments, when the arm is in a straight configuration, axis 426*a* is parallel to axis 428*b*. When rotational joints are co-axial torque applied by a user at the handle to rotate one of the rotational joints, for example, when arm portion/s between the rotational joints are in a straight configuration, tends to cause rotation of both joints. Potentially, axial offset, when the arm is in a straight configuration of enables a user holding a portion of the input arm (e.g. handle 438, e.g. with a single hand) to control (e.g. manually) position of joints individually.

Exemplary Input Arm Handle

In an exemplary embodiment, user interfaces located on an input arm handle are used to control one or more of linear motion, tool actuation and pause-resume of control for one or more surgical mechanical arm.

FIGS. 6A-B are simplified views of an input arm handle 638, according to some embodiments of the invention.

In some embodiments, handle 638 includes controls for linear movement of a surgical mechanical arm. In an exemplary embodiment, handle 638 includes a first button 682*a* to control (e.g. activate) linear advancement and a second button 682*b* (e.g. to activate) to control linear retraction of a surgical mechanical arm.

In some embodiments, handle 638 includes an user interface 682*c* which, in some embodiments, is a button, for pausing of control of a surgical mechanical arm by the input arm to which handle 638 is attached. In some embodiments, pausing is of movement of a single surgical arm, in some embodiments, pausing is of a plurality of surgical arms, e.g. two and/or all surgical arms of the system.

Figure 15:
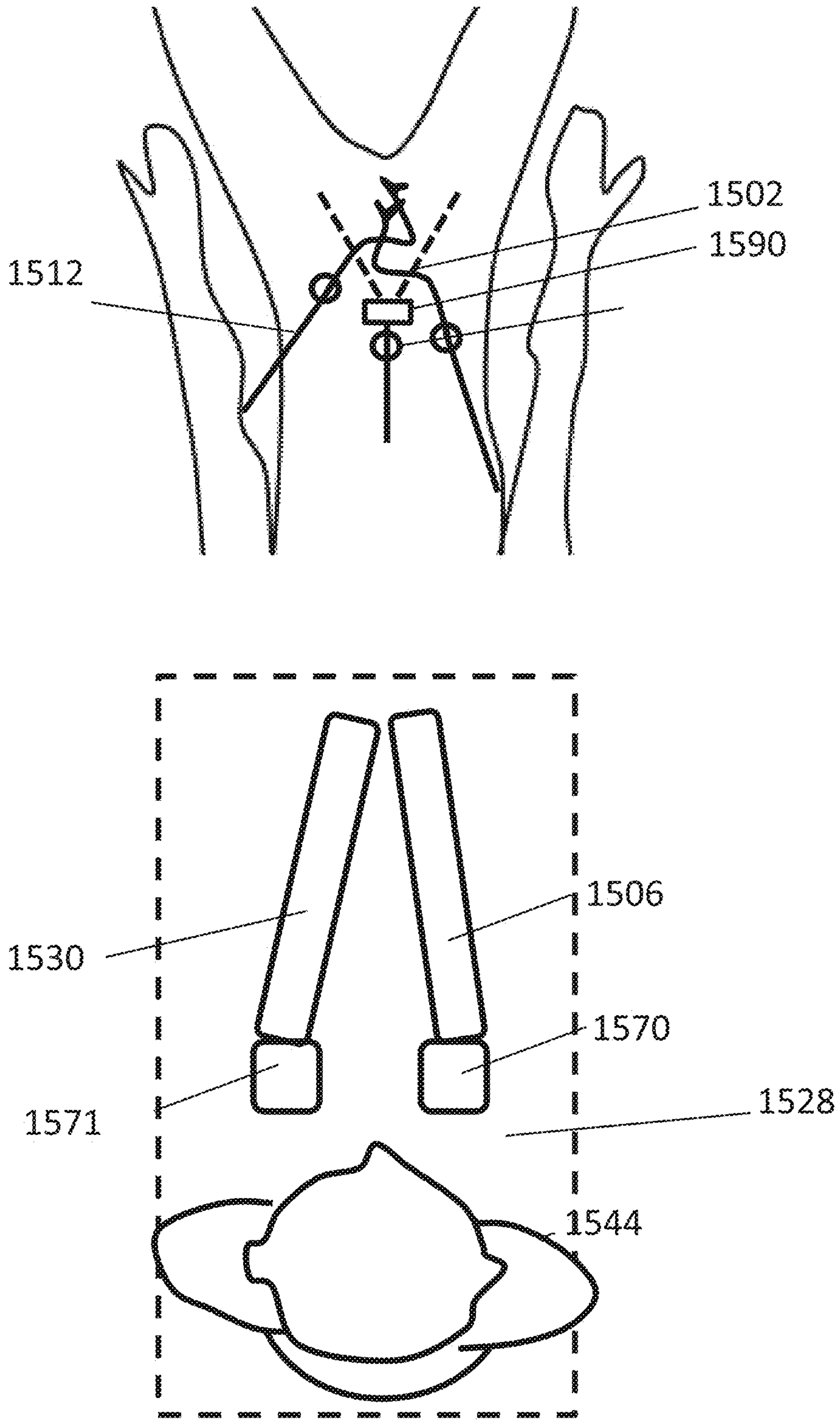
FIG. 15 is a simplified schematic of a surgical system including a control console configured for a surgical configuration where a plurality of surgical mechanical arms are inserted through a plurality of ports according to some embodiments of the invention.

In some embodiments, handle 638 includes an user interface which, in some embodiments, is a rotation knob 686, for control of rotation of a surgical mechanical device tool (e.g. tool 105 FIG. 15). In some embodiments, a user rotates the rotation knob 686 to rotate the tool.

In an exemplary embodiment, input arm handle includes a lever button 684. In some embodiments, a user presses on lever button 684 to control activation of a surgical device tool, for example, opening and/or closing of a tool (e.g. tool 105 FIG. 1). Exemplary surgical device tools include grasper, scissors. In an exemplary embodiment, a user presses on lever button 684 to open a tool and releases the button (in some embodiments, lever button 684 is protruding as illustrated in FIGS. 6A-B when in a relaxed state, e.g. in some embodiments, the lever button is spring biased to an open position).

In some embodiments, an orientation of one or more user interface is adjustable with respect to the handle. In an exemplary embodiment, an orientation of lever button 684 is adjustable with respect to handle 638. FIG. 6B illustrates a different orientation of lever button 684 than that illustrated in FIG. 6A. In some embodiments, lever button 684 freely rotates, for example, with friction under a user's thumb, e.g. as the handle is moved by the user. In some embodiments, electrical and data contacts to the lever switch are attached by a slip ring (not illustrated).

Exemplary Input Arm Configurations and Corresponding Exemplary Surgical Arm Configurations FIGS. 7-10 are exemplary simplified schematic configurations of an input arm and corresponding configurations of a surgical mechanical arm, according to some embodiments of the invention.

Figure 7:
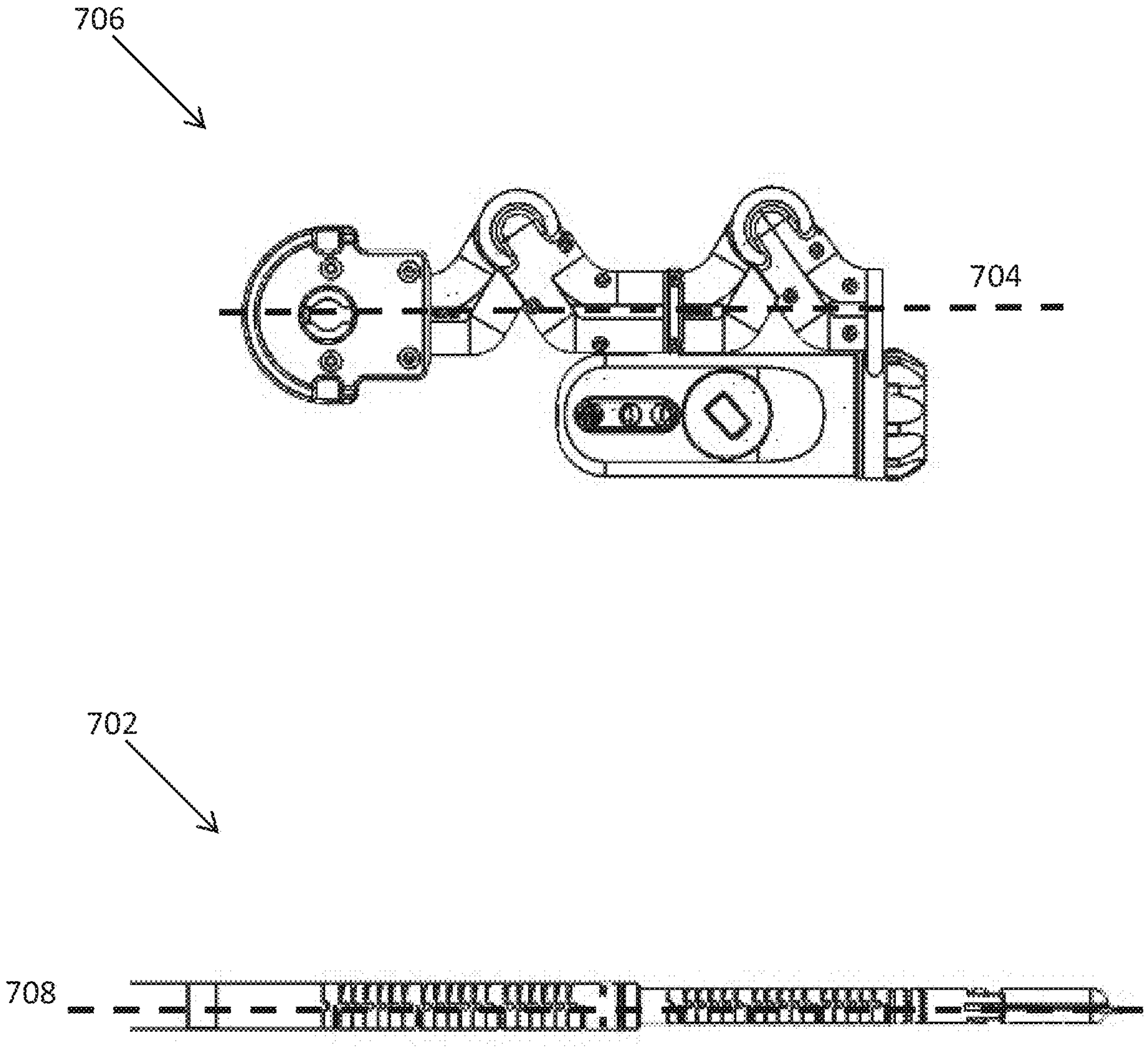
FIGS. 7, 8, 9 and 10 are exemplary simplified schematic configurations of an input arm and corresponding configurations of a surgical mechanical arm, according to some embodiments of the invention.

FIG. 7 illustrates an exemplary configuration where an input arm 706 is in a straight configuration where central long axes 704 of input arm segments are aligned and a corresponding configuration of a surgical mechanical arm 702*a*, where central long axes 708 of surgical mechanical arm flexible portions are aligned.

Figure 8:
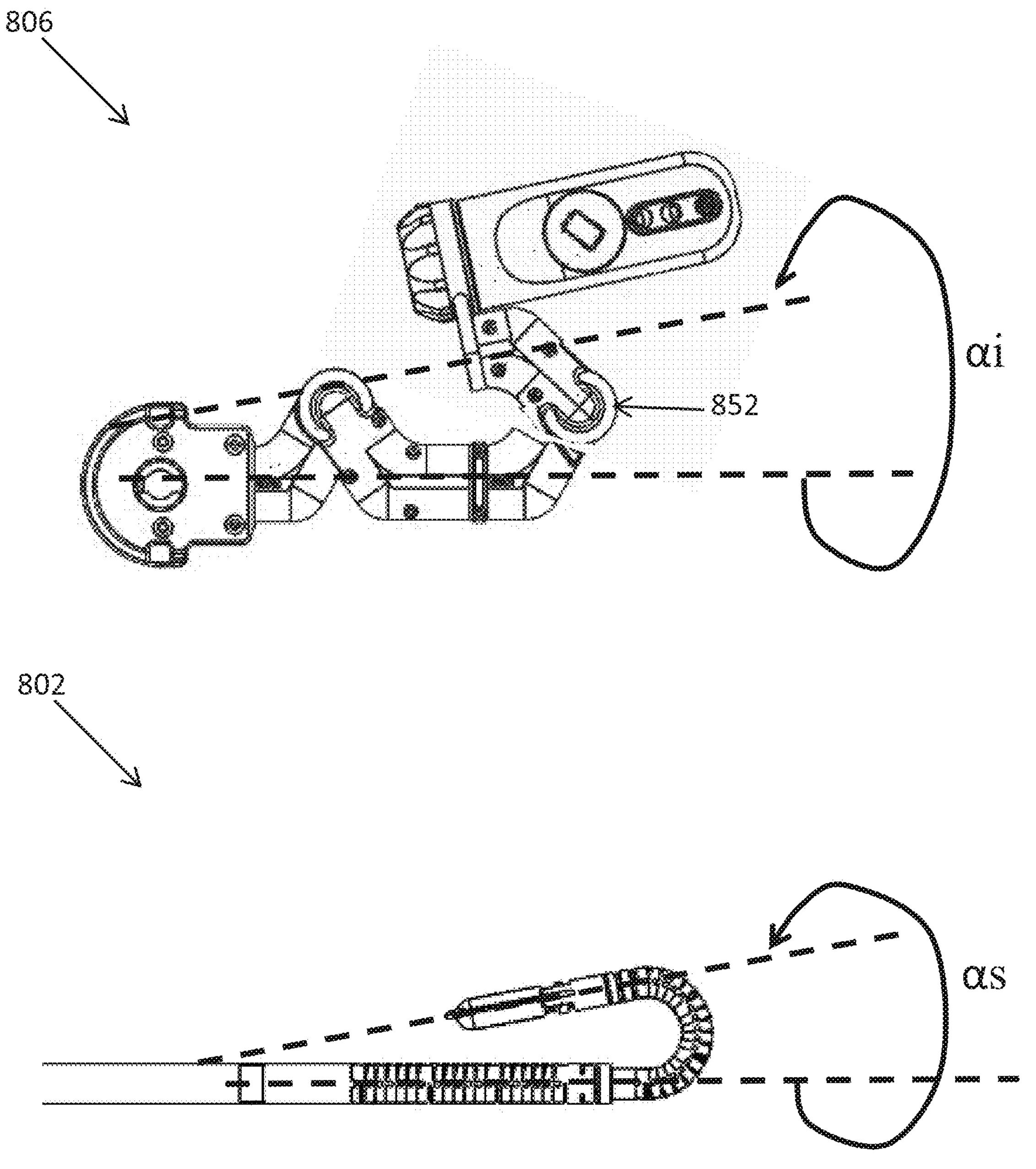

FIG. 8 illustrates an exemplary configuration where an input arm 806 is retroflected by bending at second flexion joint 852 which is fully flexed to an angle $\alpha i$. In some embodiments, angle $\alpha i$ is 100-300°, or 150-250°, or 170-220° or lower or higher or intermediate angles or ranges. In an exemplary embodiment, $\alpha i$ is about 210°. FIG. 8 illustrates an exemplary corresponding configuration of a surgical mechanical arm 802, where the surgical arm is retroflected by an angle as which corresponds to angle $\alpha i$, e.g. is the same as angle $\alpha i$ and/or is within 0-5° or 0-10° of angle $\alpha i$ and/or is within 0.1-5% of $\alpha i$, or larger or smaller or intermediate angles, ranges or percentages.

Figure 9:
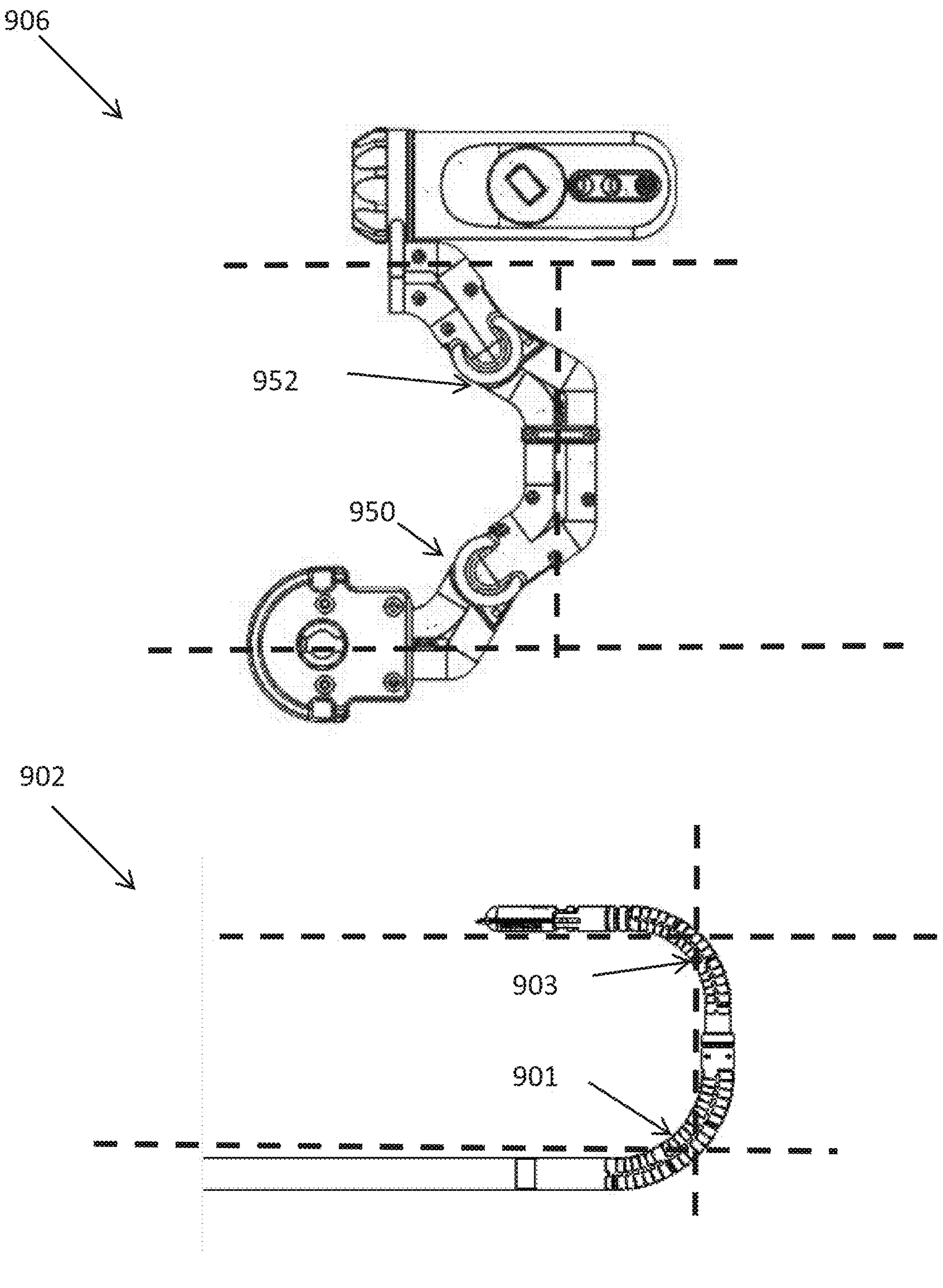

FIG. 9 illustrates an exemplary configuration where an input arm 906 is retroflected to about 180° by partial bending at first flexion joint 950 and second flexion joint 952. FIG. 9 illustrates an exemplary corresponding configuration of a surgical mechanical arm 902, which is retroflected by about 180° by partial bending of first flexible portion 901 and second flexible portion 903.

Figure 10:
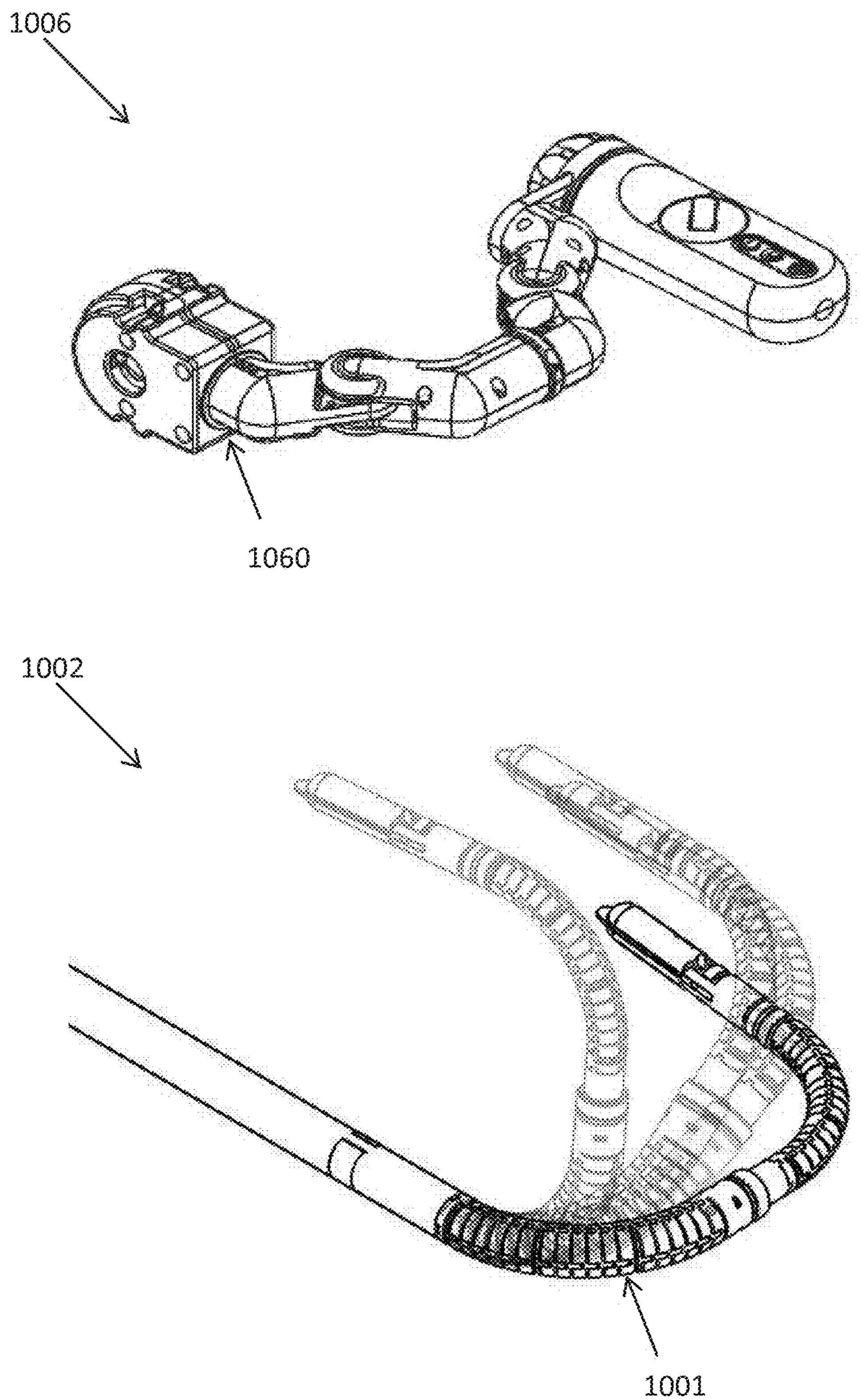

FIG. 10 illustrates rotation of an input arm 1006 about a first rotational joint 1060 and corresponding rotation of a surgical mechanical arm 1002 at a first flexible portion 1001.

Exemplary Adjustment of Exemplary Control Console

In some embodiments, position of portion/s of the control console are adjusted to enable particular configuration/s of surgical arm/s, where of surgical arm configuration (e.g. including bending angle of flexible portions and/or rotational angle at rotational joints) is based on measured configuration of the input device (e.g. including bending angle at flexion joints and/or rotational angle at rotational joints).

For example, in embodiments where surgical arms are directed towards each other, input arms are positioned such that the input arms do not interfere (e.g. touch and/or collide with) each other. For example, in some embodiments, position of attachment of two input arms to the control console is separated by a distance which is at least a sum of the lengths of the two input arms. For example, in some embodiments, input arms are positioned with different heights of attachment to the control console, for example, such that when the input arms are directed towards each other, one arm is below the other.

In some embodiments, position and/or orientation of control console portion/s (e.g. input arm/s, support/s, display/s) is adjusted for user comfort. In some embodiments, for different configurations of the input arms (e.g. oriented away or towards each other, e.g. bent or straight), position and/or orientation of attachment of input arm/s to the control console is adjusted. For example, in some embodiments, where input arms are directed towards each other, distance between attachments of the arms to the control console is increased, e.g. providing a user with more space.

In some embodiments, position of portion/s of the control console are adjusted for user comfort, for example, in some embodiments, a separation between attachment of input arms to the control console and/or between arm rest/s is selected for a comfortable separation between user arms. For example, in some embodiments, e.g. where input arms are angles away from each other and/or when the arms are bent, separation between attachment is reduced below a sum of the lengths of the input arms, e.g. closer input arms being more comfortable for a user to control (e.g. when a user controls an input arm with each user arm).

In some embodiments, positioning of the input arm/s is manual. Where, for example, a user manually moves Alternatively or additionally, in some embodiments, orienting of the input arm/s is at least partially automatic, for example where actuator/s move the input arm/s based on a signal received from a processor, where, in some embodiments, a processor generates the signal upon receiving a user input.

Exemplary Corresponding Configurations

Figure 11:
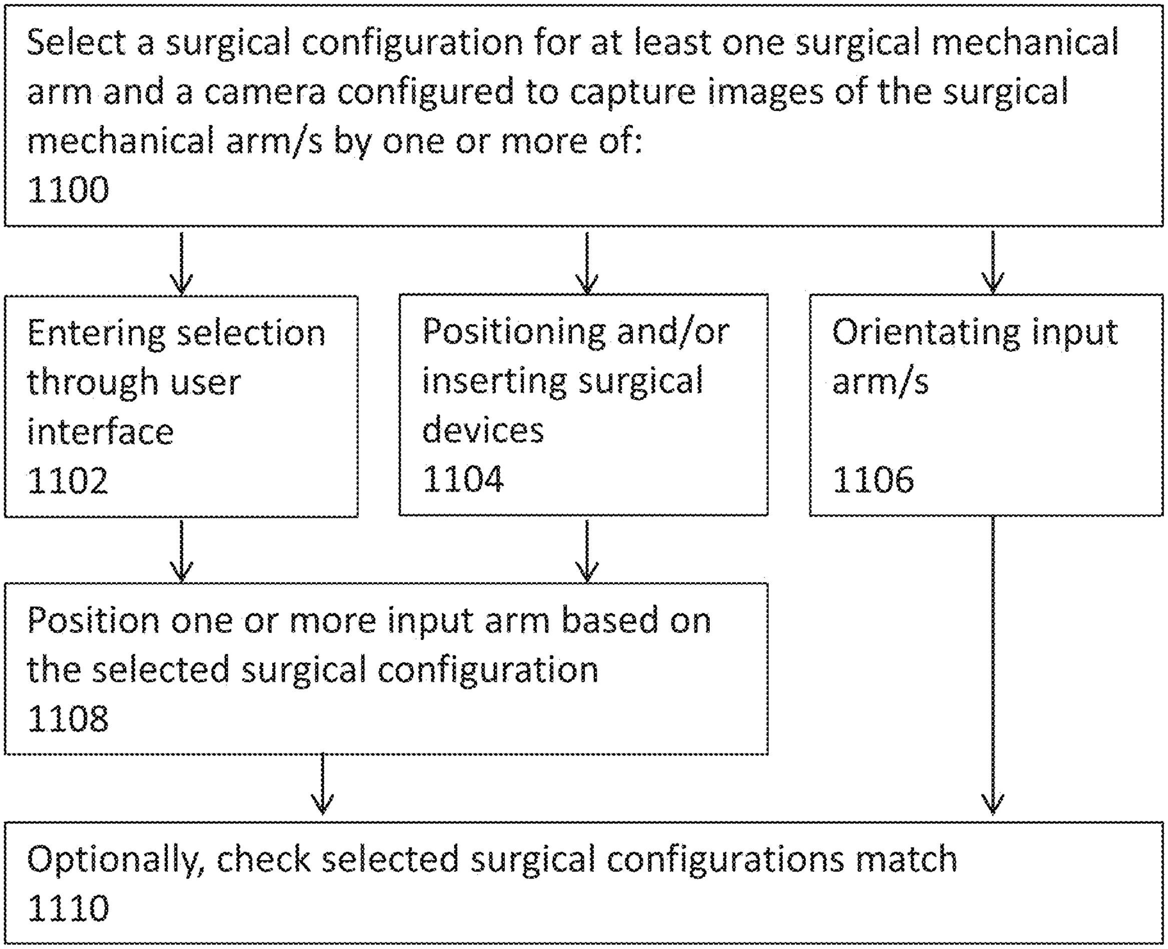
FIG. 11 is a flow chart of a method of surgical device control, according to some embodiments of the invention.

FIG. 11 is a flow chart of a method of surgical device control, according to some embodiments of the invention.

At 1100, in some embodiments, a surgical configuration is selected for a plurality of surgical devices including at least one camera. In some embodiments, a surgical configuration is selected for at least one surgical mechanical arm (e.g. two surgical mechanical arms) and a camera configured to capture images of the surgical mechanical arm/s.

In some embodiments, the surgical configuration includes laparoscopic insertion of one or more surgical device, for example, the surgical arm/s and/or camera e.g. through one or more surgical.

In some embodiments, a surgical configuration includes insertion point/s and/or region/s through which surgical devices (e.g. camera and/or surgical arm/s) are inserted. For example, including selecting a number and/or a shape and/or location of insertion points.

Exemplary insertion points include a natural body orifice, an incised opening (e.g. including an incision in a natural body orifice) and/or any other opening allowing access to the patient's body. In some embodiments, a port element (e.g. a laparoscopic port) is coupled to a patient's body at an insertion point and through which one or more surgical instrument (e.g. surgical arm, camera) accesses the patient's body.

In some embodiments, a surgical configuration includes an angle of entry of one or more surgical device into the patient, e.g. of one or more surgical arm into the patient and/or of one or more camera into the patient. For example an angle of at least a portion of surgical arm (e.g. a surgical arm rigid support portion) with respect to a surface of a patient.

An exemplary surgical configuration is, for example, where all surgical devices, e.g. one or more surgical mechanical arm and/or a camera are inserted through a single incision and/or port (e.g. single port laparoscopic surgery SILS). In some embodiments, the single port is within a natural orifice (e.g. vagina, anus, mouth, nostril, ear canal, esophagus, trachea).

A further exemplary surgical configuration is, for example, where a plurality of surgical devices are inserted through a plurality of incisions and/or ports, for example, where surgical arm/s are inserted through a different port to a camera, for example where a plurality of surgical arms are inserted through more than one port.

In some embodiments, a surgical configuration is selected by one or more of steps 1102, 1104, 1106.

At 1102, in some embodiments, a user selects one or more feature (e.g. as described regarding step 1100) of a surgical configuration through a user interface e.g. user interface 234 and/or 240 FIG. 2, e.g. display 334 FIG. 3A. In some embodiments, a user selects a surgical configuration from a set of surgical configurations e.g. stored in a memory. For example, in some embodiments, a user selects a surgical configuration from a display of surgical configuration options.

In an exemplary embodiment, the system includes two surgical configurations, a surgical configuration where a camera and at least one surgical arm are inserted into a patient in a same direction through a single incision, and a surgical configuration where the camera and at least one surgical arm are inserted into a patient in different directions through different incisions.

In some embodiments, a user enters data into the user interface and a processor receiving the data generates, from the data, a surgical configuration. For example, in some embodiments, a user selects a surgical procedure and/or enters and/or accesses information regarding a patient (e.g. imaging data). The processor then uses the entered and/or accessed data to select a surgical configuration.

At 1104, in some embodiments, a user selects a surgical configuration by positioning and/or inserting surgical devices. Where, for example, one or more sensor senses a position and/or angle of entry of the surgical devices. In some embodiments, the sensor is part of a surgical device. For example, in some embodiments, the sensor is the laparoscopic camera, and images collected by the camera e.g. of one or more surgical arm e.g. identifying a spatial relationship between the surgical arm and the camera, are used to detect a selected surgical configuration. For example, in some embodiments, a position sensor (e.g. which, in some embodiments, is part of one or more of the surgical devices) includes a position sensor e.g. sensing a spatial relationship between the surgical devices (e.g. surgical arm/s and a camera).

At 1106, in some embodiments, a user selects a surgical configuration by orientating one or more input arm. In some embodiments, a sensed orientation of the input arm (e.g. direction of extension of the input arm from a stand e.g. stand 370 FIG. 3A) is used to define one or more feature of a surgical configuration. In some embodiments, additionally or alternatively, a sensed position of a user's line of sight is used in selecting the surgical configuration. For example, in some embodiments, a position of a user's head and/or line of sight is sensed using one or more position sensor and/or using a camera (e.g. where a user's line of sight is measured by identifying facial feature/s in collected camera images). In some embodiments, a user's line of sight is inferred from collected data e.g. user height e.g. inputted by the user into the user interface.

At 1108, in some embodiments, one or more portion of a control console is positioned based on and/or corresponding to the selected surgical configuration, for example, one or more input arm (e.g. input arm/s 306, 330 FIGS. 3A-B). In some embodiments, positioning is before a start to treatment (e.g. before surgical arm/s are inserted into a patient). Optionally, in some embodiments, positioning is during a treatment e.g. as direction of surgical arm/s changes during treatment.

At 1110, optionally, in some embodiments, selected surgical configurations are compared to check that they match. For example, in some embodiments, a processor compares a surgical configuration selected at a user interface with a sensed configuration of surgical device/s and/or portion/s of the control console (e.g. of the input arm/s). In some embodiments, if a discrepancy is detected an alarm is issued (e.g. through a user interface) and/or part of the surgical system e.g. electrosurgical power e.g. actuation of surgical arms is disabled.

In some embodiments, a surgical configuration selected and the control console is configured (e.g. by adjusting the orientation of one or more input arm) before surgical devices are set up and/or treatment using surgical device/s is initiated.

In some illustrations (e.g. FIGS. 12A-16), dashed lines emanating from a camera represent a FOV of the camera.

Figure 12A:
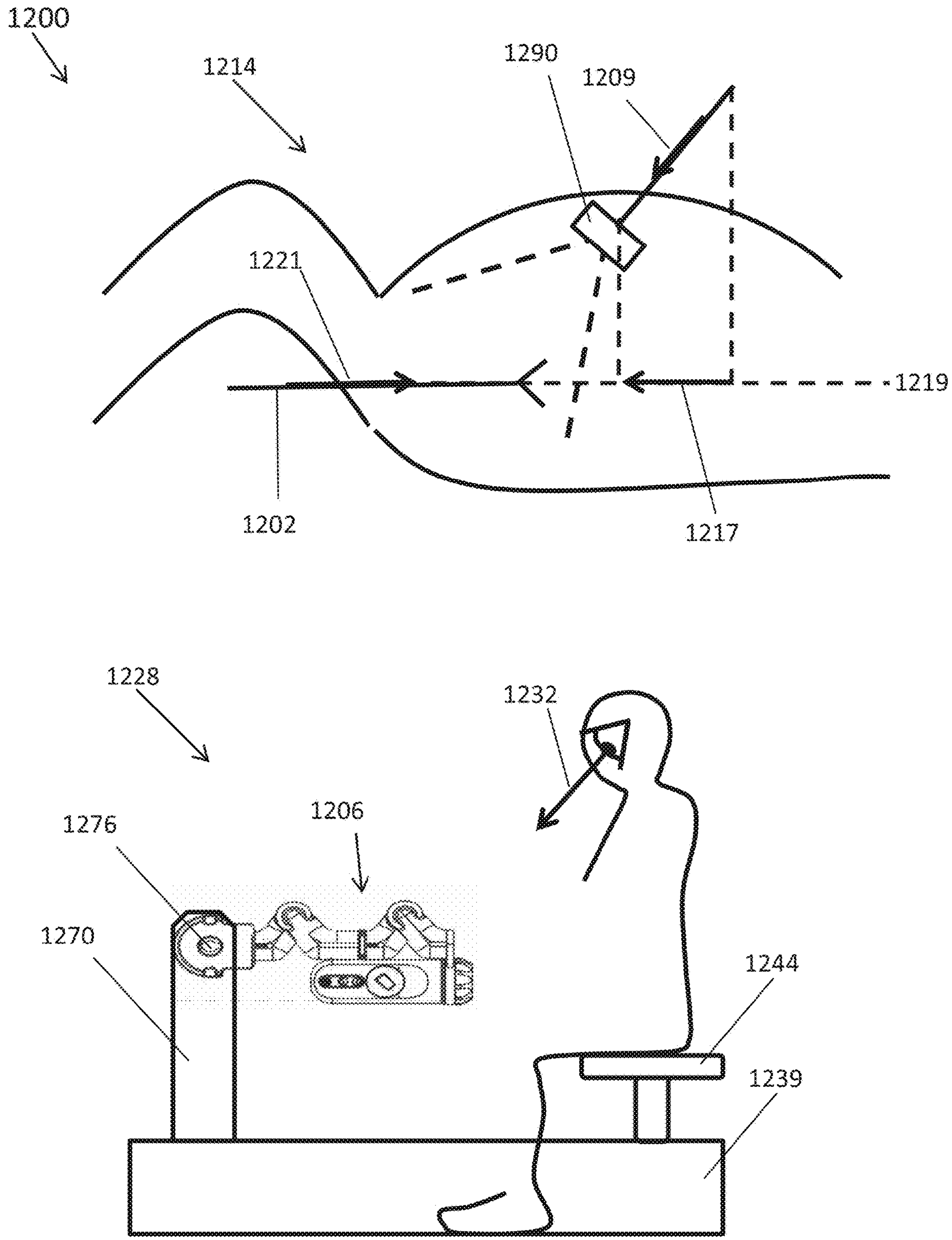
FIGS. 12A-12C are simplified schematics of a surgical system including a control console configured for a surgical configuration where a plurality of surgical devices are inserted into a patient from different directions and/or at different insertion regions, according to some embodiments of the invention.
Figure 12B:
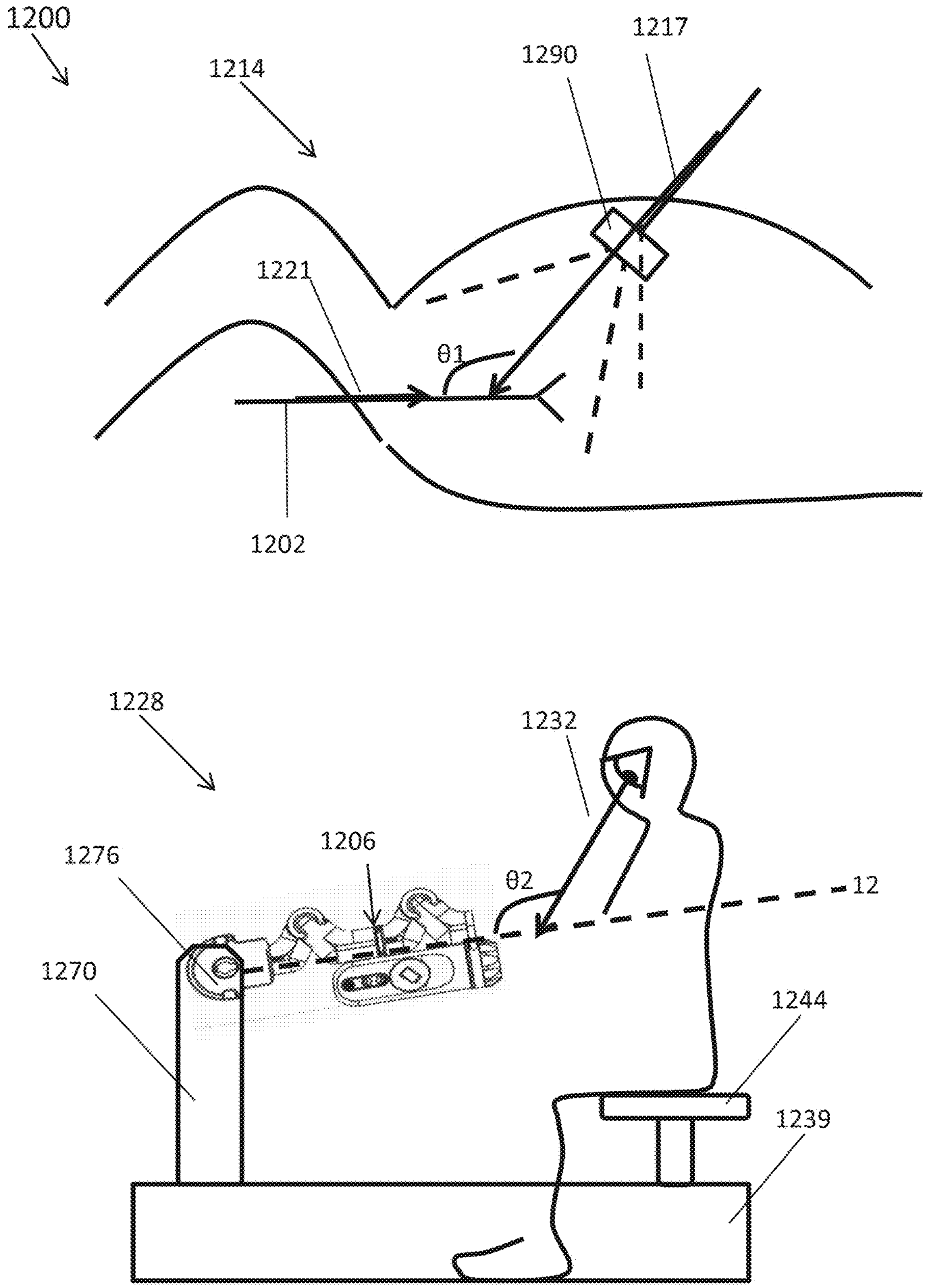
Figure 12C:
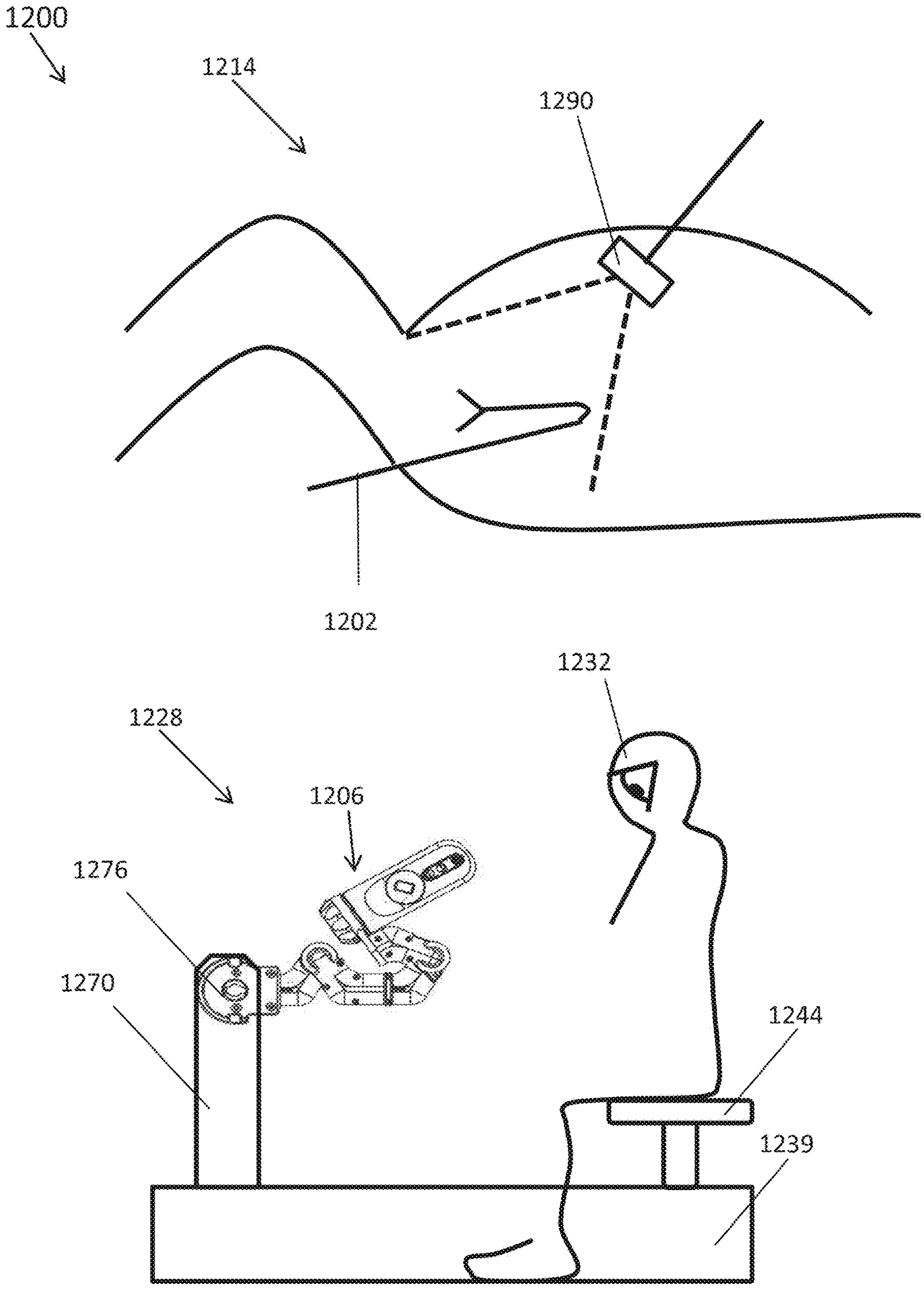

FIGS. 12A-C are simplified schematics of a surgical system including a control console 1228 configured for a surgical configuration where a plurality of surgical devices 1202, 1290 are inserted into a patient 1214 from different directions and/or at different insertion regions, according to some embodiments of the invention.

In some embodiments, at least a first and a second surgical device are inserted into patient 1214. For example, in some embodiments, the first surgical device is a camera, which is inserted and then a second surgical device, a surgical mechanical arm is inserted (or a plurality of surgical mechanical arms). In some embodiments, camera images provide feedback to a user for control of insertion of the surgical arm/s. In some embodiments, surgical arm/s are inserted until the surgical arm/s are within the camera FOV.

Alternatively, in some embodiments, surgical arm/s are inserted and then a camera is inserted.

In some embodiments, the patient's abdominal cavity is insufflated e.g. before and/or after insertion of camera 1290 and/or surgical arm 1202.

In some embodiments, a surgical mechanical arm 1202 e.g. as illustrated in FIG. 12A, is inserted through an undercarriage and/or patient's pelvic floor and/or through a natural orifice e.g. vagina, anus and the camera is inserted through an abdominal incision e.g. through the umbilicus.

In some embodiments, control console 1228 includes at least one input arm 1206 where measured movement of the input arm is used to control movement of surgical mechanical arm 1202.

In some embodiments, for example, as described regarding FIG. 11, an orientation of input arm 1206, with respect to a user's line of sight 1232 and/or with respect to a user support, corresponds with an orientation of surgical arm 1202 with respect to a camera 1290 view of surgical arm 1202.

Figure 13A:
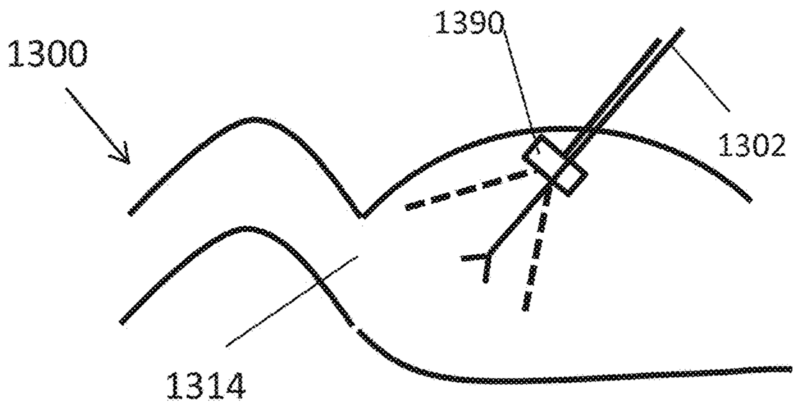
FIGS. 13A-13B are simplified schematic side views of a plurality of surgical devices inserted through the same insertion region of a patient, according to some embodiments of the invention.
Figure 13B:
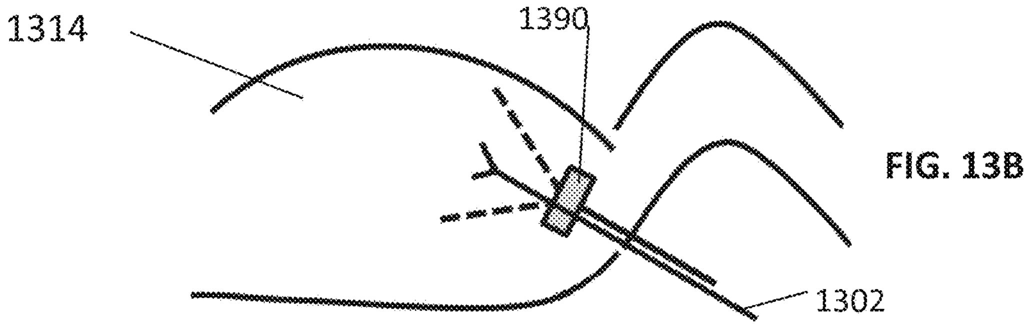
Figure 13C:
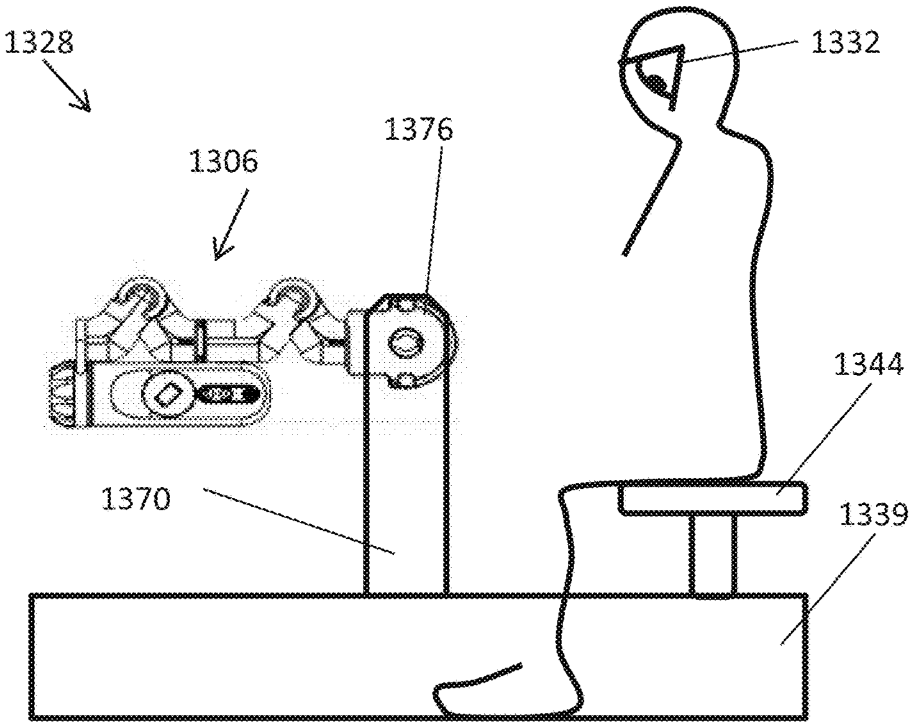
FIG. 13C is a side view of a control console configured to correspond to a surgical configuration of FIG. 13A and/or FIG. 13B, according to some embodiments of the invention.

In some embodiments, input device arm 1206 has two possible configurations. Where, for example, a first configuration illustrated in FIG. 12A is where the input arm extends towards a user where an angle of extension of a proximal portion of the input arm from a long axis of support 1270 (and/or to the vertical) is e.g. about 90°. In some embodiments, a second configuration is illustrated in FIG. 13C where an angle of extension of a proximal portion of the input arm from a support 1370 is away from the user e.g. at an angle of about 270° from the vertical and/or from a long axis of support 1370.

In some embodiments, an angle of extension of the input arm perpendicular to the vertical and/or to the long axis of support 1270 is not adjusted to correspond to the surgical configuration. For example, the angle being adjusted for user comfort and/or the input device having a fixed angle of extension e.g. for each of the two possible configurations.

In some embodiments, e.g. for selecting a corresponding input arm configuration to a surgical configuration, a vector of a direction of insertion 1209 of camera 1290 is projected onto an axis 1219 of a direction of insertion of surgical arm device 1202. In some embodiments, if the vectors of insertion 1221 of surgical arm 1202 and a projected vector 1217 of the camera are towards each other, then an input arm corresponding to the first or second surgical device is orientated towards a user, for example, in a first configuration e.g. as described above and/or as illustrated in FIG. 12A. The surgical arm insertion vector may be projected onto an axis of a direction of insertion of the camera to achieve the same result.

In some embodiments, a user manually matches the input device configuration to a surgical device configuration. Additionally or alternatively, in some embodiments, one or more sensor performs the vector analysis e.g. as described above.

In some embodiments, the input device configuration is selected based on insertion points, where, in some embodiments, for insertion through different points (e.g. different ports), the first input device configuration is selected, where the input arm extends towards the user is selected. In some embodiments, when insertion is through a same area and/or orifice and/or incision, the second input device configuration is selected, where the input arm extends away from the user (e.g. as illustrated in FIGS. 13A-C).

In some embodiments, the control console is configured by changing an orientation of an input arm support 1270 with respect to one or more user support, for example a user seat 1244 (and/or user arm rest/s which are not illustrated in FIG. 12A). In some embodiments, to configure the control console, an orientation of the input arm, e.g. an orientation of extension of the input arm from support 1270 is adjustable by moving the input arm with respect to a control console base 1229 (e.g. rotating the input arm about a joint 1276 by which it is attached to support 1270 e.g. as described regarding joint 376 FIGS. 3A, 3C).

In some embodiments, an angle in a vertical plane and/or a plane of a support 1270 long axis is based on e.g. matched to correspond to a surgical configuration. For example, as illustrated by in FIG. 12B, an angle, θ2, of extension of an input arm 1206, with respect to a user's view vector 1232 is based on an angle θ1 between a camera insertion vector 1290 and a surgical arm insertion vector 1221. In some embodiments, input arm 1206 is continuously adjustable in the vertical plane and/or a plane of a long axis of support 1270 e.g. between 90-180° of the vertical and/or a plane of a long axis of support. In some embodiments, input arm 1206 has a discrete number of configurations e.g. between 90-180° the vertical and/or a plane of a long axis of support.

In some embodiments, FIG. 12B illustrates the surgical system of FIG. 12A after retroflection of surgical arm 1202 the retroflection controlled by retroflection of input arm 1206.

In some embodiments, during use of the surgical system, the surgical arm/s moves with respect to the camera. For example, as illustrated by FIG. 12C where surgical arm 1202 has been retroflected e.g. to treat a surgical target (e.g. as described in U.S. patent application Ser. No. 15/401,045). In some embodiments, as a configuration of surgical arm 1202 is controlled and/or or matched to movement of input arm 1206, when the configuration of the surgical arm changes during use of the system, the input arm configuration continues to correspond to the surgical arm.

FIGS. 13A-B are simplified schematic side views of a plurality of surgical devices 1390, 1392 inserted through the same insertion region of a patient 1314, according to some embodiments of the invention.

FIG. 13C is a side view of a control console 1328 configured to correspond to a surgical configuration of FIG. 13A and/or FIG. 13B, according to some embodiments of the invention.

In some embodiments, e.g. as illustrated by FIG. 13A surgical mechanical arm/s 1302 and camera 1390 are inserted through an abdominal port and/or incision e.g. in the umbilicus.

In some embodiments, e.g. as illustrated by FIG. 13B, surgical mechanical arm/s 1302 and camera 1390 are inserted through the same port, for example, through a port within a natural orifice e.g. the vagina.

For example, as described above, in some embodiments, FIG. 13C illustrates a second input device configuration.

Figure 14A:
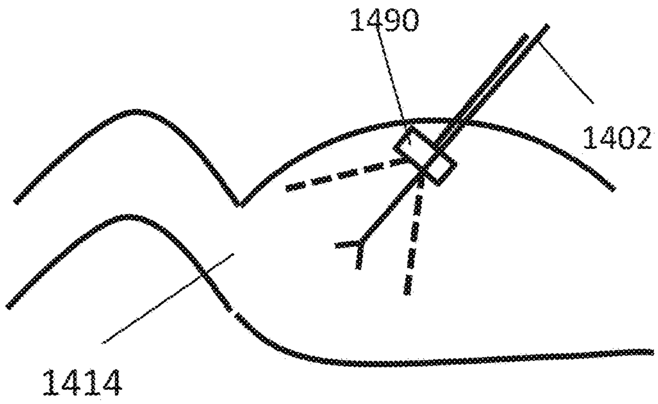
FIG. 14A is a side view of a simplified schematic of a plurality of surgical devices inserted through the same insertion region of a patient, according to some embodiments of the invention.

FIG. 14A is a side view of a simplified schematic of a plurality of surgical devices 1490, 1402 inserted through the same insertion region of a patient 1414, according to some embodiments of the invention.

Figure 14B:
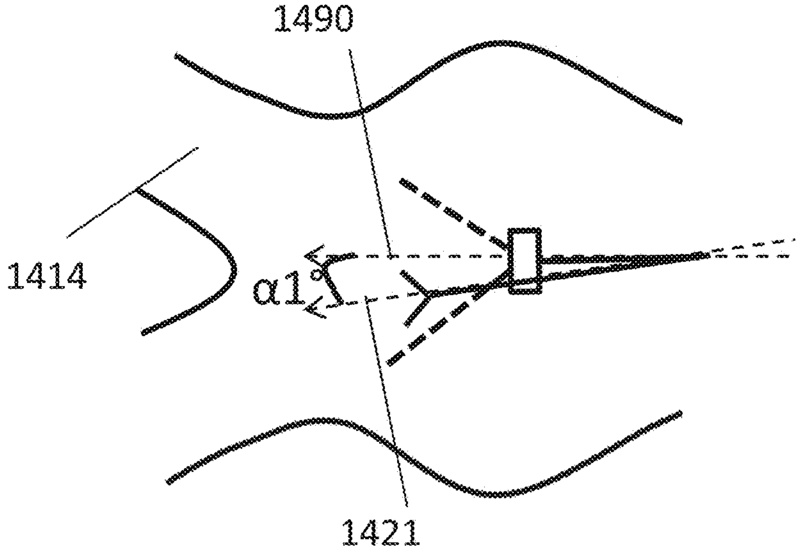
FIG. 14B is a top view of a simplified schematic of a plurality of surgical devices inserted through the same insertion region of a patient, according to some embodiments of the invention.

FIG. 14B is a top view of a simplified schematic of a plurality of surgical devices 1490, 1402 inserted through the same insertion region of a patient 1414, according to some embodiments of the invention.

Figure 14C:
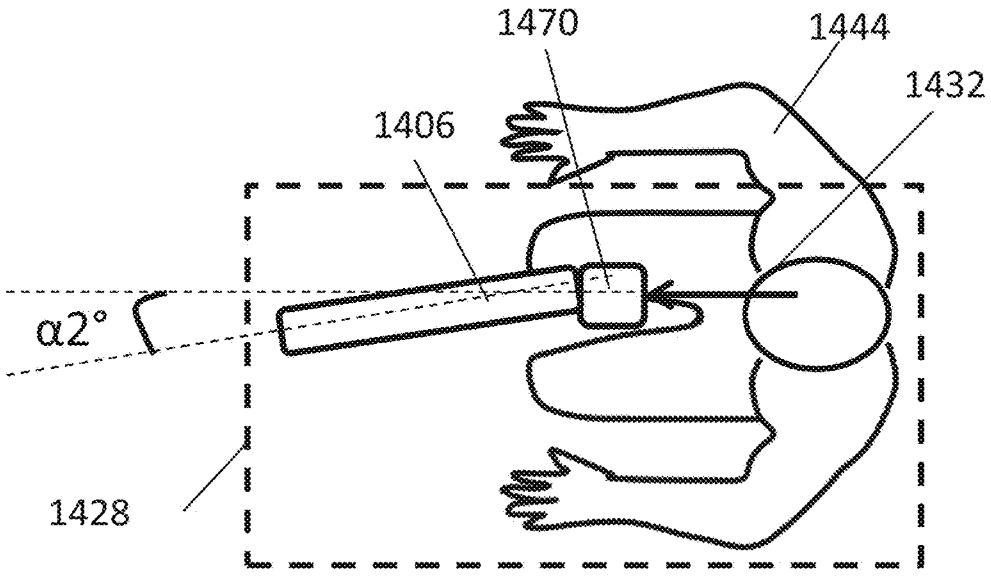
FIG. 14C is a top view of a control console configured to correspond to a surgical configuration of FIGS. 14A-14B, according to some embodiments of the invention.

FIG. 14C is a top view of a control console configured to correspond to a surgical configuration of FIGS. 14A-B, according to some embodiments of the invention.

In some embodiments, an angle in a horizontal plane and/or a plane perpendicular to a support 1470 long axis is based on e.g. matched to correspond to a surgical configuration. For example, as illustrated by in FIG. 14C, an angle, α2°, of extension of an input arm 1406, with respect to a user's view vector 1432 is based on an angle α1° between a camera insertion vector 1490 and a surgical arm insertion vector 1421. In some embodiments, input arm 1406 is continuously adjustable in the horizontal plane and/or a plane perpendicular to a long axis of support 1470 e.g. between 90-180°. In some embodiments, input arm 1206 has a discrete number of configurations e.g. between 90-180°.

FIG. 15 is a simplified schematic of a surgical system including a control console 1528 configured for a surgical configuration where a plurality of surgical mechanical arms 1502, 1512 are inserted through a plurality of ports according to some embodiments of the invention. In some embodiments, ports are illustrated as circles.

In some embodiments, an orientation of input arms 1506, 1530 with respect to a user (e.g. sitting on seat 1544) and/or with respect to the control console, is based on general direction of approach of a surgical mechanical arm through a port and/or into a patient. For example, as illustrated in FIG. 15, surgical mechanical arms 1502, 1512 are inserted through ports and directed towards each other (e.g. to approach a surgical target) and input arms 1506, 1530 are angled towards each other. In some embodiments, e.g. as described with respect to FIGS. 14A-C, angles of extension of input arm/s 1530, 1506 are based on (e.g. matched to correspond to) angles of insertion of surgical arms 1502, 15 with respect to an angle of insertion of camera 1590.

Figure 16:
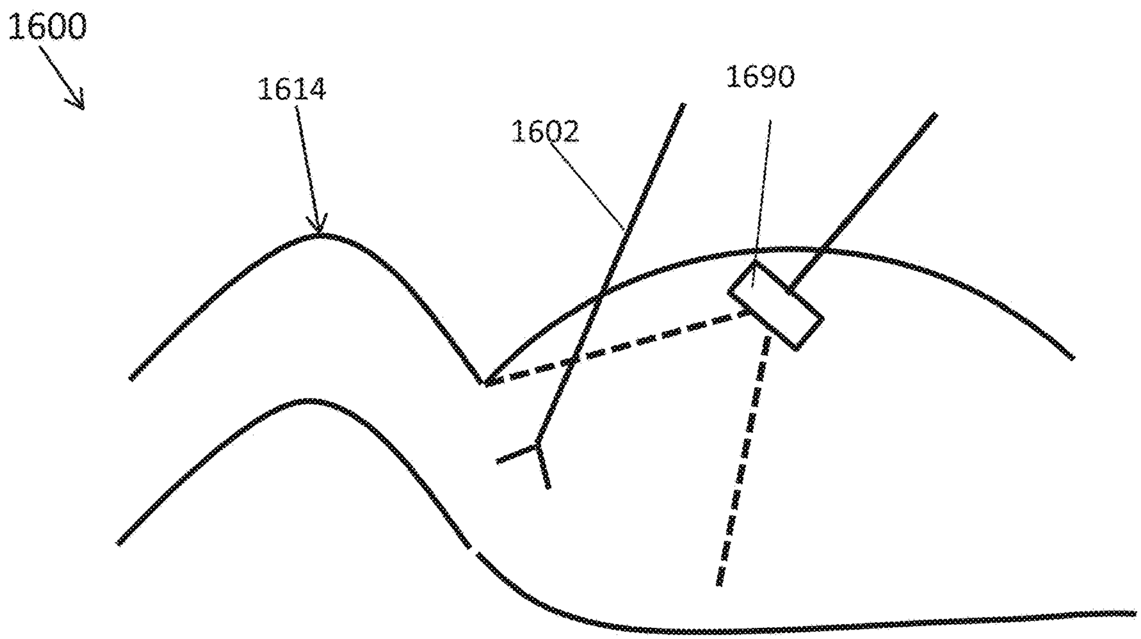
FIG. 16 is a simplified schematic of a surgical system including a control console configured for a surgical configuration where a plurality of surgical devices are inserted into a patient at different insertion regions, according to some embodiments of the invention.
Figure 16:
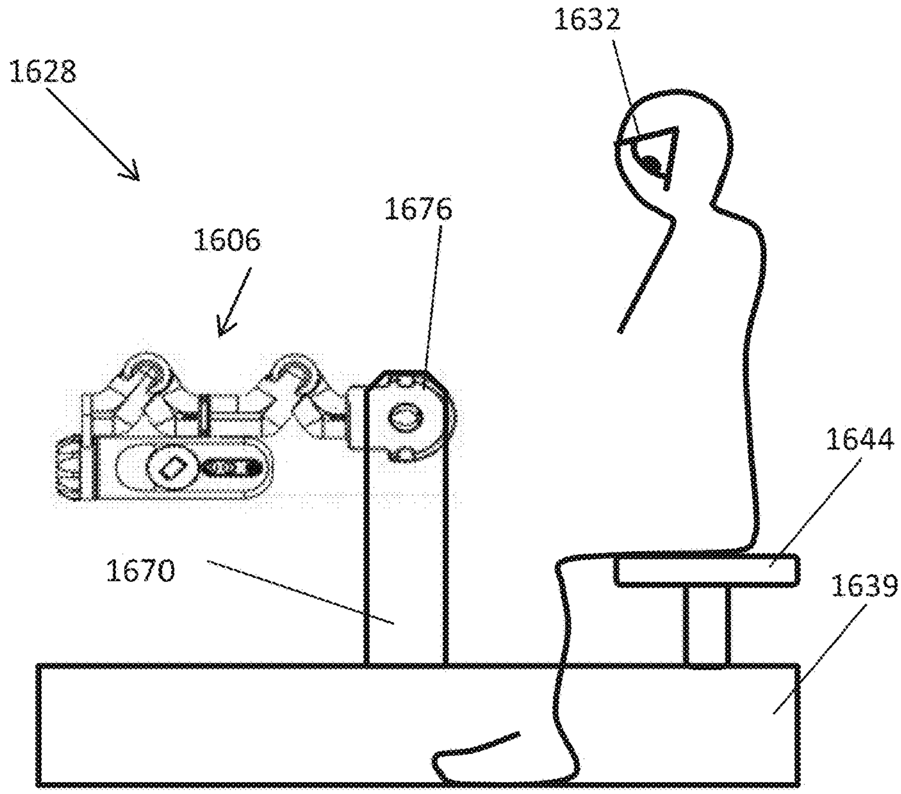

FIG. 16 is a simplified schematic of a surgical system including a control console 1628 configured for a surgical configuration where a plurality of surgical devices 1202, 1290 are inserted into a patient 1214 at different insertion regions, according to some embodiments of the invention. In some embodiments, camera 1690 is inserted through a different insertion point than surgical arm/s 1602 but the devices 1690, 1602 extend in the same general direction (e.g. a vector of insertion of one of the devices projected onto an axis of the vector of insertion of the other device are not directed towards each other, are directed in the same direction). In some embodiments, input arm 1628 extends away from user 1632, when different entrance points and/or ports are used for camera 1590 and surgical arm/s 1602.

Figure 17A:
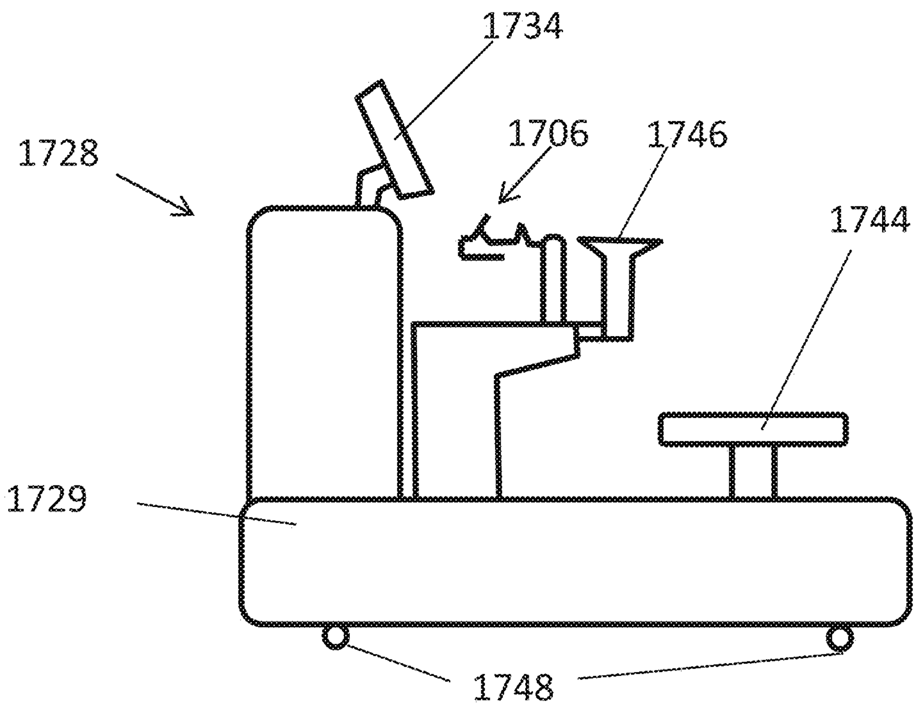
FIG. 17A is a simplified schematic of a control console where an input arm is orientated in a forwards configuration, according to some embodiments of the invention.

Exemplary Adjusting of Exemplary Control Console for Exemplary Corresponding Configurations FIG. 17A is a simplified schematic of a control console 1728 where an input arm 1706 is orientated in a forwards configuration, according to some embodiments of the invention.

Figure 17B:
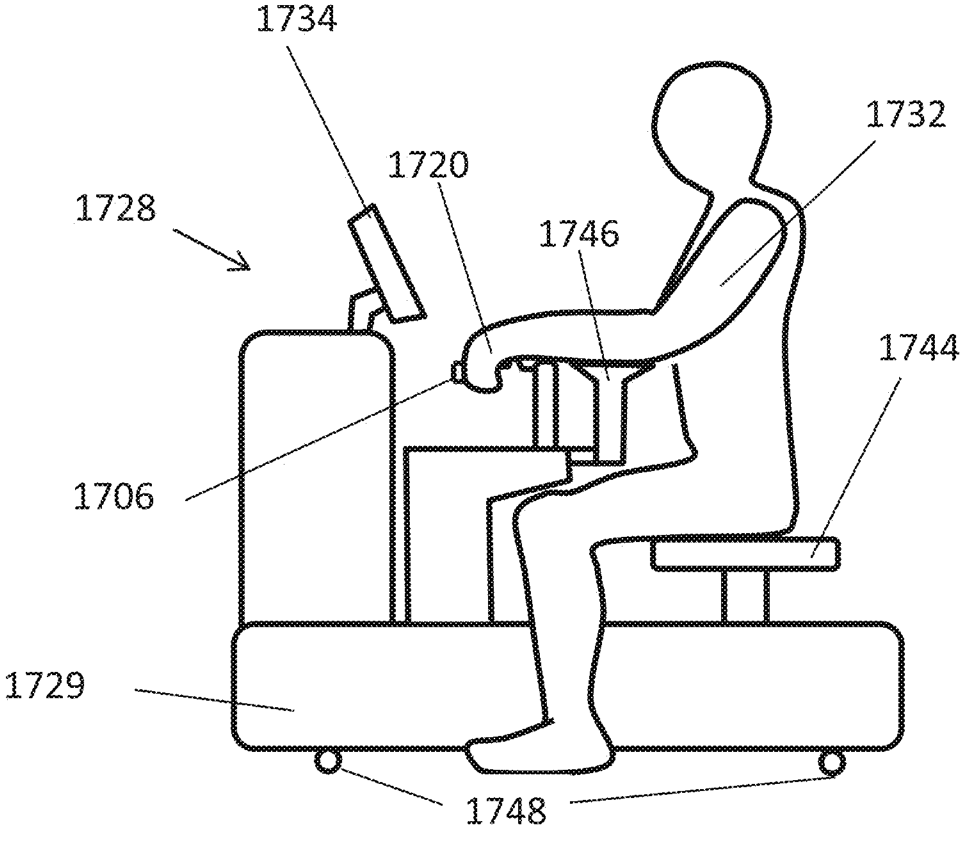
FIG. 17B is a simplified schematic of a user using a control console where an input arm is orientated in a forwards configuration, according to some embodiments of the invention.

FIG. 17B is a simplified schematic of a user 1732 using a control console 1728 where an input arm 1706 is orientated in a forwards configuration, according to some embodiments of the invention.

Figure 18A:
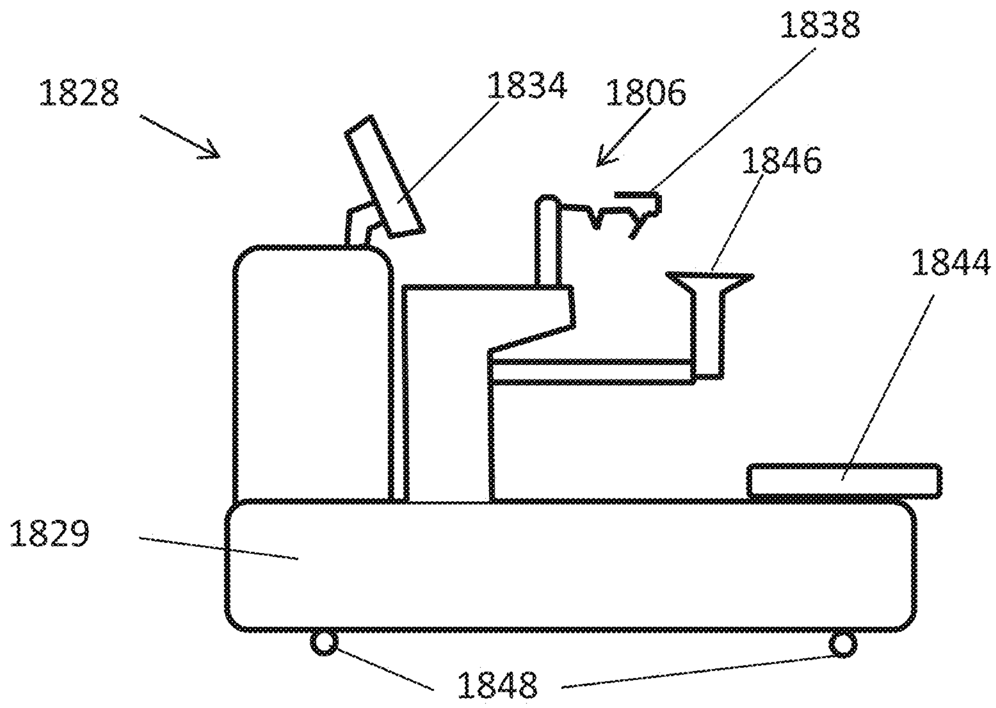
FIG. 18A is a simplified schematic of a control console where an input arm is orientated in a backwards configuration, according to some embodiments of the invention.

FIG. 18A is a simplified schematic of a control console 1828 where an input arm 1806 is orientated in a backwards configuration, according to some embodiments of the invention.

Figure 18B:
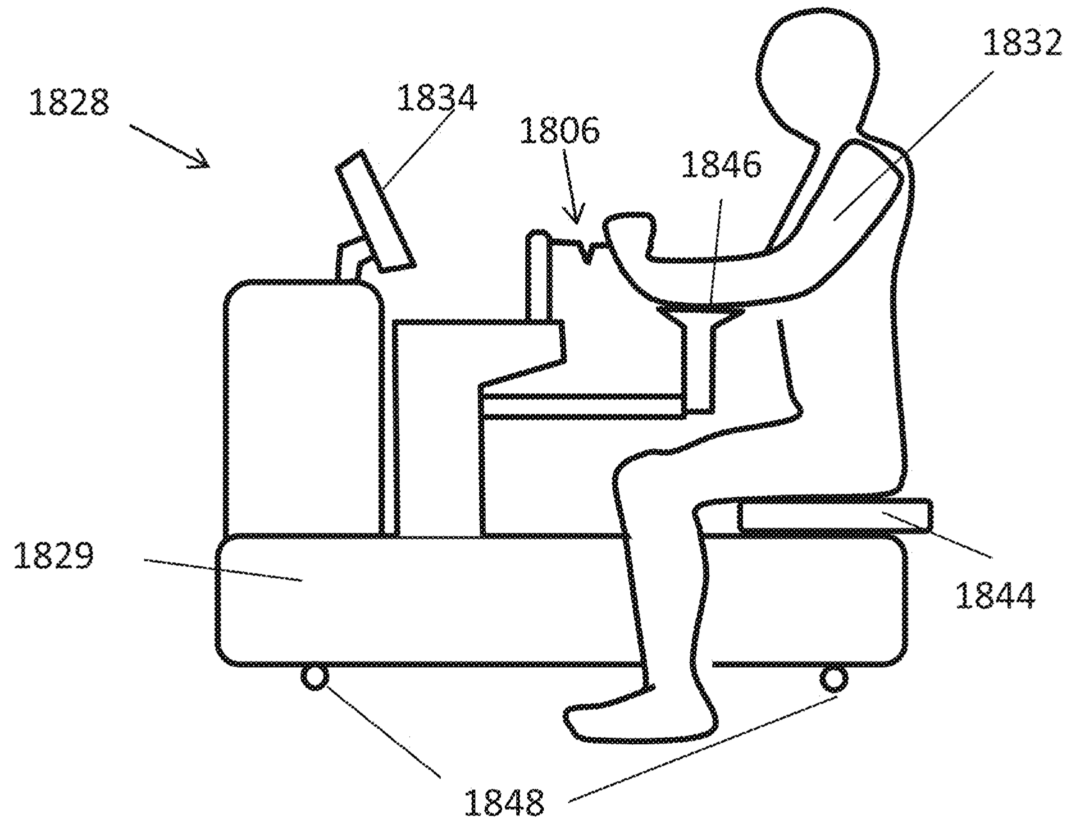
FIG. 18B is a simplified schematic of a user using a control console where an input arm is orientated in a backwards configuration, according to some embodiments of the invention.

FIG. 18B is a simplified schematic of a user 1832 using a control console 1828 where an input arm 1806 is orientated in a backwards configuration, according to some embodiments of the invention.

In FIGS. 17A-B and 18A-B a single input arm (1706, 1806) is visible, however, in some embodiments, (e.g. as illustrated in FIGS. 3A-B), control console 1728 includes more than one input arm, for example, two input arms. In some embodiments, movement and/or orientation of input arm 1706, 1806 (e.g. as described below) is performed for additional input arm/s (e.g. a second input arm), simultaneously and/or sequentially and/or alternatively to movement with input arm 1706, 1806.

In some embodiments, a user adjusts one or more portion of a control console. In an exemplary embodiment, when orientation of input arm/s is changed e.g. for a different surgical configuration e.g. as described regarding step 1908, FIG. 19 and/or FIGS. 17A-B, and/or one or more portion of a control console is adjusted. For example, as described regarding step 1910 of FIG. 19.

In some embodiments, one or more adjustment of the control console is illustrated by changes illustrated between FIGS. 17A-B and FIGS. 18A-B.

For example, in some embodiments a height of one or more portion of the control console is adjusted, e.g. a height of the portion from the ground and/or height of the portion with respect to one or more other components of the control console e.g. with respect to the input arm 1706, 1806. For example, in some embodiments, a height of a seat 1744, 1844 and/or arm rest/s 1746 and/or a display 1734, 1834 is adjusted.

For example, in some embodiments, lateral position of one or more portion of the control console is adjusted, e.g. a position of the portion with respect to the input arm/s 1706, 1806. For example, in some embodiments, a lateral position of a seat 1744, 1844 and/or arm rest/s 1746 and/or a display 1734, 1834 is adjusted.

Exemplary User Control of Exemplary Input Arm

In some embodiments, a user controls an input by grasping a 1722 handle of input arm 1706. In an exemplary embodiment, when input arm/s 1706 are moved from a forwards position (e.g. illustrated by FIG. 17A-B) to a backwards position (e.g. as illustrated by FIG. 18A-B) a position of a handle 1738 of the input arm moves in a direction towards a user (user direction) and/or away from display 1734 and moves to a position lower (e.g. with respect to the ground). In some embodiments, for example, potentially improving comfort for a user one or more of arm rest/s 1746 and/or seat 1844 and/or display 1824 are moved lower and/or towards in a user direction. In some embodiments, an angle of display 1824 is changed, for example with respect to an attachment of the display to the control console.

In some embodiments, one or more of display 1734, input arm 1706 (and, in some embodiments, additional input arm/s), arm rest 1746 (and, in some embodiments, additional arm rest/s, e.g. in some embodiments, control console includes an arm rest for each input arm), and seat 1744 are mounted to a base 1739 and/or are moveable (e.g. with respect to the base) on horizontal and/or vertical rails e.g. disposed within and/or mounted on the base. In some embodiments, one or more component is released to effect upwards vertical movement (e.g. is biased by a gas spring) and/or downwards force is exerted to effect downwards vertical movement (and/or to lower the component onto base 1729, 1829). Alternatively or additionally, in some embodiments, one or more component (e.g. seat) is attached to the base by a screw attachment and vertical movement is effected by rotating the component. In some embodiments, a component (e.g. seat 1744) is locked into a desired position.

Exemplary Controlled Retroflection of Input and Surgical Arms

In some embodiments, one or more portion of a control console is adjusted during a surgical procedure. For example, in some embodiments, an angle of connection of an articulated input arm configured to control movement of a surgical mechanical arm, with respect to a support is changed. In some embodiments, the input arm is used to retroflect the surgical arm, within a patient's body, an angle of connection of the input arm to a support is then changed, without moving the surgical arm (e.g. control is paused). Optionally, in some embodiments, position of one or more portion of a control console to which the input arm is attached is changed, e.g. a position of a seat and/or a position of arm rest/s and/or a position of one or more display. In some embodiments, after change of angle of the input arm and/or position of control console portion/s are changed, control of surgical arm movements by the input arm are resumed.

Figure 19:
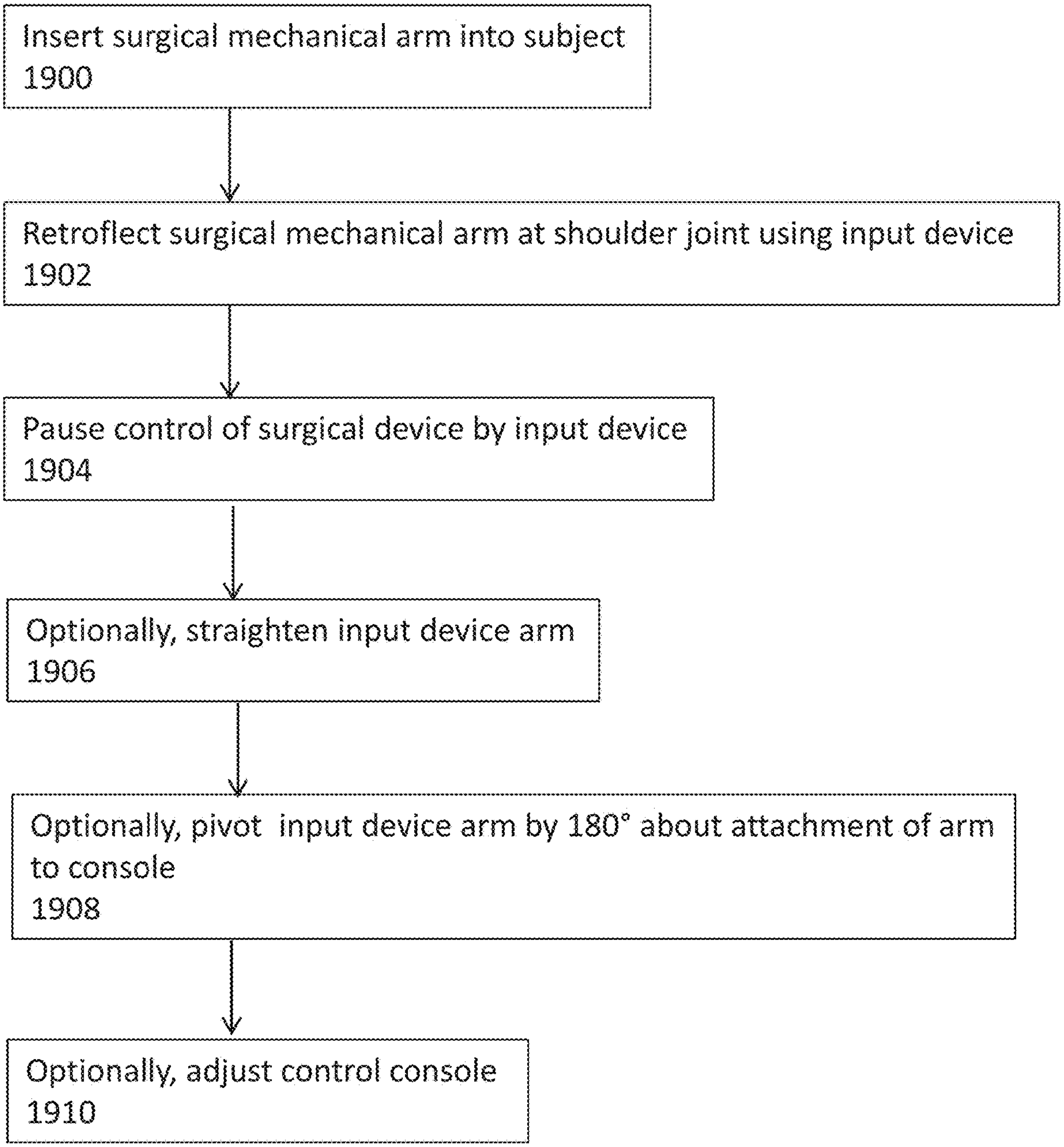
FIG. 19 is a flow chart of a method of surgical mechanical arm movement control, according to some embodiments of the invention.

FIG. 19 is a flow chart of a method of surgical mechanical arm movement control, according to some embodiments of the invention. In some embodiments, the steps of the flow chart of FIG. 19 are performed using a single input arm to control movement of a single surgical mechanical arm. Alternatively, in some embodiments, more than one input arm is used in control and/or more than one surgical mechanical arm is controlled. The steps of the flow chart of FIG. 19 are performed by movement of a first input arm to control movement of a first surgical mechanical arm and by movement of a second input arm to control movement of a second surgical mechanical arm where control of the arms (e.g. insertion and/or retroflection) is simultaneous and/or sequential and/or alternating.

At 1900 a surgical mechanical arm is inserted into a subject. In some embodiments, the surgical mechanical arm is inserted manually. In some embodiments, a user controls automated insertion of the surgical mechanical arm. For example, in some embodiments, a user inputs control instructions through one or more user interface to control linear movement of the surgical mechanical arm (e.g. buttons 682*a*, 682*b* FIGS. 6A-B). Where linear movement, is for example, effected by one or more actuators (actuation of linear movement of the surgical mechanical arm e.g. as described in U.S. patent application Ser. No. 15/501,862).

In some embodiments, insertion of the mechanical arm is partially manual and partially automated. For example, a user positioning and/or partially inserting the surgical mechanical arm, with further insertion being automated.

At 1902 the surgical mechanical arm is retroflected.

In some embodiments, surgical mechanical arm is retroflected by bending at a first flexible portion (e.g. first flexible portion 101 FIG. 1). For example, where bending is controlled by a user bending a first flexion joint of an input device e.g. 350 FIGS. 3A-I, 550 FIG. 5.

In some embodiments, surgical mechanical arm is retroflected by bending at a second flexible portion where, in some embodiments, bending is controlled by a user bending a first flexion joint of an input device. For example, as illustrated in FIG. 8.

In some embodiments, surgical mechanical arm is retroflected by bending at a first flexible portion and a second flexible portion, where, in some embodiments, bending is controlled by a user bending a first and a second flexion joint of an input device. For example, as illustrated in FIG. 9.

In some embodiments, steps 1900 and 1902 occur, concurrently, at least partially. For example, in some embodiments, the surgical mechanical arm is inserted as it is retroflected, e.g. linear advancement movements alternating with bending at one or more surgical mechanical arm flexible portion and/or linear advancement movements occurring concurrently with bending at one or more surgical mechanical arm flexible portion.

At 1904, in some embodiments, control of movement of the surgical mechanical arm is paused. For example, in some embodiments, a user enters a pause instruction through a user interface (e.g. by pressing on button 682*c* FIG. 16)

At 1906, in some embodiments, optionally, the input arm is straightened.

At 1908, in some embodiments, an angle of the input arm with respect to a control console to which it is attached is changed. For example, in an exemplary embodiment, the input arm is rotated about a joint (e.g. stand connection joint 376 FIG. 3D) from a first position where a direction of the arm is generally extending towards a user to a second positon where the arm is generally extending away from a user. In some embodiments, the input arm is rotated by 180°.

At 1910, in some embodiments, portion/s of the control console are adjusted for use of the input arms in the second position. For example, position of one or more of arm rests (e.g. 346 FIG. 3A), a seat (e.g. 344 FIG. 3A), a display (324 FIG. 3A).

In some embodiments the order of steps 1906, 1908 and 1910 is interchangeable.

Exemplary User Control of Exemplary Input Arm

FIG. 20 is a simplified schematic of a user 2032 manipulating an input arm 2006, according to some embodiments of the invention.

In some embodiments, user 2032 holds a handle 2038 between one or more a finger 2032*f* (some fingers are not visible in FIG. 20) and a thumb 2032*t*. In some embodiments, a user holds handle 2038 in a tripod grasp and/or in a prismatic finger grasp (e.g. similar to grasps associated with holding an elongated writing implement). In some embodiments, a user grasps the handle in a palmar grasp e.g. wrapping fingers and the thumb around a length of the handle.

In some embodiments, handle 2038 is sized and/or shaped for a user to comfortably hold the handle between an adult finger and thumb (e.g. in a tripod and/or prismatic grasp) and/or for a user to grasp the handle (e.g. in a palmar grasp). For example where an average width (e.g. diameter) is 2 mm-150 mm, or 5 mm-100 mm, or 10-50 mm, or 20-60 mm, or about 40 mm, or lower or higher or intermediate dimensions or ranges. In some embodiments, handle 2038 is elongate, for example, with a length which enables grasp/s described above. For example with a long axis length of 10-300 mm, or 20-200 mm, or 50-150 mm, or 70-130 mm or 90-130 mm, or 100-120 mm, or about 110 mm or lower or higher or intermediate lengths or ranges. In some embodiments, handle 2038 has a generally cylindrical shape.

In some embodiments, a user holds handle 2038 such that a user thumb 2032*t* is positioned over a user interface 2084 (e.g. a lever button, e.g. 384 FIG. 3D, 684 FIGS. 6A-B). In some embodiments, handle 2084 includes a plurality of user interfaces 2082 are positioned on the handle such that a user is able to control the plurality of user interfaces with the user's thumb e.g. without changing user grasp on the handle.

In some embodiments, handle 2038 is configured (e.g. sized and/or shaped) such that a user with a thumb at user interface 2084 is able (e.g. concurrently) to control a user interface 2086 disposed at an end (e.g. proximal end) of the handle (e.g. 386 FIG. 3D, 686, FIGS. 6A-B). For example, using a user's finger e.g. without changing user grasp on the handle and/or while the user's thumb remains in a region of user interface 2084. Where, for example, dial user interface 2086 is 10-150 mm, or 10-100 mm or 10-50 mm or lower or higher or intermediate distances from user interface 2084.

In some embodiments, user 2032 supports a second flexion joint 2052 in the user's palm e.g. as illustrated in FIG. 20. Potentially, this grasp enables the user to control position of both second flexion joint 2052 and a first flexion joint 2050, e.g. by force exerted by the user at the handle (e.g. with the user's finger/s and/or thumb) and/or at the first flexion joint (e.g. with the user's palm).

In some embodiments, one or more input arm user interface is used to control a surgical mechanical arm, e.g. actuation of an arm tool e.g. opening and/or closing of a tool (e.g. gripper, scissors e.g. 105 FIG. 1), for example, as described regarding FIG. 3F. Alternatively or additionally, in some embodiments, input device user interface/s are used to control other portions of the system, for example, the display of the control console (e.g. display 334 FIG. 3A).

In some embodiments, input arm and/or control console user interfaces control linear movement of the surgical arm (e.g. into and/or out of a patient) and/or pausing and/or resuming of control of movement of the surgical arm by the input arm. e.g. as described regarding user interfaces 682*a-c* FIG. 6A.

In some embodiments, handle 2038 includes one or more finger loop, through with a user inserts a finger, e.g. as described and/or illustrated regarding loop 380 FIG. 3D.

General

It is expected that during the life of a patent maturing from this application many relevant control consoles for surgical systems will be developed and the scope of the terms control console, input arm, surgical mechanical arm is intended to include all such new technologies a priori.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A control console for control of a surgical arm comprising:

a control console base defining a distal end and a proximal end;

at least one user support coupled to said base between said distal end and said proximal end of said base;

at least one input arm support coupled to said base distally to said at least one user support, said at least one input arm support defining a vertical long axis; and at least one input arm comprising a plurality of sections sequentially coupled by joints and extending between a first input arm end which is coupled to said input arm support and a second input arm end which includes a handle section; wherein an orientation of said plurality of sections relative to said at least one input arm support is adjustable on a plane that is perpendicular to said vertical long axis of said input arm support, such that the handle section may assume at least a first position in which the handle section is more proximal to the user support than said input arm support, and at least a second position, in which the handle section is more distal to the user support than said input arm support;

wherein, in said first position, said at least one input arm is configured for controlling the surgical arm when the surgical arm is in retroflection, and in said second position, said at least one input arm is configured for controlling the surgical arm when the surgical arm is not in retroflection;

wherein during manipulation of said input arm by a user for controlling movement of the surgical arm, said handle section is configured to remain directed towards said at least one user support under all adjustments, including said first position and said second position.

2. The control console according to claim 1, wherein said input arm is attached to said input arm support via a joint which enables said adjustment in orientation.

3. The control console according to claim 1, wherein said input arm is configured to extend at an angle of between 90-270 degrees relative to said vertical long axis of said input arm support.

4. The control console according to claim 1, wherein said at least one user support comprises one or more of an arm rest and a user seat.

5. The control console according to claim 1, wherein said handle section is shaped and sized for gripping by a user's hand and comprises one or more user interfaces including buttons, switches, levers, dials.

6. The control console according to claim 1, wherein said handle section is connected to one of said plurality of input arm sections via one or both of a bendable joint and a rotational joint.

7. The control console according to claim 1, wherein said handle section is rotatable about a handle section long axis.

8. The control console according to claim 1, wherein said input arm comprises a discrete number of orientations relative to said input arm support.

9. The control console according to claim 1, comprising a screen display configured to one or both of provide input to a user and receive input from the user.

10. The control console according to claim 1, comprising a processor configured to receive data regarding a selected surgical configuration of said surgical arm and to set said orientation of said input arm relative to said input arm support to match said selected surgical configuration.

11. The control console according to claim 10, wherein said selected surgical configuration includes a location of at least one insertion point of said surgical arm into the body, and a direction of extension of said surgical arm relative to a field of view of a camera.

12. The control console according to claim 1, wherein said handle section comprises at least one sensor configured to detect contact of a user's hand.

13. A method of setting an orientation of an input arm which controls a surgical arm, the input arm attached to and extending from an input arm support, the input arm configured for manipulation by a user, the method comprising:

selecting a surgical configuration for said surgical arm, selected from a retroflection configuration and a non-retroflection configuration; and based on said selected surgical configuration of said surgical arm, adjusting the orientation of said input arm relative to said input arm support to assume either a first position, in which a handle section of the input arm is more proximal to the user support than said input arm support, or a second position, in which the handle section is more distal to the user support than said input arm support, while under all of said adjustments the handle section of said input arm remains directed towards said user when said user is using a user support located at a fixed position relative to said input arm support.

14. The method according to claim 13, wherein said selecting a surgical configuration includes selecting a location of at least one insertion point of said surgical arm into a patient body.

15. The method according to claim 14, wherein said at least one insertion point comprises an abdominal insertion point or a vaginal insertion point.

16. The method according to claim 13, wherein said selecting a surgical configuration includes selecting a direction of extension of said surgical arm with respect to a field of view of a camera.

17. The method according to claim 16, wherein said surgical configuration includes one of: a surgical configuration in which said camera and said surgical arm are inserted into a patient body in a same direction through a single insertion point; and a surgical configuration in which said camera and said surgical arm are inserted in different direction through different insertion points.

18. The method according to claim 13, wherein said setting an orientation of said input arm comprises positioning at least a portion of said input arm to extend towards said user or positioning at least a portion of said input arm to extend away from said user; said at least a portion of said input arm including a plurality of input arm segments extending between said input arm support and said handle section.

19. The method according to claim 13, wherein said setting an orientation of said input arm comprises adjusting an angle of extension of said input arm relative to a vertical long axis of said input arm support.

20. The method according to claim 19, wherein said angle of extension of said input arm relative to said vertical long axis of said input arm support is selected to provide a user view of said input arm which corresponds to a camera view of said surgical arm.

* * * * *